(12) United States Patent
Vogels et al.

(10) Patent No.: US 6,929,946 B1
(45) Date of Patent: Aug. 16, 2005

(54) GENE DELIVERY VECTORS PROVIDED WITH A TISSUE TROPISM FOR SMOOTH MUSCLE CELLS, AND/OR ENDOTHELIAL CELLS

(75) Inventors: Ronald Vogels, Linschoten (NL); Menzo J. E. Havenga, Alphen aan de Rijn (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 09/444,284

(22) Filed: Nov. 19, 1999

Related U.S. Application Data

(63) Continuation-in-part of application No. 09/348,354, filed on Jul. 7, 1999.

(30) Foreign Application Priority Data

Nov. 20, 1998 (EP) .............................................. 98203921

(51) Int. Cl.$^7$ ........................ C12N 15/00; C12N 15/63; A01N 63/00; C07H 21/04
(52) U.S. Cl. .................. 435/320.1; 435/455; 424/93.2; 424/93.21; 536/23.7; 536/23.72
(58) Field of Search .............................. 435/320.1, 455, 435/325; 424/93.2, 93.21; 536/23.7, 23.72; 514/44

(56) References Cited

U.S. PATENT DOCUMENTS

| | | | |
|---|---|---|---|
| 4,487,829 A | 12/1984 | Sharp et al. .................... 435/5 |
| 4,517,686 A | 5/1985 | Ruoslahti et al. ........... 623/1.49 |
| 4,578,079 A | 3/1986 | Ruoslahti et al. ......... 625/23.76 |
| 4,589,881 A | 5/1986 | Pierschbacher et al. .. 623/23.76 |
| 4,593,002 A | 6/1986 | Dulbecco ................. 435/91.41 |
| 4,792,525 A | 12/1988 | Ruoslahti et al. ........... 435/402 |
| 4,797,368 A | 1/1989 | Carter et al. ............. 435/320.1 |
| 4,956,281 A | 9/1990 | Wallner et al. ............. 435/69.3 |
| 5,024,939 A | 6/1991 | Gorman ..................... 435/69.1 |
| 5,096,815 A | 3/1992 | Ladner et al. .............. 435/69.1 |
| 5,166,320 A | 11/1992 | Wu et al. .................... 530/395 |
| 5,198,346 A | 3/1993 | Ladner et al. .............. 435/69.1 |
| 5,204,445 A | 4/1993 | Plow et al. .................. 530/326 |
| 5,223,394 A | 6/1993 | Wallner .......................... 435/6 |
| 5,223,409 A | 6/1993 | Ladner et al. .............. 435/69.7 |
| 5,240,846 A | 8/1993 | Collins et al. ............... 435/371 |
| 5,246,921 A | 9/1993 | Reddy et al. ................. 514/44 |
| 5,332,567 A | 7/1994 | Goldenberg ............... 424/1.49 |
| 5,349,053 A | 9/1994 | Landolfi ..................... 530/351 |
| 5,403,484 A | 4/1995 | Ladner et al. ........... 435/235.1 |
| 5,436,146 A | 7/1995 | Shenk et al. ................ 435/457 |
| 5,443,953 A | 8/1995 | Hansen et al. ............. 424/1.49 |
| 5,474,935 A | 12/1995 | Chatterjee et al. ........ 435/320.1 |
| 5,521,291 A | 5/1996 | Curiel et al. ........... 530/391.17 |
| 5,534,423 A | 7/1996 | Palsson et al. .............. 435/456 |
| 5,543,328 A | 8/1996 | McClelland et al. ..... 435/320.1 |
| 5,547,932 A | 8/1996 | Curiel et al. ................ 435/456 |
| 5,552,311 A | 9/1996 | Sorscher et al. ............ 435/348 |
| 5,559,099 A | 9/1996 | Wickham et al. ............. 514/44 |
| 5,571,698 A | 11/1996 | Ladner et al. ............ 435/169.7 |
| 5,585,254 A | 12/1996 | Maxwell et al. .......... 435/172.3 |
| 5,622,699 A | 4/1997 | Ruoslahti et al. ........... 424/93.6 |
| 5,631,236 A | * 5/1997 | Woo et al. ..................... 514/44 |
| 5,712,136 A | 1/1998 | Wickham et al. ............ 435/456 |
| 5,731,190 A | 3/1998 | Wickham et al. ......... 435/320.1 |
| 5,756,086 A | 5/1998 | McClelland et al. ....... 424/97.2 |
| 5,770,442 A | * 6/1998 | Wickham et al. ......... 435/320.1 |
| 5,861,290 A | 1/1999 | Goldsmith et al. ....... 435/172.3 |
| 5,922,315 A | 7/1999 | Roy ........................... 424/43.2 |
| 6,127,525 A | * 10/2000 | Crystal et al. .......... 530/388.22 |
| 6,329,190 B1 | 12/2001 | Wickham et al. ......... 435/235.1 |
| 6,455,314 B1 | 9/2002 | Wickham et al. ........... 435/456 |

FOREIGN PATENT DOCUMENTS

| | | |
|---|---|---|
| EP | 259212 | 3/1998 |
| JP | 207631 | 3/1990 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/15644 | 7/1994 |
| WO | WO 94/17832 | 8/1994 |
| WO | WO 94/24299 | 10/1994 |

(Continued)

OTHER PUBLICATIONS

Stevenson et al (1997) Journal of Virology 71: 4782–4790.*
Guzman et al (1994) PNAS 91:10732–10736.*
Verma et al (1997)Nature 389: 239–242.*

(Continued)

*Primary Examiner*—Shin-Lin Chen
(74) *Attorney, Agent, or Firm*—TraskBritt

(57) ABSTRACT

A gene delivery vehicle having been provided with at least a tissue tropism for cells selected from the group of smooth muscle cells, endothelial cells, and/or liver cells. The tissue tropism is generally provided by a virus capsid, such as one comprising protein fragments from at least two different viruses, such as two different adenoviruses, including adenovirus of subgroup C or subgroup B (for example, adenovirus 16). The protein fragments can comprises a tissue tropism determining fragment of a fiber protein derived from a subgroup B adenovirus. Also, cells for producing such gene delivery vehicles and pharmaceutical compositions containing said gene delivery vehicles. Further, a method of delivering nucleic acid to cells such as smooth muscle cells and/or endothelial cells which involves administering to the cells an adenovirus capsid having proteins from at least two different adenoviruses and wherein at least a tissue tropism determining fragment of a fiber protein is derived from a subgroup B adenovirus. Particular construct are also disclosed.

6 Claims, 24 Drawing Sheets

FOREIGN PATENT DOCUMENTS

| WO | WO 94/26915 | 11/1994 |
|---|---|---|
| WO | WO 95/05201 | 2/1995 |
| WO | WO 95/06745 | 3/1995 |
| WO | WO 95/14785 | 6/1995 |
| WO | WO 95/16037 | 6/1995 |
| WO | WO 95/21259 | 8/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 96/00790 | 1/1996 |
| WO | WO 96/07739 | 3/1996 |
| WO | WO 96/10087 | 4/1996 |
| WO | WO 96/13597 | 5/1996 |
| WO | WO 96/14837 | 5/1996 |
| WO | WO 96/17073 | 6/1996 |
| WO | WO 96/18740 | 6/1996 |
| WO | WO 96/26281 | 8/1996 |
| WO | WO 97/00326 | 1/1997 |
| WO | WO 97/24453 | 7/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/22609 | 5/1998 |
| WO | WO 98/32842 | 7/1998 |
| WO | WO 98/40509 | 9/1998 |
| WO | WO 98/50053 A1 | 11/1998 |
| WO | WO 99/47180 A1 | 9/1999 |
| WO | WO 00/31285 A1 | 6/2000 |
| WO | WO 00/52186 A1 | 9/2000 |
| WO | WO 00/70071 A1 | 11/2000 |
| WO | WO 02/24730 A2 | 3/2002 |

OTHER PUBLICATIONS

Wilson et al (1999) Adenovirus Vectors in The Development of Gene Therapy, Friedman, T ed. CSHL Press, Cold Spring Harbor, New York.*
Lusky et al (1998) Journal of Virology, 72:2022–2032.*
Gall et al (1996) Journal of Virology, 70:2116–2123.*
Kaye et al., A single amino acid substitution results in a retinoblastoma protein defective in phosphorylation and oncoprotein binding, Sep. 1990, Proc. Natl. Acad. Sci, vol. 87, p. 6922–6926.*
Rudinger et al., Characteristics of the amino acids as components of a peptide hormone sequence, 1976, Peptide Hormones, p. 1–7.*
Eck et al., Gene–Based Therapy, 1996, Goodman & Gilman's, pp. 77–101.*
Crystal et al., Transfer of Gene to Human: Early Lessons and Obstacles to Success, 1995, Science, vol. 270, pp. 404–410.*
Su et al.; A Genetically Modified Adenoviral Vector Exhibits Enhanced Gene Transfer of Human Smooth Muscle Cells, 2001, Jouranl of Vascular Research, vol. 38: 471–478.*
Verma et al., Gene therapy–promises, problems and prospects, Sep. 18, 1997, Nature, vol. 389, pp. 239–242.*
Deonarain, Ligand–targeted receptor–mediated vectors for gene delivery, 1998, Exp. Opin. Ther. Patents, vol. 8, No. 1, pp. 53–69.*
Wickham et al., Increased In Vitro and In Vivo Gene Transfer by Adenovirus Vectors Containing Chimeric Fiber Protein, Nov. 1997, Journal of Virology, vol. 71, No. 11, pp. 72221–78229.*
Boucher et al., J. Clin. Invest, Feb. 1999, pp. 441–445, vol. 103.
Bowie et al., Science, Mar. 1990, pp. 1306–1310, vol. 247.
Lazarovits et al., J Immunol, 1993, pp. 6482–6489, vol. 151.
Makrides et al., Protein Exp Pur, 1999, pp. 183–202, vol. 17.
Mei et al., Virol, 1998, pp. 254–266, vol. 240.
Miller et al., FASEB J., 1995, pp. 190–199, vol. 9.
Robbins et al., Pharmacol Ther, 1998, pp. 35–47, vol. 80.
Rudinger, Peptide Hormones, Jun. 1976, pp. 1–7.
Russell et al., Nat. Genet, Apr. 1998, pp. 325–330, vol. 18.
Shang et al., J. Immunol, 1998, pp. 267–274, vol. 160.
Zink et al., Gene Ther Mol Biol, Jan. 2001, pp. 1–24, vol. 6.
Albigez–Rizo et al., Human Adenovirus Serotype 3 Fiber Protein, Journal of Biological Chemistry, 266(6), 3961–3967 (1991).
Bai et al., Mutations That Alter an Arg–Gly–Asp (RGD) Sequence in the Adenovirus Type 2 Penton Base Protein Abolish Its Cell–Rounding Activity and Delay Virus Reproduction in Flat Cells, Journal of Virology, 67(9), 5198–5205 (1993).
Bailey et al., Phylogenic Relationships among Adenovirus Serotypes, Virology, 205, 438–452 (1994).
Ball–Goodrich et al., "Paroviral Target Cell Specificity: Acquisition of Fibrotropism by a Mutant of the Lymphotropic Strain of Minute Virus of Mice Involves Multiple Amino Acid Substitutes within the Capsid," Virology, 184, 175–186.
Batra et al., Receptor–mediated gene delivery employing lectin–binding specificity, Gene Therapy, 1, 255–260 (1994).
Boursnell et al., In vivo construction of a recombinant adenovirus Ad2: Ad5, Gene, 13, 311–317 (1981).
Caillet–Boudin et al., Functional and Structural Effects of an Ala to Val Mutation in the Adenovirus Serotype 2 Fibre, J. Mol. Biol., 217, 477–486 (1991).
Chroboczek et al., The Sequence of the Genome of Adenovirus Type 5 and Its Comparison with the Genome of Adenovirus Type 2, Virology, 186, 280–285 (1992).
Chu et al., "Cell targeting with retroviral vector particles containing antibody–envelope fusion proteins," Gene Therapy, I, 292–299 (1994).
Cotten et al., "High–efficiency receptor–mediated delivery of small and large (48 kilobase gene constructs using the endosome–disruption activity of defective or chemically inactivated adenovirus particles," Proc. Natl. Acad, Sci. USA, 89, 6094–6098 (1992).
Cotten et al., "Transferrin–polycation–mediated introduction of DNA into human leukemic cells Stimulation by agents that affect the survival of transfected DNA or modulate transferrin receptor levels," Proc. Natl. Acad. Sci. USA, 87, 4033–4037 (1990).
Crawford–Miksza et al., Adenovirus Serotype Evolution Is Driven by Illegitimate Recombination in the Hypervariable Regions of the Hexon Protein, Virology, 224, 357–367 (1996).
Crawford–Miksza et al., Analysis of 15 Adenovirus Hexon Proteins Reveals the Location and Structure of Seven Hypervariable Regions Containing Serotype–Specific Residues, J. Virol., 70(3), 1836–1844 (1996).
Crompton et al., Expression of a foreign epitope on the surface of the adenovirus hexon, J. Gen. Virol., 75(1), 133–139 (1994).
Crystal, Transfer of Genes to Humans Early Lessons and Obstacles to Success, Science, 270, 404–410 (1995).

Curiel et al., "Adenovirus enhancement of transferrin–polylysine–mediated gene delivery," Proc. Natl. Acad. Sci. USA, 88, 8850–8854 (1991).

Curiel et al., "High–Efficiency Gene Transfer Mediated by Adenovirus Coupled to DNA–Polylysine Complexes," Human Gene Therapy, 3, 147–154 (1992).

De Jong et al., "Adenoviruses from Human Immunodeficiency Virus–Infected Individuals, Including Two Strains That Represent New Candidate Serotypes Ad50 and Ad51 of Species B1 and D, Respectively," 37(12) Journal of Clinical Microbiology 3940–45, American Society for Microbiology (Dec. 1999).

Defer et al., Human Adenovirus–Host Cell Interactions: Comparative Study with Members of Subgroups B and C, Journal of Virology, 64(8), 3661–3673 (1990).

Dupuit et al., "Regenerating Cells in Human Airwey Surface Epithelium Represent Preferential Targets for Recombinant Adenovirus," Human Gene Therapy, 6, 1185–1193 (1995).

Etienne–Julan et al., "The efficiency of cell targeting by recombinant retroviruses depends on the nature of the receptor and the composition of the artificial cell–virus linker," Journal of General Virology, 73, 3251–3255 (1992).

Falgout et al., Characterization of Adenovirus Particles Made by Deletion Mutuants Lacking the Fiber Gene, Journal of Virology, 62(2), 622–625 (1988).

Gall et al., "Adenovirus type 5 and 7 capsid chimera: Fiber replacement alters receptor tropism without affecting primary immune neutralization epitopes," 70(4) Journal of Virology 2116–23 (1996).

Gall et al., "Construction and characterization of Hexon–Chimeric Adenoviruses: Specification of adenovirus serotype," 72(12) Journal of Virology 10260–64 (1998).

Greber et al., "Stepwise Dismantling of Adenovirus 2 during Entry into Cells," Cell, 75, 477–486 (1993).

Green et al., Evidence for a repeating cross–$\beta$ sheet structure in the adenovirus fibre, EMBO Journal, 2(8), 1357–1365 (1983).

Han et al., "Ligand–directed retroviral targeting of human breast cancer cells," Proc. Natl. Acad. Sci. USA, 92, 9747–9751 (1995).

Henry et al., Characterization of the Knob Domain of the Adenovirus Type 5 Fiber Protein Expressed in *Escherichia coli*, Journal of Virology, 68(8), 5239–5246 (1994).

Hong et al., The Amino Terminus of the Adenovirus Fiber Protein Encodes the Nuclear Localization Signal, Virology, 185(2), 758–767 (1991).

Horvath et al., "Nonpermissively of Human Blood Lymphocytes to Adenovirus Type 2 Infection," Journal of Virology, 62(1), 341–345 (1988).

Huang et al., "Upregulation of Integrins $\alpha v\beta 3$ and $\alpha v\beta 5$ on Human Monocytes and T Lymphocytes Facilitates Adenovirus–Mediated Gene Delivery," Journal of Virology, 69(4), 2257–2263 (1995).

Karayan et al., Oligomerization of Recombinant Penton Base of Adenovirus Type 2 and Its Assembly with Fiber in Baculovirus–Infected Cells, Virology, 202, 782–795 (1994).

Kass–Eisler et al., "Quantitative determination of adenovirus–mediated gene delivery to rat cardiac myocytes in vitro and in vivo," Proc. Natl. Acad. Sci. USA, 90, 11498–11502 (1993).

Komoriya et al., The Minimal Essential Sequence for a Major Cell Type–specific Adhesion Site (CSI) within the Alternatively Spliced Type III Connecting Segment Domain of Fibronectin Is Leucine–Aspartic Acid–Valine,: Journal of Biological Chemistry, 266(23), 15075–15079 (1991).

Maraveyas et al., "Targeted Immunotherapy—An update with special emphasis on ovarian cancer," Acta Oncologica, 32(7/8), 741–746 (1993).

Mastrangeli et al., "Sero–Switch" Adenovirus–Mediated In Vivo Gene Transfer: Circumvention of Anti–Adenovirus Humoral Immune Defenses Against Repeat Adenovirus Vector Administration by Changing the Adenovirus Serotype, Human Gene Therapy, 7, 79–87 (1996).

Matrangeli et al., "In Vivo Gene Transfer to the Lung of Experimental Animals Using a Chimeric Ad5/Ad7 Adenovirus Vector," Ped. Pulm, Suppl., 12, 230, Abst. No. 180 (1995).

Mathias et al., Multiple Adenovirus Serotypes Use $\alpha v$ Integrins for Infection, Journal of Virology, 68(10), 6811–6814 (1994).

Mautner et al., Recombination in Adeniovirus: Analysis of Crossover Sites in Intertypic Overlap Recombinants, Virology, 139, 43–52, (1984).

Mautner et al., Recombination in Adenovirus: DNA Sequence Analysis of Crossover Sites in Intertypic Recombinants, Virology, 131, 1–10 (1983).

Michael et al., "Binding–incompetent Adenovirus Facilitates Molecular Conjugate–mediated Gene Transfer by the Receptor–mediated Endocytosis Pathway," Journal of Biological Chemistry, 268(10), 6866–6869 (1993).

Michael et al., Addition of a short peptide ligand to the adenovirus fiber protein, Gene Therapy, 2, 660–668 (1995).

Miller et al., Targeted vectors for gene therapy, FASEB Journal, 9, 190–199 (1995).

NEDA et al., "Chemical Modification of an Ecotropic Murine Leukemia Virus Results in Redirection of Its Target Cell Specificity," Journal of Biological Chemistry, 266(22), 14143–14146 (1991).

Nemerow et al., Adenovirus entry into host cells: a role for $\alpha v$ integrins, Trends In Cell Biology, 4, 52–55 (1994).

Nemerow et al., The Role of $\alpha v$ Integrins in Adenovirus Infection, Biology of Vitronectins and their Receptors, 177–184 (1993).

Novelli et al., Deletion Analysis of Functional Domains in Baculovirus–Expressed Adenovirus Type 2 Fiber, Virology, 185, 365–376 (1991).

Orkin et al., "Report and Recommendations of the Panel to Assess the NIH Investment in Research on Gene Therapy," (1995), file://F1/N1Hrec.htm Jan. 4, 2001 1:37 pm.

PCT International Preliminary Examination Report, PCT/EP01/10999, dated Sep. 23, 2002 (11 pages).

PCT International Search Report, International Application No. PCT/EP01/10999, dated Mar. 26, 2002 (6 pages).

Peteranderl et al., "Trimerization of the Heat Shock Transcription Factor by a Triple–Stranded $\alpha$–Helical Coiled–Coil," Biochemistry, 31, 12272–12276 (1992).

Pring–Akerblom et al., Sequence Charaterization and Comparison of Human Adenovirus Subgenus B and E Hexons, Virology, 212, 232–36 (1995).

Roberts et al., Three–Dimensional Structure of the Adenovirus Major Coat Protein Hexon, Science, 232, 1148–51 (1986).

Russell et al., "Retroviral vectors displaying functional antibody fragments," Nucleic Acids Research, 21(5), 1081–1085 (1993).

Signäs et al., Adenovirus 3 Fiber Polypeptide Gene: Implications for the Structure of the Fiber Protein, Journal of Virology, 53(2), 672–678 (1985).

Silver et al., Interactions of Human Adenovirus Serotype 2 with Human Lymphoid Cells, Virology, 165, 377–387 (1988).

Stevenson et al., "Selective targeting of human cells by a chimeric adenovirus vector containing a modified fiber protein," 71(6) Journal of Virology, 4782–90 (1997).

Stewart et al., Difference imaging of adenovirus: bridging the resolution gap between X-ray crystallography and electron microscopy, EMBO Journal, 12(7), 2589–2599 (1993).

Verma et al., Gene Therapy—promises, problems and prospects, Nature, 389, 239–42 (1997).

Wadell, G., Molecular Epidermiology of Human Adenovirus, Curr. Top. Microbiol. Immunol., 110, 191–220 (1984).

Watson et al., "An Antigenic Analysis of the Adenovirus Type 2 Fibre Polypeptide," Journal of Virology, 69, 525–535.

Watson et al., An Antigenic Analysis of the Adenovirus Type 2 Fibre Polypeptide, Journal of Virology, 69, 525–535.

Wickham et al., Integrin $\alpha v \beta 5$ Selectivity Promotes Adenovirus Cell Membrane Permeabilization, Journal of Cell Biology, 127(1), 257–264 (1994).

Wickham et al., Integrins $\alpha v \beta 3$ and $\alpha v \beta 5$ Promote Adenovirus Internalization by Not Virus Attachment, Cell, 73, 309–319 (1993).

* cited by examiner

Figure 4A: Sequence of Ad5 fiber

```
ATGAAGCGCGCAAGACCGTCTGAAGATACCTTCAACCCCGTGTATCCATATGACACGGAAACCGGTC
CTCCAACTGTGCCTTTTCTTACTCCTCCCTTTGTATCCCCCAATGGGTTTCAAGAGAGTCCCCCTGG
GGTACTCTCTTTGCGCCTATCCGAACCTCTAGTTACCTCCAATGGCATGCTTGCGCTCAAAATGGGC
AACGGCCTCTCTCTGGACGAGGCCGGCAACCTTACCTCCCAAAATGTAACCACTGTGAGCCCACCTC
TCAAAAAAACCAAGTCAAACATAAACCTGGAAATATCTGCACCCCTCACAGTTACCTCAGAAGCCCT
AACTGTGGCTGCCGCCGCACCTCTAATGGTCGCGGGCAACACACTCACCATGCAATCACAGGCCCCG
CTAACCGTGCACGACTCCAAACTTAGCATTGCCACCCAAGGACCCCTCACAGTGTCAGAAGGAAAGC
TAGCCCTGCAAACATCAGGCCCCCTCACCACCACCGATAGCAGTACCCTTACTATCACTGCCTCACC
CCCTCTAACTACTGCCACTGGTAGCTTGGGCATTGACTTGAAAGAGCCCATTTATACACAAAATGGA
AAACTAGGACTAAAGTACGGGGCTCCTTTGCATGTAACAGACGACCTAAACACTTTGACCGTAGCAA
CTGGTCCAGGTGTGACTATTAATAATACTTCCTTGCAAACTAAAGTTACTGGAGCCTTGGGTTTTGA
TTCACAAGGCAATATGCAACTTAATGTAGCAGGAGGACTAAGGATTGATTCTCAAAACAGACGCCTT
ATACTTGATGTTAGTTATCCGTTTGATGCTCAAAACCAACTAAATCTAAGACTAGGACAGGGCCCTC
TTTTTATAAACTCAGCCCACAACTTGGATATTAACTACAACAAAGGCCTTTACTTGTTTACAGCTTC
AAACAATTCCAAAAAGCTTGAGGTTAACCTAAGCACTGCCAAGGGGTTGATGTTTGACGCTACAGCC
ATAGCCATTAATGCAGGAGATGGGCTTGAATTTGGTTCACCTAATGCACCAAACACAAATCCCCTCA
AAACAAAAATTGGCCATGGCCTAGAATTTGATTCAAACAAGGCTATGGTTCCTAAACTAGGAACTGG
CCTTAGTTTTGACAGCACAGGTGCCATTACAGTAGGAAACAAAAATAATGATAAGCTAACTTTGTGG
ACCACACCAGCTCCATCTCCTAACTGTAGACTAAATGCAGAGAAAGATGCTAAACTCACTTTGGTCT
TAACAAAATGTGGCAGTCAAATACTTGCTACAGTTTCAGTTTTGGCTGTTAAAGGCAGTTTGGCTCC
AATATCTGGAACAGTTCAAAGTGCTCATCTTATTATAAGATTTGACGAAAATGGAGTGCTACTAAAC
AATTCCTTCCTGGACCCAGAATATTGGAACTTTAGAAATGGAGATCTTACTGAAGGCACAGCCTATA
CAAACGCTGTTGGATTTATGCCTAACCTATCAGCTTATCCAAAATCTCACGGTAAAACTGCCAAAAG
TAACATTGTCAGTCAAGTTTACTTAAACGGAGACAAAACTAAACCTGTAACACTAACCATTACACTA
AACGGTACACAGGAAACAGGAGACACAACTCCAAGTGCATACTCTATGTCATTTTCATGGGACTGGT
CTGGCCACAACTACATTAATGAAATATTTGCCACATCCTCTTACACTTTTTCATACATTGCCCAAGA
ATAA
```

Figure 4B: Sequence of Ad5/fib12 chimeric fiber

ATGAAGCGCGCAAGACCGTCTGAAGATACCTTCAACCCCGTGTATCCATATGACCCATTTGACACAT
CAGACGTACCCTTTGTTACACCCCCTTTTACTTCTTCCAATGGTCTTCAAGAAAAACCACCAGGTGT
ATTAGCACTTAATTACAAAGACCCCATTGTAACTGAAAATGGAACCCTTACACTCAAGCTAGGGGAC
GGAATAAAACTTAATGCCCAAGGTCAACTTACAGCTAGTAATAATATCAATGTTTTGGAGCCCCTTA
CCAACACCTCACAAGGTCTTAAACTTTCTTGGAGCGCCCCCCTAGCAGTAAAGGCTAGTGCCCTCAC
ACTTAACACAAGAGCGCCCTTAACCACAACGGATGAAAGCTTAGCCTTAATAACCGCCCCTCCCATT
ACAGTAGAGTCTTCGCGTTTGGGCTTGGCCACCATAGCCCCTCTAAGCTTAGATGGAGGTGGAAACC
TAGGTTTAAATCTTTCTGCTCCCCTGGACGTTAGTAACAACAATTTGCATCTCACCACTGAAACTCC
CTTAGTTGTAAATTCTAGCGGTGCCCTATCTGTTGCTACTGCAGACCCCATAAGTGTTCGCAACAAC
GCTCTTACCCTACCTACGGCAGATCCGTTAATGGTGAGCTCCGATGGGTTGGGAATAAGTGTCACTA
GTCCCATTACAGTAATAAACGGTTCCTTAGCCTTGTCTACAACTGCTCCCCTCAACAGCACAGGATC
CACTTTAAGTCTGTCTGTTGCCAATCCTCTGACTATTTCACAAGACACATTGACTGTTTCCACTGGT
AACGGTCTTCAAGTGTCGGGGTCTCAATTAGTAACAAGAATAGGGGATGGTTTAACATTCGATAATG
GGGTCATGAAAGTAAACGTTGCCGGGGGAATGAGAACTTCTGGCGGTAGAATAATTTTAGATGTTAA
TTATCCCTTTGATGCGAGCAATAACCTGTCCTTAAGACGGGGATTGGGACTAATTTATAACCAATCT
ACAAACTGGAACTTAACAACTGATATTAGTACCGAAAAAGGTTTAATGTTTAGTGGCAATCAAATAG
CTCTTAATGCAGGTCAGGGGCTTACATTTAATAATGGCCAACTTAGGGTTAAGTTGGGAGCTGGACT
TATTTTTGATTCAAACAATAACATTGCCTTAGGCAGCAGCAGCAACACTCCATACGACCCTCTGACA
CTGTGGACAACTCCTGACCCACCACCAAACTGCAGCCTCATACAAGAGCTAGATGCAAAACTCACCC
TGTGCTTAACAAAAAACGGATCTATTGTTAATGGCATTGTAAGTTTAGTGGGTGTTAAGGGTAATCT
CCTAAATATCCAAAGTACTACTACCACTGTAGGAGTGCATTTAGTGTTTGATGAACAGGGAAGATTA
ATCACATCAACCCCTACTGCCCTGGTTCCCCAAGCTTCGTGGGGATATAGACAAGGCCAATCAGTGT
CTACCAATACTGTTACCAATGGTCTAGGTTTTATGCCTAATGTGAGTGCTTACCCTAGACCAAATGC
CAGTGAGGCTAAAAGCCAAATGGTAAGTCTCACGTACTTACAGGGAGATACATCTAAACCTATAACA
ATGAAAGTTGCATTTAATGGCATTACGTCGCTAAATGGATACTCTTTAACATTCATGTGGTCAGGTC
TATCAAACTATATAAATCAGCCTTTCTCTACACCATCCTGCTCCTTNTCTTACATTGCCCAAGAA**TA
AA**TGCATTAG

Figure 4C: Sequence of Ad5/fib16 chimeric fiber

```
ATGAAGCGCGCAAGACCGTCTGAAGATACCTTCAACCCCGTGTATCCATATGAAGATGAAAGCAGCT
CACAACACCCCTTTATAAACCCTGGTTTCATTTCCTCAAATGGTTTTGCACAAAGCCCAGATGGAGT
TCTAACTCTTAAATGTGTTAATCCACTCACTACCGCCAGCGGACCCCTCCAACTTAAAGTTGGAAGC
AGTCTTACAGTAGATACTATCGATGGGTCTTTGGAGGAAAATATAACTGCCGAAGCGCCACTCACTA
AAACTAACCACTCCATAGGTTTATTAATAGGATCTGGCTTGCAAACAAAGGATGATAAACTTTGTTT
ATCGCTGGGAGATGGGTTGGTAACAAAGGATGATAAACTATGTTTATCGCTGGGAGATGGGTTAATA
ACAAAAAATGATGTACTATGTGCCAAACTAGGACATGGCCTTGTGTTTGACTCTTCCAATGCTATCA
CCATAGAAAACAACACCTTGTGGACAGGCGCAAAACCAAGCGCCAACTGTGTAATTAAAGAGGGAGA
AGATTCCCCAGACTGTAAGCTCACTTTAGTTCTAGTGAAGAATGGAGGACTGATAAATGGATACATA
ACATTAATGGGAGCCTCAGAATATACTAACACCTTGTTTAAAAACAATCAAGTTACAATCGATGTAA
ACCTCGCATTTGATAATACTGGCCAAATTATTACTTACCTATCATCCCTTAAAAGTAACCTGAACTT
TAAAGACAACCAAAACATGGCTACTGGAACCATAACCAGTGCCAAAGGCTTCATGCCCAGCACCACC
GCCTATCCATTTATAACATACGCCACTGAGACCCTAAATGAAGATTACATTTATGGAGAGTGTTACT
ACAAATCTACCAATGGAACTCTCTTTCCACTAAAAGTTACTGTCACACTAAACAGACGTATGTTAGC
TTCTGGAATGGCCTATGCTATGAATTTTCATGGTCTCTAAATGCAGAGGAAGCCCCGGAAACTACC
GAAGTCACTCTCATTACCTCCCCCTTCTTTTTTTCTTATATCAGAGAAGATGACTGAATGCATTAG
```

Figure 4D: Sequence of Ad5/fib28 chimeric fiber

ATGTTGTTGCAGATGAAGCGCGCAAGACCGTCTGAAGATACCTTCAACCCCGTGTATCCATATGGCT
ACGCGCGGAATCAGAATATCCCCTTCCTCACTCCCCCCTTTGTTTCTTCCGATGGATTCCAAAACTT
CCCACCTGGGGTCCTGTCACTCAAACTGGCTGACCCAATCACCATCGCTAATGGGGATGTCTCACTC
AAGTTGGGAGGCGGACTGACGGTGGAAAAAGAGTCTGGAAACTTAACTGTGAACCCTAAGGCTCCCT
TGCAAGTTGCAAGTGGACAATTGGAATTAGCATATGATTCTCCATTTGATGTTAAAAACAATATGCT
TACTCTTAAAGCAGGTCACGGCTTAGCAGTTGTAACGAAAGACAATACTGATTTACAACCACTAATG
GGCACACTTGTTGTTTTAACTGGCAAAGGCATTGGCACTGGCACAAGTGCTCACGGTGGAACCATAG
ATGTGAGAATAGGAAAAAACGGAAGTCTGGCATTTGACAAAAATGGAGATTTGGTGGCCTGGGATAA
AGAAAATGACAGGCGCACTCTATGGACAACTCCAGACACATCTCCAAATTGCAAAATGAGTGAAGTC
AAAGACTCAAAGCTTACTCTTATTCTTACAAAATGCGGAAGTCAAATTCTAGGAAGTGTATCTTTGC
TTGCTGTAAAAGGAGAATATCAAAATATGACTGCCAGTACTAATAAGAATGTAAAAATAACACTGCT
ATTTGATGCTAATGGAGTCTTGTTAGAAGGATCCAGTCTTGATAAGAGTACTGGAACTTTAGAAAC
AATGATTCTACTGTGTCTGGAAAATATGAAAATGCTGTTCCGTTCATGCCTAACATAACAGCTTATA
AACCCGTCAATTCTAAAAGCTATGCCAGAAGTCACATATTTGGAAATGTATATATTGCTGCTAAGCC
ATATAATCCAGTGGTTATTAAAATTAGCTTCAATCAAGAGACACAAAACAATTGTGTCTATTCTATA
TCATTTGACTACACTTGCTCTAAAGAGTATACAGGTATGCAATTCGATGTTACATCTTTCACCTTCT
CCTATATCGCCCAAGAATGAATGCATTAG

Figure 4E: Sequence of Ad5/fib40-L chimeric fiber

ATGTTGTTGCAGATGAAGCGCGCAAGACCGTCTGAAGATACCTTCAACCCCGTGTATCCATATGAAC
ACTACAATCCCCTTGACATTCCATTTATTACACCCCGTTTGCTTCCTCCAACGGCTTGCAAGAAAA
ACCTCCGGGAGTCCTCAGCCTGAAATACACTGATCCACTTACAACCAAAAACGGGGCTTTAACCTTA
AAATTGGGCACGGGACTAAACATTGATAAAAATGGAGATCTTTCTTCAGATGCTAGCGTGGAAGTTA
GCGCCCCTATCACTAAAACCAACAAAATCGTAGGTTTAAATTACACTAAGCCTCTCGCTCTGCAAAA
TAACGCGCTTACTCTTTCTTACAACGCGCCCTTTAACGTAGTAAATAATAATTTAGCTCTAAATATG
TCACAGCCTGTTACTATTAATGCAAACAACGAACTTTCTCTCTTAATAGACGCCCCACTTAATGCTG
ACACGGGCACTCTTCGCCTTCGAAGTGATGCACCTCTTGGACTAGTAGACAAAACACTAAAGGTTTT
GTTTTCTAGCCCCCTCTATCTAGATAATAACTTTCTTACACTAGCCATTGAACGCCCGCTAGCTCTA
TCCAGTAACAGAGCAGTGGCCCTTAAGTATTCACCACCTTTAAAAATAGAAAACGAAAACTTAACCC
TAAGCACAGGCGGACCTTTTACTGTAAGCGGGGGAAATTTAAACCTGGCAACATCGGCACCCCTCTC
CGTGCAAAACAATTCTCTCTCCTTAGGGGTTAACCCGCCTTTTCTCATCACTGACTCTGGATTAGCT
ATGGACTTAGGAGACGGTCTTGCATTAGGTGGCTCTAAGTTAATAATCAATCTTGGTCCAGGTTTAC
AAATGTCTAATGGAGCTATTACTTTAGCACTAGATGCAGCGCTGCCTTTGCAATATAAAAACAACCA
ACTTCAACTCAGAATTGGCTCCGCGTCTGCTTTAATTATGAGCGGAGTAACACAAACATTAAACGTC
AATGCCAATACCAGCAAAGGTCTTGCTATTGAAAATAACTCACTAGTTGTTAAGCTAGGAAACGGTC
TTCGCTTTGATAGCTGGGGAAGCATAGCTGTCTCACCTACTACCACTACCCCTACCACCCTATGGAC
CACCGCGGACCCGTCTCCTAACGCCACTTTTTATGAATCACTAGACGCCAAAGTGTGGCTAGTTTTA
GTAAAATGCAACGGCATGGTTAACGGGACCATATCCATTAAAGCTCAAAAAGGCACTTTACTTAAAC
CCACAGCTAGCTTTATTTCCTTTGTCATGTATTTTTACAGCGACGGAACGTGGAGGAAAAACTATCC
CGTGTTTGACAACGAAGGGATACTAGCAAACAGTGCCACATGGGGTTATCGACAAGGACAGTCTGCC
AACACTAACGTTTCCAATGCTGTAGAATTTATGCCTAGCTCTAAAAGGTATCCCAATGAAAAGGTT
CTGAAGTTCAGAACATGGCTCTTACCTACACTTTTTTGCAAGGTGACCCTAACATGGCCATATCTTT
TCAGAGCATTTATAATCATGCAATAGAAGGCTACTCATTAAAATTCNCCTGGCGCGTTCGAAATAAT
GAACGTTTTGACATCCCCTGTTGCTCATTTTCTTATGTAACAGAACAATAAATGCATTAG

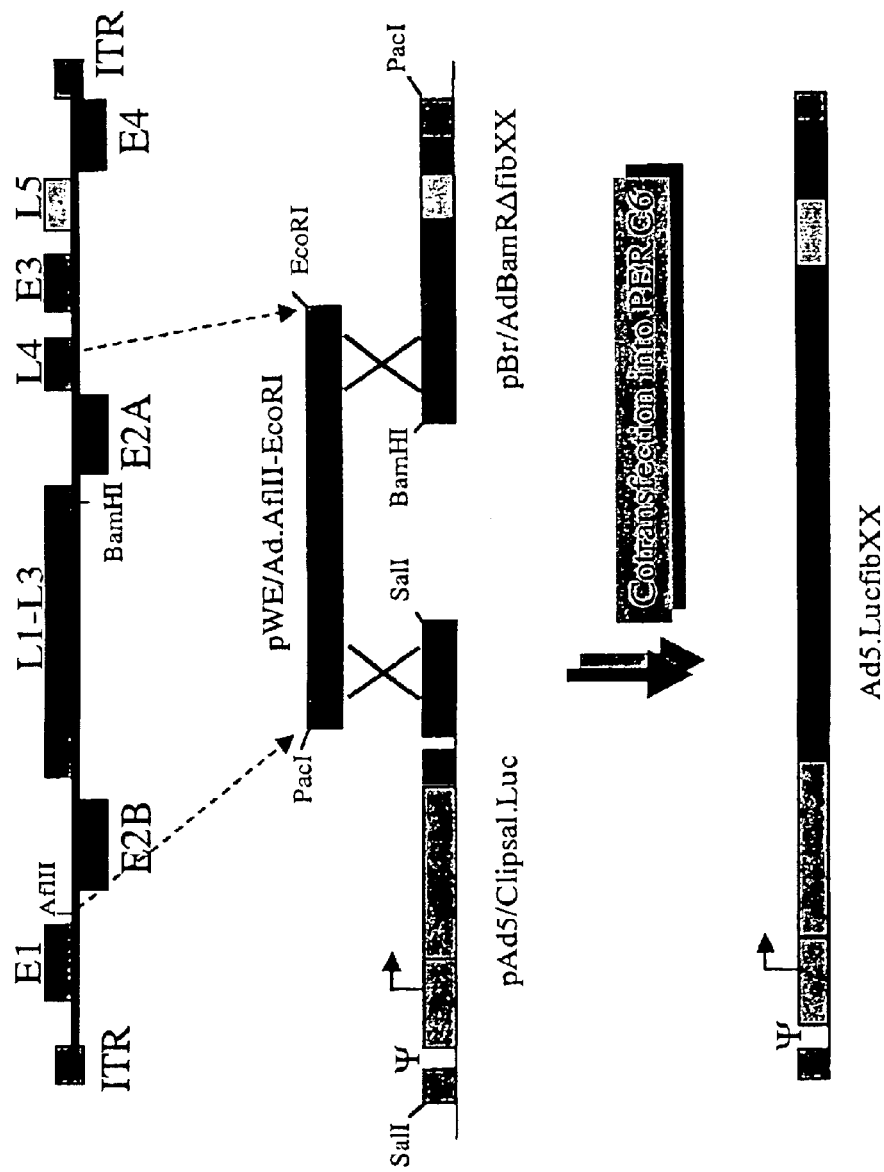
Figure 6: Generation of (chimaeric) adenoviruses

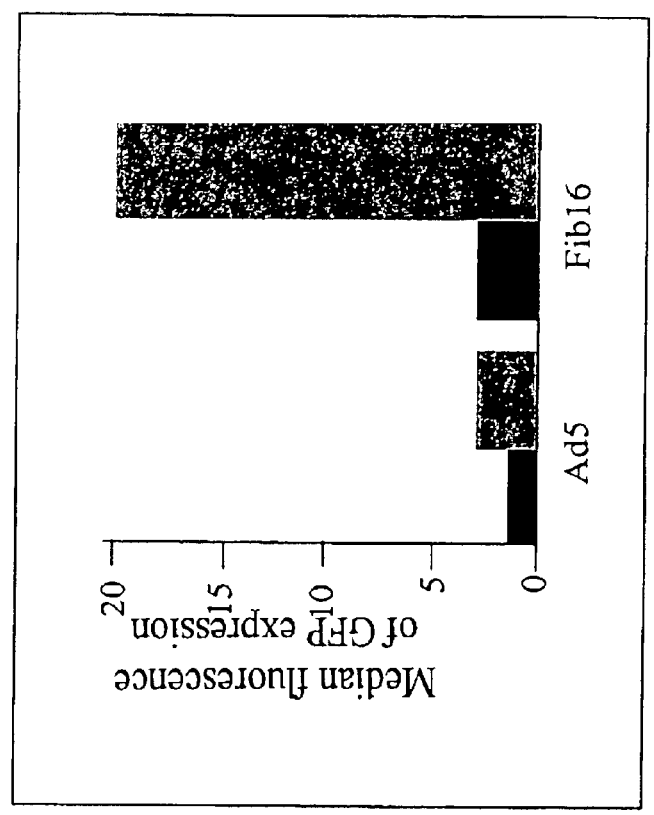

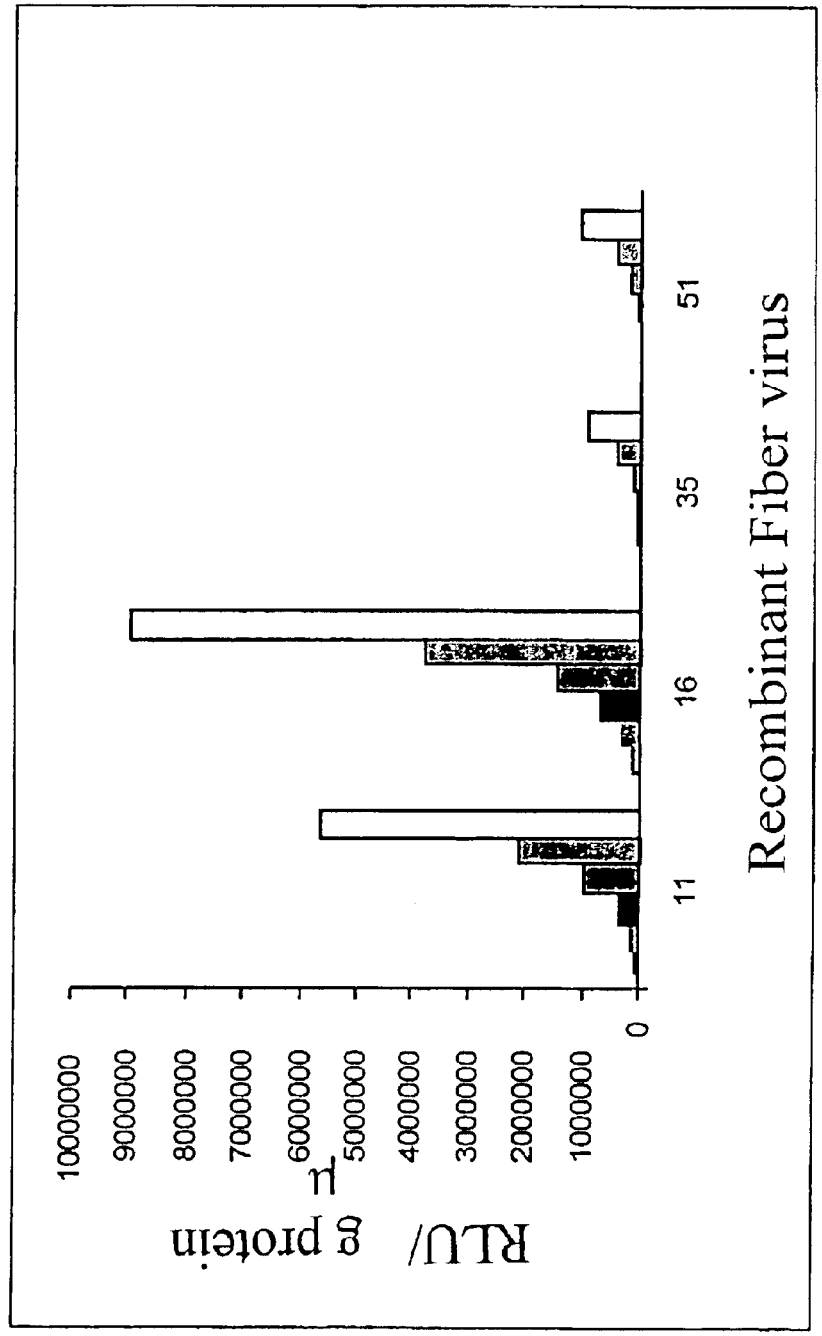

Figure 8e:
Ad5Fiber 51.ntLacZ
Ad5Fiber 16.ntLacZ
Ad5.ntLacZ
Negative control Figure 8f
Ad5Fiber 51.ntLacZ
Ad5Fiber 16.ntLacZ
Ad5.ntLacZ
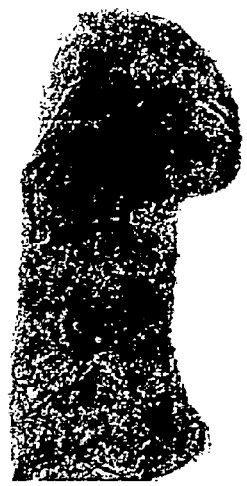
Negative control

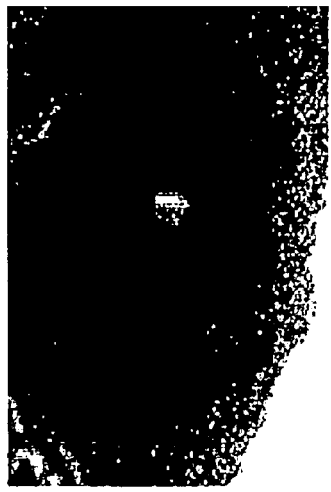
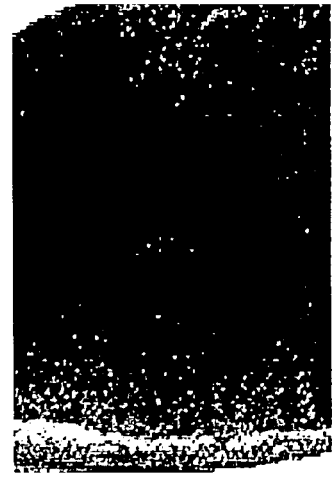
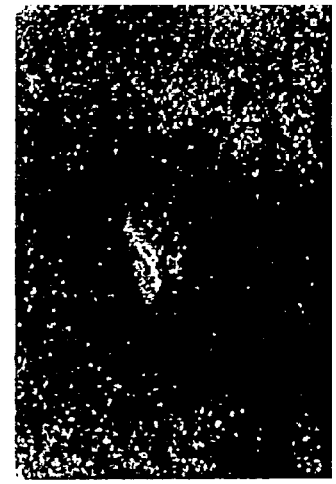
Figure 8g

Figure 8h
Ad5Fiber 51.ntLacZ
Ad5Fiber 16.ntLacZ
Ad5.ntLacZ
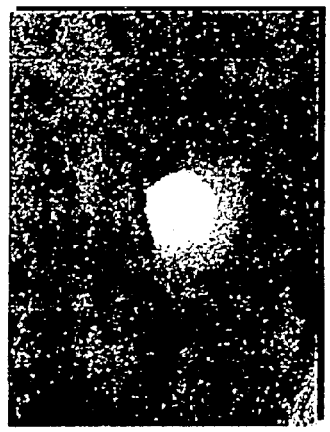
Negative control

Figure 9A

Alignment Report of Untitled, using Clustal method with Weighted residue weight table.
Thursday, November 19, 1998 18:25

```
1    A T G G C - - - - C A A A C G A G C T C G G C T A A G C A G C T - - - - - - - -    Ad16 genbank.seq
1    A T G T T G T T G C A G A T G A A G C G C G C A A G A C C G T C T G A A G A T A    Ad5/fib16.seq 29   C C T T C A A T C C G G T C T A C C C C T A T G A A G A T G A A A G C A G C T C    Ad16 genbank.seq
41   C C T T C A A C C C C G T G T A T C C A T A T G A A G A T G A A A G C A G C T C    Ad5/fib16.seq 69   A C A A C A C C C C T T T A T A A A C C T G G T T T C A T T T C C T C A A A T      Ad16 genbank.seq
81   A C A A C A C C C C T T T A T A A A C C T G G T T T C A T T T C C T C A A A T      Ad5/fib16.seq 109  G G T T T T G C A C A A A G C C C A G A T G G A G T T C T A A C T C T T A A A T    Ad16 genbank.seq
121  G G T T T T G C A C A A A G C C C A G A T G G A G T T C T A A C T C T T A A A T    Ad5/fib16.seq 149  G T G T T A A T C C A C T C A C T A C C G C C A G C G G A C C - C C T C C A A C T  Ad16 genbank.seq
161  G T G T T A A T C C A C T C A C T A C C G C C A G C G G A C C C C T C C A A C T    Ad5/fib16.seq 189  T A A A G T T G G A A G C A G T C T T A C A G T A G A T A C T A T C G A T G G G    Ad16 genbank.seq
201  T A A A G T T G G A A G C A G T C T T A C A G T A G A T A C T A T C G A T G G G    Ad5/fib16.seq 229  T C T T T G G A G G A A A A T A T A A C T G C C G C A G C G C C A C T C A C T A    Ad16 genbank.seq
241  T C T T T G G A G G A A A A T A T A A C T G C C G A A G C G C C A C T C A C T A    Ad5/fib16.seq 269  A A A C T A A C C A C T C C A T A G G T T T A T T A A T A G G A T C T G G C T T    Ad16 genbank.seq
281  A A A C T A A C C A C T C C A T A G G T T T A T T A A T A G G A T C T G G C T T    Ad5/fib16.seq 309  G C A A A C A A G G A T G A T A A A C T T T G T T T A T C G C T G G G A G A T      Ad16 genbank.seq
321  G C A A A C A A G G A T G A T A A A C T T T G T T T A T C G C T G G G A G A T      Ad5/fib16.seq 349  G G G T T G G T A A C A A A G G A T G A T A A A C T A T G T T T A T C G C T G G    Ad16 genbank.seq
361  G G G T T G G T A A C A A A G G A T G A T A A A C T A T G T T T A T C G C T G G    Ad5/fib16.seq 389  G A G A T G G G T T A A T A A C A A A A A A T G A T G T A C T A T G T G C C A A    Ad16 genbank.seq
401  G A G A T G G G T T A A T A A C A A A A A A T G A T G T A C T A T G T G C C A A    Ad5/fib16.seq 429  A C T A G G A C A T G G C C T T G T G T T T G A C T C T T C C A A T G C T A T C    Ad16 genbank.seq
441  A C T A G G A C A T G G C C T T G T G T T T G A C T C T T C C A A T G C T A T C    Ad5/fib16.seq 469  A C C A T A G A A A A C A A C A C C T T G T G G A C A G G C G C A A A A C C A A    Ad16 genbank.seq
481  A C C A T A G A A A A C A A C A C C T T G T G G A C A G G C G C A A A A C C A A    Ad5/fib16.seq 509  G C G C C A A C T G T G T A A T T A A A G A G G G A G A A G A T T C C C C A G A    Ad16 genbank.seq
521  G C G C C A A C T G T G T A A T T A A A G A G G G A G A A G A T T C C C C A G A    Ad5/fib16.seq 549  C T G T A A G C T C A C T T T A G T T C T A G T G A A G A A T G G A G G A C T G    Ad16 genbank.seq
561  C T G T A A G C T C A C T T T A G T T C T A G T G A A G A A T G G A G G A C T G    Ad5/fib16.seq 589  A T A A A T G G A T A C A T A A C A T T A A T G G G A G C C T C A G A A T A T A    Ad16 genbank.seq
601  A T A A A T G G A T A C A T A A C A T T A A T G G G A G C C T C A G A A T A T A    Ad5/fib16.seq 629  C T A A C A C C T T G T T T A A A A A C A A T C A A G T T A C A A T C G A T G T    Ad16 genbank.seq
641  C T A A C A C C T T G T T T A A A A A C A A T C A A G T T A C A A T C G A T G T    Ad5/fib16.seq 669  A A A C C T C G C A T T T G A T A A T A C T G G C C A A A T T A T T A C T T A C    Ad16 genbank.seq
681  A A A C C T C G C A T T T G A T A A T A C T G G C C A A A T T A T T A C T T A C    Ad5/fib16.seq 709  C T A T C A T C C C T T A A A A G T A A C C T G A A C T T T A A A G A C A A C C    Ad16 genbank.seq
721  C T A T C A T C C C T T A A A A G T A A C C T G A A C T T T A A A G A C A A C C    Ad5/fib16.seq
```

Figure 9A, contd.

Alignment Report of Untitled, using Clustal method with Weighted residue weight table.
Thursday, November 19, 1998 18:26

```
749   A A A C A T G G C T A C T G G A A C C A T A A C C A G T G C C A A A G G C T T   Ad16 genbank.seq
761   A A A C A T G G C T A C T G G A A C C A T A A C C A G T G C C A A A G G C T T   Ad5/fib16.seq 789   C A T G C C C A G C A C C A C C G C C T A T C C A T T T A T A A C A T A C G C C   Ad16 genbank.seq
801   C A T G C C C A G C A C C A C C G C C T A T C C A T T T A T A A C A T A C G C C   Ad5/fib16.seq 829   A C T G A G A C C C T A A A T G A A G A T T A C A T T T A T G G A G A G T G T T   Ad16 genbank.seq
841   A C T G A G A C C C T A A A T G A A G A T T A C A T T T A T G G A G A G T G T T   Ad5/fib16.seq 869   A C T A C A A A T C T A C C A A T G G A A C T C T C T T T C C A C T A A A A G T   Ad16 genbank.seq
881   A C T A C A A A T C T A C C A A T G G A A C T C T C T T T C C A C T A A A A G T   Ad5/fib16.seq 909   T A C T G T C A C A C T A A A C A G A C G T A T G T T A G C T T C T G G A A T G   Ad16 genbank.seq
921   T A C T G T C A C A C T A A A C A G A C G T A T G T T A G C T T C T G G A A T G   Ad5/fib16.seq 949   G C C T A T G C T A T G A A T T T T T C A T G G T C T C T A A A T G C A G A G G   Ad16 genbank.seq
961   G C C T A T G C T A T G A A T T T T T C A T G G T C T C T A A A T G C A G A G G   Ad5/fib16.seq 989   A A G C C C C G G A A A C T A C C G A A G T C A C T C T C A T T A C C T C C C C   Ad16 genbank.seq
1001  A A G C C C C G G A A A C T A C C G A A G T C A C T C T C A T T A C C T C C C C   Ad5/fib16.seq 1029  C T T C T T T T T T T C T T A T A T C A G A G A A G A T G A C T G A             Ad16 genbank.seq
1041  C T T C T T T T T T T C T T A T A T C A G A G A A G A T G A C T G A             Ad5/fib16.seq
```

Decoration 'Decoration #1': Box residues that differ from Ad16 genbank.seq.

Figure 9B

Alignment Report of Untitled, using Clustal method with PAM250 residue weight table.
Thursday, November 19, 1998 18:09

```
1   M A K R A R L S S - S F N P V Y P Y E D E S S S Q H P F I N    Ad16 fiber protein GenBank
1   M - K R A R P S E D T F N P V Y P Y E D E S S S Q H P F I N    Ad16A fib protein 30  P G F I S S N G F A Q S P D G V L T L K C V N P L T T A S G    Ad16 fiber protein GenBank
30  P G F I S S N G F A Q S P D G V L T L K C V N P L T T A S G    Ad16A fib protein 60  P L Q L K V G S S L T V D T I D G S L E E N I T A A A P L T    Ad16 fiber protein GenBank
60  P L Q L K V G S S L T V D T I D G S L E E N I T A E A P L T    Ad16A fib protein 90  K T N H S I G L L I G S G L Q T K D D K L C L S L G D G L V    Ad16 fiber protein GenBank
90  K T N H S I G L L I G S G L Q T K D D K L C L S L G D G L V    Ad16A fib protein 120 T K D D K L C L S L G D G L I T K N D V L C A K L G H G L V    Ad16 fiber protein GenBank
120 T K D D K L C L S L G D G L I T K N D V L C A K L G H G L V    Ad16A fib protein 150 F D S S N A I T I E N N T L W T G A K P S A N C V I K E G E    Ad16 fiber protein GenBank
150 F D S S N A I T I E N N T L W T G A K P S A N C V I K E G E    Ad16A fib protein 180 D S P D C K L T L V L V K N G G L I N G Y I T L M G A S E Y    Ad16 fiber protein GenBank
180 D S P D C K L T L V L V K N G G L I N G Y I T L M G A S E Y    Ad16A fib protein 210 T N T L F K N N Q V T I D V N L A F D N T G Q I I T Y L S S    Ad16 fiber protein GenBank
210 T N T L F K N N Q V T I D V N L A F D N T G Q I I T Y L S S    Ad16A fib protein 240 L K S N L N F K D N Q N M A T G T I T S A K G F M P S T T A    Ad16 fiber protein GenBank
240 L K S N L N F K D N Q N M A T G T I T S A K G F M P S T T A    Ad16A fib protein 270 Y P F I T Y A T E T L N E D Y I Y G E C Y Y K S T N G T L F    Ad16 fiber protein GenBank
270 Y P F I T Y A T E T L N E D Y I Y G E C Y Y K S T N G T L F    Ad16A fib protein 300 P L K V T V T L N R R M L A S G M A Y A M N F S W S L N A E    Ad16 fiber protein GenBank
300 P L K V T V T L N R R M L A S G M A Y A M N F S W S L N A E    Ad16A fib protein 330 E A P E T T E V T L I T S P P F F S Y I R E D D .              Ad16 fiber protein GenBank
330 E A P E T T E V T L I T S P P F F S Y I R E D D                Ad16A fib protein
```

Decoration 'Decoration #1': Box residues that differ from the Consensus.

GENE DELIVERY VECTORS PROVIDED WITH A TISSUE TROPISM FOR SMOOTH MUSCLE CELLS, AND/OR ENDOTHELIAL CELLS

CROSS-REFERENCE TO RELATED APPLICATION

This application is a continuation-in-part of pending U.S. patent application Ser. No. 09/348,354, filed on 7 Jul. 1999.

TECHNICAL FIELD

The invention relates to the field of molecular genetics and medicine. In particular the present invention relates to the field of gene therapy more in particular to gene therapy using adenoviruses.

BACKGROUND

In gene therapy, genetic information is usually delivered to a host cell in order to either correct (supplement) a genetic deficiency in said cell, or to inhibit an undesired function in said cell, or to eliminate said host cell. Of course the genetic information can also be intended to provide the host cell with a desired function, e.g. to supply a secreted protein to treat other cells of the host, etc.

Many different methods have been developed to introduce new genetic information into cells. Although many different systems may work on cell lines cultured in vitro, only the group of viral vector mediated gene delivery methods seems to be able to meet the required efficiency of gene transfer in vivo. Thus for gene therapy purposes most of the attention is directed toward the development of suitable viral vectors. Today, most of the attention for the development of suitable viral vectors is directed toward those vectors that are based on adenoviruses. These adenovirus vectors can deliver foreign genetic information very efficiently to target cells in vivo. Moreover, obtaining large amounts of adenovirus vectors is for most types of adenovirus vectors not a problem. Adenovirus vectors are relatively easy to concentrate and purify. Moreover, studies in clinical trials have provided valuable information on the use of these vectors in patients.

There are a lot of reasons for using adenovirus vectors for the delivery of nucleic acid to target cells in gene therapy protocols. However, some characteristics of the current vectors limit their use in specific applications. For instance endothelial cells and smooth muscle cells are not easily transduced by the current generation of adenovirus vectors. For many gene therapy applications, such as applications in the cardiovascular area, preferably these types of cells should be genetically modified. On the other hand, in some applications, even the very good in vivo delivery capacity of adenovirus vectors is not sufficient and higher transfer efficiencies are required. This is the case, for instance, when most cells of a target tissue need to be transduced.

The present invention was made in the course of the manipulation of adenovirus vectors. In the following section therefore a brief introduction to adenoviruses is given.

Adenoviruses

Adenoviruses contain a linear double-stranded DNA molecule of approximately 36000 base pairs. It contains identical Inverted Terminal Repeats (ITR) of approximately 90–140 base pairs with the exact length depending on the serotype. The viral origins of replication are within the ITRs exactly at the genome ends. The transcription units are divided into early and late regions. Shortly after infection the E1A and E1B proteins are expressed and function in transactivation of cellular and adenoviral genes. The early regions E2A and E2B encode proteins (DNA binding protein, pre-terminal protein and polymerase) required for the replication of the adenoviral genome (reviewed in van der Vliet, 1995). The early region E4 encodes several proteins with pleiotropic functions e.g. transactivation of the E2 early promoter, facilitating transport and accumulation of viral mRNAs in the late phase of infection and increasing nuclear stability of major late pre-mRNAs (reviewed in Leppard, 1997). The early region 3 encodes proteins that are involved in modulation of the immune response of the host (Wold et al. 1995). The late region is transcribed from one single promoter (major late promoter) and is activated at the onset of DNA replication. Complex splicing and polyadenylation mechanisms give rise to more than 12 RNA species coding for core proteins, capsid proteins (penton, hexon, fiber and associated proteins), viral protease and proteins necessary for the assembly of the capsid and shut-down of host protein translation (Imperiale, M. J., Akusjnarvi, G. and Leppard, K. N. (1995). Post-transcriptional control of adenovirus gene expression. In: The molecular repertoire of adenoviruses I. P139–171. Doerfler and P. Bohm (eds), Springer-Verlag Berlin Heidelberg).

Interaction Between Virus and Host Cell

The interaction of the virus with the host cell has mainly been investigated with the serotype C viruses Ad2 and Ad5. Binding occurs via interaction of the knob region of the protruding fiber with a cellular receptor. The receptor for Ad2 and Ad5 and probably more adenoviruses is known as the 'Coxsackievirus and Adenovirus Receptor' or CAR protein (Bergelson et al, 1997). Internalization is mediated through interaction of the RGD sequence present in the penton base with cellular integrins (Wickham et al, 1993). This may not be true for all serotypes, for example serotypes 40 and 41 do not contain a RGD sequence in their penton base sequence (Kidd et al, 1993).

The Fiber Protein

The initial step for successful infection is binding of adenovirus to its target cell, a process mediated through fiber protein. The fiber protein has a trimeric structure (Stouten et al, 1992) with different lengths depending on the virus serotype (Sigmas et al, 1985; Kidd et al, 1993). Different serotypes have polypeptides with structurally similar N and C termini, but different middle stem regions. The first 30 amino acids at the N terminus are involved in anchoring of the fiber to the penton base (Chroboczek et al, 1995), especially the conserved FNPVYP region in the tail (Amberg et al, 1997). The C-terminus, or knob, is responsible for initial interaction with the cellular adenovirus receptor. After this initial binding secondary binding between the capsid penton base and cell-surface integrins leads to internalization of viral particles in coated pits and endocytosis (Morgan et al, 1969; Svensson and Persson, 1984; Varga et al, 1991; Greber et al, 1993; Wickham et al, 1993). Integrins are αβ-heterodimers of which at least 14 α-subunits and 8 β-subunits have been identified (Hynes, 1992). The array of integrins expressed in cells is complex and will vary between cell types and cellular environment. Although the knob contains some conserved regions, between serotypes, knob proteins show a high degree of variability, indicating that different adenovirus receptors exist.

Adenoviral Serotypes

At present, six different subgroups of human adenoviruses have been proposed which in total encompass approximately 50 distinct adenovirus serotypes. Besides these human adenoviruses, many animal adenoviruses have been identified (see, e.g. Ishibashi and Yasue, 1984). A serotype is defined on the basis of its immunological distinctiveness as determined by quantitative neutralization with animal antiserum (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al, 1991). The serotypes identified last (42–49) were isolated for the first time from HIV infected patients (Hierholzer et al, 1988; Schnurr et al, 1993). For reasons not well understood, most of such immuno-compromised patients shed adenoviruses that were never isolated from immuno-competent individuals (Hierholzer et al, 1988, 1992; Khoo et al, 1995).

Besides differences towards the sensitivity against neutralizing antibodies of different adenovirus serotypes, adenoviruses in subgroup C such as Ad2 and Ad5 bind to different receptors as compared to adenoviruses from subgroup B such as Ad3 and Ad7 (Defer et al, 1990; Gall et al, 1996). Likewise, it was demonstrated that receptor specificity could be altered by exchanging the Ad3 knob protein with the Ad 5 knob protein, and vice versa (Krasnykh et al, 1996; Stevenson et al. 1995, 1997). Serotypes 2, 4, 5 and 7 all have a natural affiliation towards lung epithelia and other respiratory tissues. In contrast, serotypes 40 and 41 have a natural affiliation towards the gastrointestinal tract. These serotypes differ in at least capsid proteins (penton-base, hexon), proteins responsible for cell binding (fiber protein), and proteins involved in adenovirus replication. It is unknown to what extent the capsid proteins determine the differences in tropism found between the serotypes. It may very well be that post-infection mechanisms determine cell type specificity of adenoviruses. It has been shown that adenoviruses from serotypes A (Ad12 and Ad31), C (Ad2 and Ad5), D (Ad9 and Ad15), E (Ad4) and F (Ad41) all are able to bind labeled, soluble CAR (sCAR) proteins when immobilized on nitrocellulose. Furthermore, binding of adenoviruses from these serotypes to Ramos cells, that express high levels of CAR but lack integrins (Roelvink et al, 1996), could be efficiently blocked by addition of sCAR to viruses prior to infection (Roelvink et al, 1998). However, the fact that (at least some) members of these subgroups are able to bind CAR does not exclude that these viruses have different infection efficiencies in various cell types. For example subgroup D serotypes have relatively short fiber shafts compared to subgroup A and C viruses. It has been postulated that the tropism of subgroup D viruses is to a large extent determined by the penton base binding to integrins (Roelvink et al, 1996; Roelvink et al, 1998). Another example is provided by Zabner et al, 1998 who have tested 14 different serotypes on infection of human ciliated airway epithelia (CAE) and found that serotype 17 (subgroup D) was bound and internalized more efficiently than all other viruses, including other members of subgroup D. Similar experiments using serotypes from subgroup A–F in primary fetal rat cells showed that adenoviruses from subgroup A and B were inefficient whereas viruses from subgroup D were most efficient (Law et al 1998). Also in this case viruses within one subgroup displayed different efficiencies. The importance of fiber binding for the improved infection of Ad17 in CAE was shown by Armentano et al, (WO 98/22609) who made a recombinant LacZ Ad2 virus with a fiber gene from Ad17 and showed that the chimaeric virus infected CAE more efficiently then LacZ Ad2 viruses with Ad2 fibers.

Thus, despite their shared ability to bind CAR, differences in the length of the fiber, knob sequence and other capsid proteins e.g. penton base of the different serotypes may determine the efficiency by which an adenovirus infects a certain target cell. Of interest in this respect is the ability of Ad5 and Ad2 fibers but not of Ad3 fibers to bind to fibronectin III and MHC class 1 $\alpha 2$ derived peptides. This suggests that adenoviruses are able to use cellular receptors other than CAR (Hong et al, 1997). Serotypes 40 and 41 (subgroup F) are known to carry two fiber proteins differing in the length of the shaft. The long shafted 41L fiber is shown to bind to CAR whereas the short shafted 41S is not capable of binding CAR (Roelvink et al, 1998). The receptor for the short fiber is not known.

Adenoviral Gene Delivery Vectors

Most adenoviral gene delivery vectors currently used in gene therapy are derived from the serotype C adenoviruses Ad2 or Ad5. The vectors have a deletion in the E1 region, where novel genetic information can be introduced. The E1 deletion renders the recombinant virus replication defective. It has been demonstrated extensively that recombinant adenovirus, in particular serotype 5 is suitable for efficient transfer of genes in vivo to the liver, the airway epithelium and solid tumors in animal models and human xenografts in immuno-deficient mice (Bout 1996, 1997, Blaese et al, 1995).

Gene transfer vectors derived from adenoviruses (adenoviral vectors) have a number of features that make them particularly useful for gene transfer:

1) the biology of the adenoviruses is well characterized,
2) the adenovirus is not associated with severe human pathology,
3) the virus is extremely efficient in introducing its DNA into the host cell,
4) the virus can infect a wide variety of cells and has a broad host-range,
5) the virus can be produced at high titers in large quantities,
6) and the virus can be rendered replication defective by deletion of the early-region 1 (E1) of the viral genome (Brody and Crystal, 1994).

However, there is still a number of drawbacks associated with the use of adenoviral vectors:

1) Adenoviruses, especially the well investigated serotypes Ad2 and Ad5 usually elicit an immune response by the host into which they are introduced,
2) it is currently not feasible to target the virus to certain cells and tissues,
3) the replication and other functions of the adenovirus are not always very well suited for the cells, which are to be provided with the additional genetic material,
4) the serotypes Ad2 or Ad5, are not ideally suited for delivering additional genetic material to organs other than the liver. The liver can be particularly well transduced with vectors derived from Ad2 or Ad5. Delivery of such vectors via the bloodstream leads to a significant deliver of the vectors to the cells of the liver. In therapies were other cell types then liver cells need to be transduced some means of liver exclusion must be applied to prevent uptake of the vector by these cells. Current methods rely on the physical separation of the vector from the liver cells, most of these methods rely on localizing the vector and/or the target organ via surgery, balloon angioplasty or direct injection into an organ via for instance needles. Liver exclusion is also being practical through delivery of the vector to compartments in the body that are essentially isolated from the bloodstream thereby preventing transport of the vector to the liver. Although these methods mostly succeed in avoiding gross delivery of the vector to the liver, most of the methods are crude and still have considerable leakage and/or have poor target tissue penetration characteristics. In some cases inadvertent delivery of the vector to liver cells can be toxic to the patient. For instance, delivery of a herpes simplex virus (HSV) thymidine kinase (TK) gene for the subsequent killing of dividing cancer cells through administration of gancyclovir is quite dangerous when also a significant amount of liver cells are transduced by the vector. Significant delivery and subsequent expression of the HSV-TK gene to liver cells is associated with severe toxicity. Thus there is a discrete need for an inherently safe vector provided with the property of a reduced transduction efficiency of liver cells.

BRIEF DESCRIPTION OF DRAWINGS

Table I: Oligonucleotides and degenerate oligonucleotides used for the amplification of DNA encoding fiber proteins derived from alternative adenovirus serotypes. (Bold letters represent NdeI restriction site (A–E), NsiI restriction site (1–6, 8) or PacI restriction site (7).

Table II: Biodistribution of chimaeric adenovirus upon intravenous tail vein injection. Values represent luciferase activity/μg of total protein. All values below 200 Relative light units/μg protein are considered background. ND=not determined.

Table III: Expression of CAR and integrins on the cell surface of endothelial cells and smooth muscle cells. 70%: Cells harvested for FACS analysis at a cell density of 70% confluency. 100%: Cells harvested for FACS analysis at a cell density of 100% confluency. PER.C6 cells were taken as a control for antibody staining. Values represent percentages of cells that express CAR or either one of the integrins at levels above background. As background control, HUVECs or HUVsmc were incubated only with the secondary, rat-anti-mouse IgG1-PE labeled antibody.

Table IV: Determination of transgene expression (luciferase activity) per μg of total cellular protein after infection of A549 cells.

Figure 1:
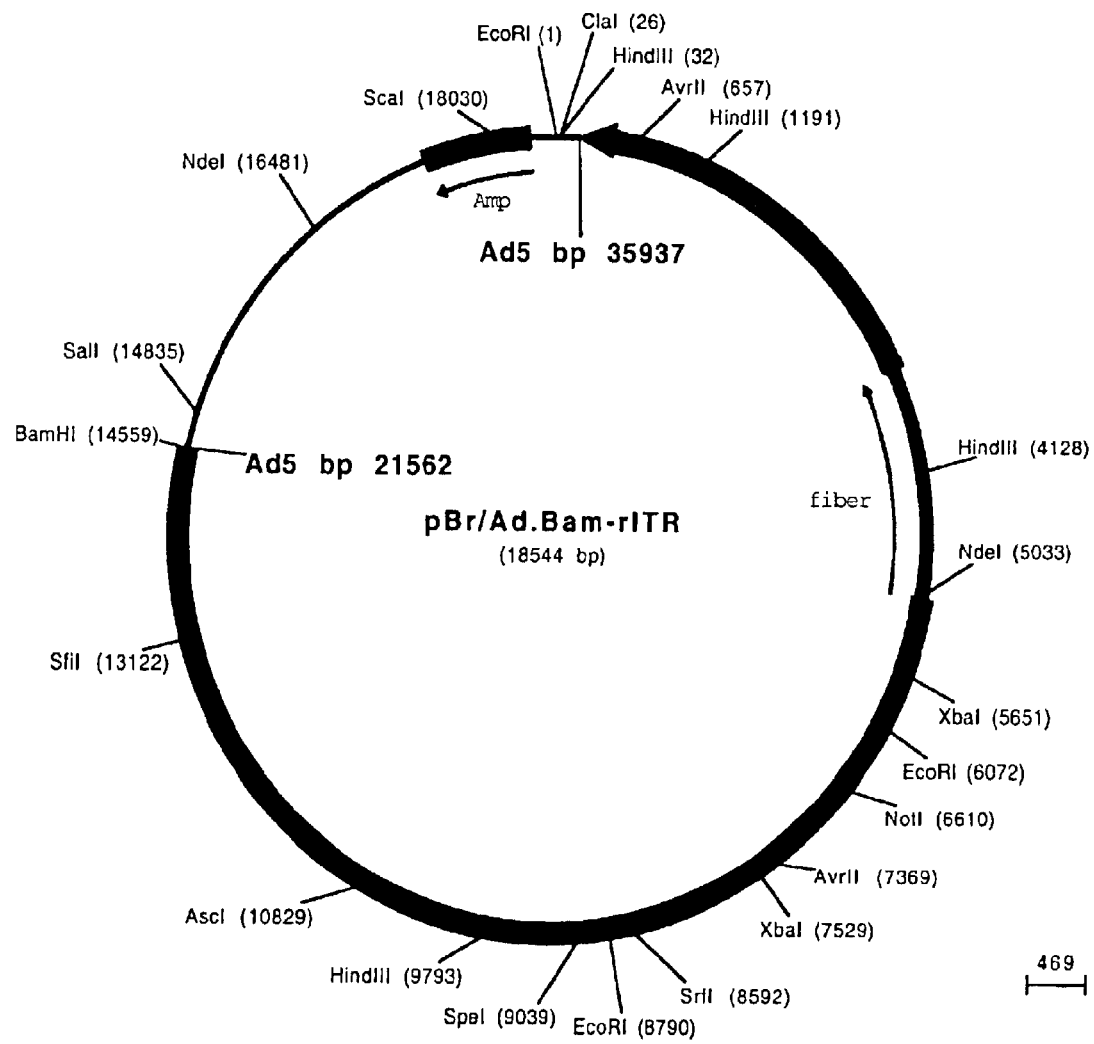

FIG. 1: Schematic drawing of the pBr/Ad.Bam-rITR construct.

Figure 2:
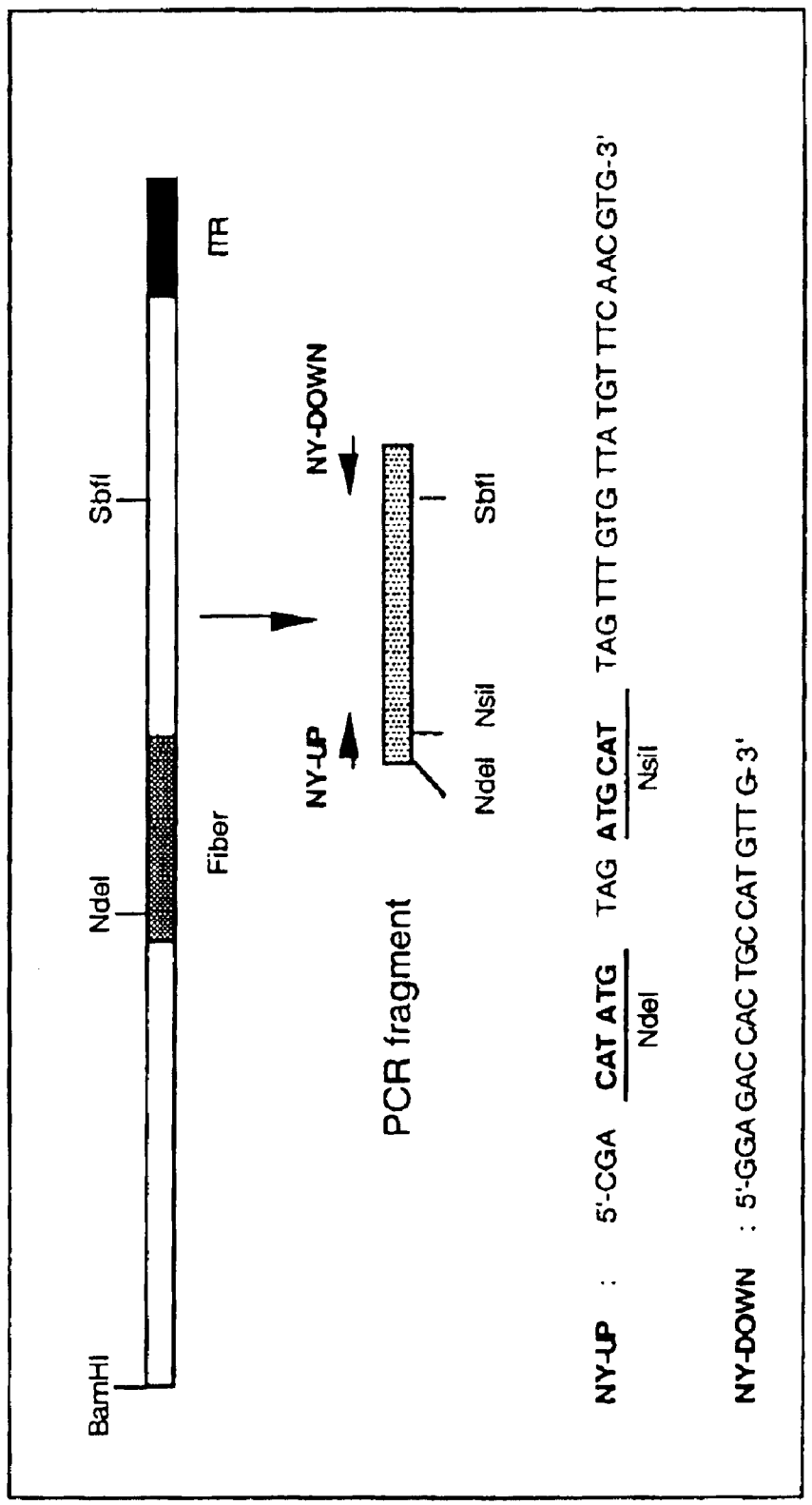

FIG. 2: Schematic drawing of the strategy used to delete the fiber gene from the pBR/Ad.Bam-rITR construct.

Figure 3:
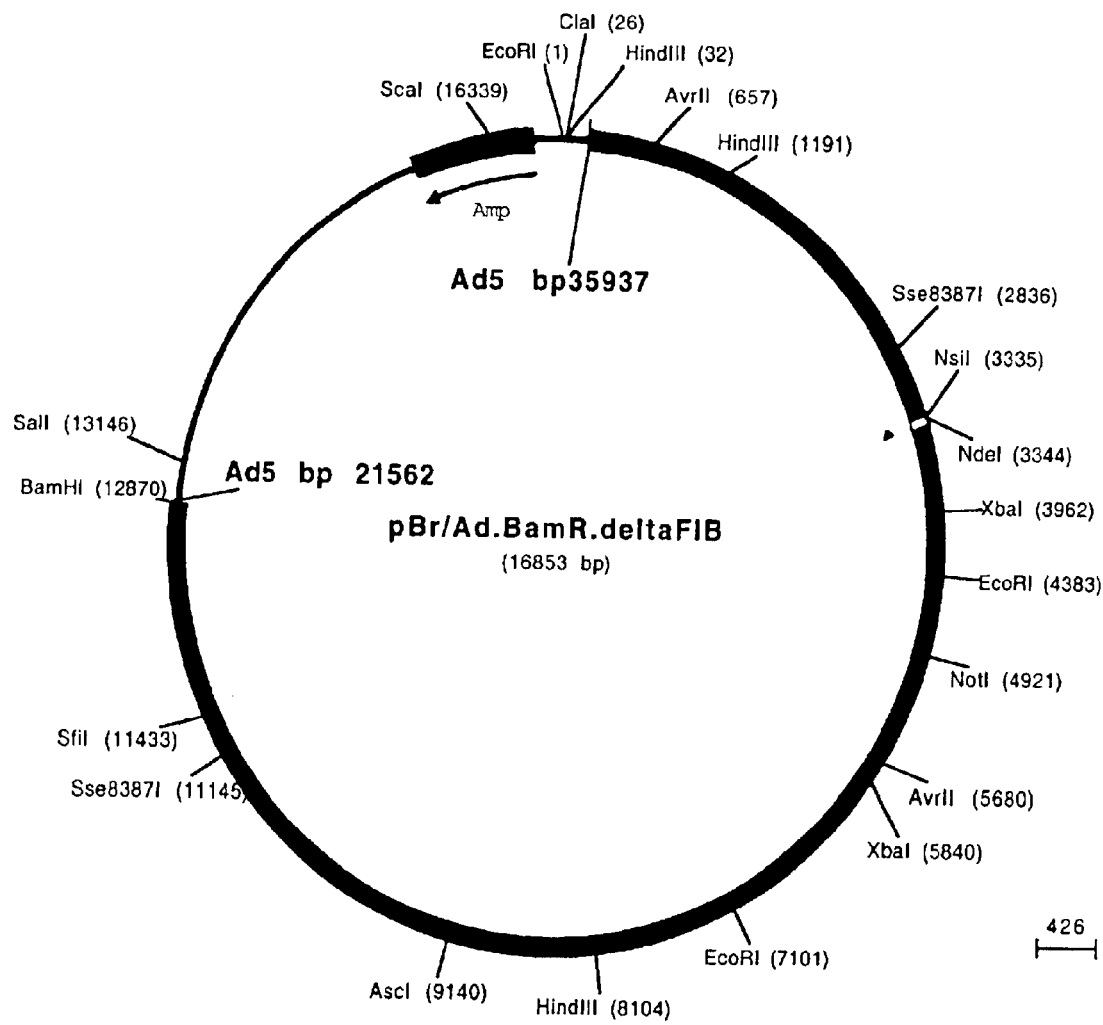

FIG. 3: Schematic drawing of construct pBr/Ad.BamRΔfib (ECACC deposit number 01121708).

FIG. 4: Sequences of the chimaeric fibers Ad5 (SEQ ID NO:16) Ad5/12 (SEQ ID NO:17), Ad5/16 (SEQ ID NO:18), Ad5/28 (SEQ ID NO:19), and Ad5/40-L (SEQ ID NO:20).

Figure 5:
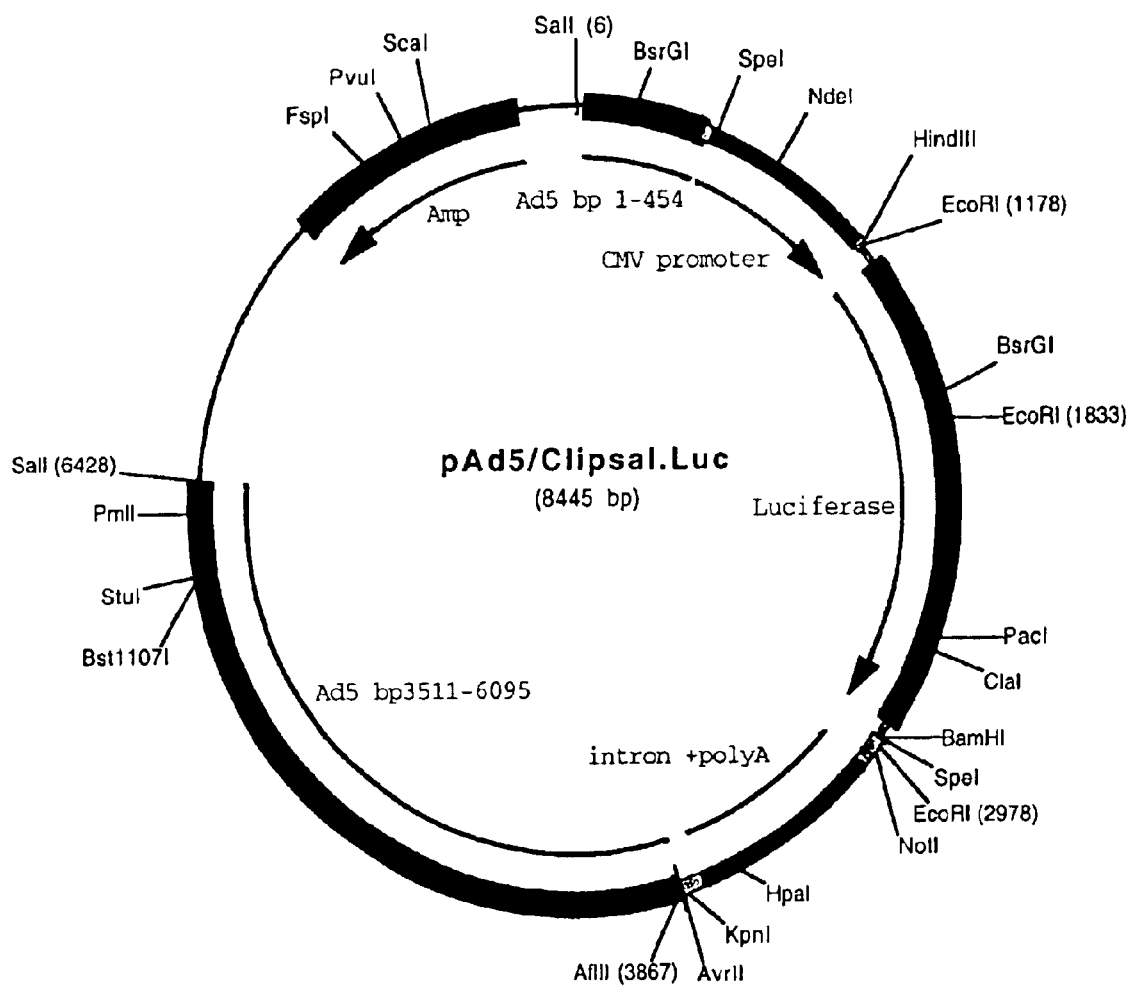

FIG. 5: Schematic drawing of the construct pClipsal-Luc.

FIG. 6: Schematic drawing of the method to generate chimaeric adenoviruses using three overlapping fragments. Early (E) and late regions (L) are indicated. L5 is the fiber coding sequences.

FIG. 7: A) Infection of HUVEC cells using different amounts of virus particles per cell and different fiber chimaeric adenoviruses. Virus concentration: 10000 vp/cell (=white bar), 5000 vp/cell (=grey bar), 2500 vp/cell (=Black bar) 1000 vp/cell (light gray bar, 250 and 50 vp/cell no detectable luciferase activity above background. Luciferase activity is expressed in relative light units (RLU) per microgram of cellular protein. B) Infection of HUVEC cells using different concentrations of cells (22500, 45000, 90000, or 135000 cells seeded per well) and either adenovirus serotype 5 (black bar) or the fiber 16 chimeric adenovirus (white bar). Luciferase activity is expressed in relative light units (RLU) per microgram cellular protein. C) Flow cytometric analysis on Human aorta EC transduced with 500 (Black bar) or 5000 (grey bar) virus particles per cell of Ad5 or the fiber 16 chimeric virus (Fib16). Non-infected cells were used to set the background at 1% and a median fluorescence of 5.4. The maximum shift in the median fluorescence that can be observed on a flow cytometer is 9999. This latter indicates that at 5000 Vp/cell both Ad5 and Fib16 are outside the sensitivity scale of the flow cytometer.

FIG. 8: A) Infection of HUVsmc cells using different amounts of virus particles per cell and different fiber mutant Ad5 based adenoviruses. Virus concentration: 5000 vp/cell (=white bar), 2500 vp/cell (=grey bar), 1250 vp/cell (=dark grey bar) 250 vp/cell (=black bar), or 50 vp/cell (light grey bar). Luciferase activity is expressed as relative light units (RLU) per microgram cellular protein. B) Infection of HUVsmc cells using different concentrations of cells (10000, 20000, 40000, 60000, or 80000 cells per well) and either adenovirus serotype 5 (white bars) or the fiber 16 chimeric adenovirus (black bars). A plateau is observed after infection with chimeric fiber 16 adenovirus due to the fact that transgene expression is higher than the sensitivity range of the bioluminometer used. C) Human umbilical vein SMC transduced with 500 Vp/cell (black bar) or 5000 VP/cell (grey bar) using either Ad5 or the fiber 16 mutant (Fib16). Non-transduced cells were used to set a background median fluorescence of approximately 1. Shown is the median fluorescence of GFP expression as measured by flow cytometry. D) HUVsmc were infected with 312 (light grey bar), 625 (grey bar), 1250 (black bar), 2500 (dark grey bar), 5000 (light grey bar), or 10000 (white bar) virus particles per cell of either the fiber 11, 16, 35, or 51 chimeric virus. Luciferase transgene expression expressed as relative light units (RLU) per microgram protein was measured 48 hours after virus exposure. E) Macroscopic photographs of LacZ staining on saphenous samples. Nuclear targeted LacZ (ntLacZ) yields a deep blue color which appears black or dark grey in non-color prints. F) Macroscopic photographs of LacZ staining on pericard samples. Nuclear targeted LacZ (ntLacZ) gives a deep blue color which appears black in non-color prints. G) Macroscopic photographs of LacZ staining on right coronary artery samples. Nuclear targeted LacZ (ntLacZ) gives a deep blue color which appears black in non-color prints. H) LacZ staining on Left artery descending (LAD) samples. Nuclear targeted LacZ (ntLacZ) gives a deep blue color which appears black in non-color prints.

FIG. 9: Sequences including the gene encoding adenovirus 16 fiber protein as published in Genbank (SEQ ID NO:21) and sequence including a gene encoding a fiber from an adenovirus 16 variant as isolated in the present invention, wherein the sequences of the fiber protein are from the NdeI-site (SEQ ID NO:22). FIG. 9A is a nucleotide sequence comparison (SEQ ID NOS:21 (upper stand) and 22 (lower strand)). FIG. 9B is an amino-acid comparison (SEQ ID NOS:23 (upper strand) and 24 (lower strand)).

SUMMARY OF THE INVENTION

The present invention provides gene therapy methods, compounds and medicines. The present invention is particularly useful in gene therapy applications were endothelial cells and/or smooth muscle cells from the target cell type. The present invention relates to gene delivery vehicles provided with a tissue tropism for at least endothelial cells and/or smooth muscle cells. The present invention further relates to gene delivery vehicles having been deprived of a tissue tropism for liver cells.

DETAILED DESCRIPTION OF THE INVENTION

It is an object of the current invention to provide materials and methods to overcome the limitations of adenoviral vectors mentioned above. In a broad sense, the invention provides new adenoviruses, derived in whole or in part from serotypes different from Ad5. Specific genes of serotypes with preferred characteristics may be combined in a chimaeric vector to give rise to a vector that is better suited for specific applications. Preferred characteristics include, but are not limited to, improved infection of a specific target cell, reduced infection of non-target cells, improved stability of the virus, reduced uptake in antigen presenting cells (APC), or increased uptake in APC, reduced toxicity to target cells, reduced neutralization in humans or animals, reduced or increased CTL response in humans or animals, better and/or prolonged transgene expression, increased penetration capacity in tissues, improved yields in packaging cell lines, etc.

One aspect of the present invention facilitates the combination of the low immunogenicity of some adenoviruses with the characteristics of other adenoviruses that allow efficient gene therapy. Such characteristics may be a high specificity for certain host cells, a good replication machinery for certain cells, a high rate of infection in certain host cells, low infection efficiency in non-target cells, high or low efficiency of APC infection, etc. The invention thus may provide chimaeric adenoviruses having the useful properties of at least two adenoviruses of different serotypes.

Typically, two or more requirements from the above non-exhaustive list are required to obtain an adenovirus capable of efficiently transferring genetic material to a host cell. Therefore, the present invention provides adenovirus vectors which can be used as cassettes to insert different adenoviral genes from different adenoviral serotypes at the required sites. This way one can obtain a vector capable of producing a chimaeric adenovirus, whereby of course also a gene of interest can be inserted (for instance at the site of E1 of the original adenovirus). In this manner the chimaeric adenovirus to be produced can be adapted to the requirements and needs of certain hosts in need of gene therapy for certain disorders. To enable this virus production, a packaging cell will generally be needed in order to produce sufficient amount of safe chimaeric adenoviruses.

In one of its aspects the present invention provides adenoviral vectors comprising at least a fragment of a fiber protein of an adenovirus from subgroup B. Said fiber protein may be the native fiber protein of the adenoviral vector or may be derived from a serotype different from the serotype the adenoviral vector is based on. In the latter case the adenoviral vector according to the invention is a chimaeric adenovirus displaying at least a fragment of the fiber protein derived from subgroup B adenovirus that fragment comprising at least the receptor binding sequence. Typically such a virus will be produced using a vector (typically a plasmid, a cosmid or baculovirus vector). Such vectors are also subject of the present invention. A preferred vector is a vector that can be used to make a chimaeric recombinant virus specifically adapted to the host to be treated and the disorder to be treated.

The present invention also provides a chimaeric adenovirus based on adenovirus type 5 but having at least a fragment of the fiber sequence from adenovirus type 16, whereby the fragment of the fiber of Ad16 comprises the fragment of the fiber protein that is involved in binding a host cell. The present invention also provides chimaeric adenoviral vectors that show improved infection as compared to adenoviruses from other subgroups in specific host cells for example, but not limited to, endothelial cells and smooth muscle cells of human or animal origin. An important feature of the present invention is the means to produce the chimaeric virus. Typically, one does not want an adenovirus batch to be administered to the host cell, which contains replication competent adenovirus. In general therefore it is desired to omit a number of genes (but at least one) from the adenoviral genome on the vector encoding the chimaeric virus and to supply these genes in the genome of the cell in which the vector is brought to produce chimaeric adenovirus. Such a cell is usually called a packaging cell. The invention thus also provides a packaging cell for producing a chimaeric adenovirus according to the invention, comprising in trans all elements necessary for adenovirus production not present on the adenoviral vector according to the invention. Typically vector and packaging cell have to be adapted to one another in that they have all the necessary elements, but that they do not have overlapping elements which lead to replication competent virus by recombination. Thus the invention also provides a kit of parts comprising a packaging cell according to the invention and a recombinant vector according the invention whereby there is essentially no sequence overlap leading to recombination resulting in the production of replication competent adenovirus between said cell and said vector. For certain applications for example when the therapy is aimed at eradication of tumor cells, the adenoviral vector according to the invention may be replication competent or capable of replicating under certain conditions for example in specific cell types like tumor cells or tumor endothelial cells.

It is within the scope of the invention to insert more genes, or a functional part of these genes from the same or other serotypes into the adenoviral vector replacing the corresponding native sequences. Thus for example replacement of (or a functional part of the) fiber sequences with corresponding sequences of other serotypes may be combined with for example replacements of (a functional part of) other capsid genes like penton base or hexon with corresponding sequences of said serotype or of other distinct serotypes. Persons skilled in the art will understand that other combinations not limited to the said genes are possible and are within the scope of the invention. The chimaeric adenoviral vector according to the invention may originate from at least two different serotypes. This may provide the vector with preferred characteristics such as improved infection of target cells and/or less infection of non-target cells, improved stability of the virus, reduced immunogenicity in humans or animals (e.g. reduced uptake in APC, reduced neutralization in the host and/or reduced cytotoxic T-lymphocyte (CTL) response), increased penetration of tissue, better longevity of transgene expression, etc. In this aspect it is preferred to use capsid genes e.g. penton and/or hexon genes from less immunogenic serotypes as defined by the absence or the presence of low amounts of neutralizing antibodies in the vast majority of hosts. It is also preferred to use fiber and/or penton sequences from serotypes that show improved binding and internalization in the target cells. Furthermore it is preferred to delete from the viral vector those genes which lead to expression of adenoviral genes in the target cells. In this aspect a vector deleted of all adenoviral genes is also preferred. Furthermore it is preferred that the promoter driving the gene of interest to be expressed in the target cells is a cell type specific promoter.

In order to be able to precisely adapt the viral vector and provide the chimaeric virus with the desired properties at will, it is preferred that a library of adenoviral genes is provided whereby the genes to be exchanged are located on plasmid- or cosmid-based adenoviral constructs whereby the genes or the sequences to be exchanged are flanked by restriction sites. The preferred genes or sequences can be selected from the library and inserted in the adenoviral constructs that are used to generate the viruses. Typically such a method comprises a number of restriction and ligation steps and transfection of a packaging cell. The adenoviral vector can be transfected in one piece, or as two or more overlapping fragments, whereby viruses are generated by homologous recombination. For example the adenoviral vector may be built up from two or more overlapping sequences for insertion or replacements of a gene of interest in for example the E1 region, for insertion or replacements in penton and/or hexon sequences, and for insertions or replacements into fiber sequences. Thus the invention provides a method for producing chimaeric adenoviruses having one or more desired properties like a desired host range and diminished antigenicity, comprising providing one or more vectors according to the invention having the desired insertion sites, inserting into said vectors at least a functional part of a fiber protein derived from an adenovirus serotype having the desired host range and/or inserting a functional part of a capsid protein derived from an adenovirus serotype having relatively low antigenicity and transfecting said vectors in a packaging cell according to the invention and allowing for production of chimaeric viral particles. Of course other combinations of other viral genes originating from different serotypes can also be inserted as disclosed herein before. Chimaeric viruses having only one non-native sequence in addition to an insertion or replacement of a gene of interest in the E1 region, are also within the scope of the invention.

An immunogenic response to adenovirus that typically occurs is the production of neutralizing antibodies by the host. This is typically a reason for selecting a capsid protein like penton, hexon and/or fiber of a less immunogenic serotype.

Of course it may not be necessary to make chimaeric adenoviruses which have complete proteins from different serotypes. It is well within the skill of the art to produce chimaeric proteins, for instance in the case of fiber proteins it is very well possible to have the base of one serotype and the shaft and the knob from another serotype. In this manner it becomes possible to have the parts of the protein responsible for assembly of viral particles originate from one serotype, thereby enhancing the production of intact viral particles. Thus the invention also provides a chimaeric adenovirus according to the invention, wherein the hexon, penton, fiber and/or other capsid proteins are chimaeric proteins originating from different adenovirus serotypes. Besides generating chimaeric adenoviruses by swapping entire wild type capsid (protein) genes etc. or parts thereof, it is also within the scope of the present invention to insert capsid (protein) genes etc. carrying non-adenoviral sequences or mutations such as point mutations, deletions, insertions, etc. which can be easily screened for preferred characteristics such as temperature stability, assembly, anchoring, redirected infection, altered immune response etc. Again other chimaeric combinations can also be produced and are within the scope of the present invention.

It has been demonstrated in mice and rats that upon in vivo systemic delivery of recombinant adenovirus of common used serotypes for gene therapy purposes more than 90% of the virus is trapped in the liver (Herz et al, 1993; Kass-Eisler et al, 1994; Huard et al, 1995). It is also known that human hepatocytes are efficiently transduced by adenovirus serotype 5 vectors (Castell, J. V., Hernandez, D. Gomez-Foix, A. M., Guillen, I, Donato, T. and Gomez-Lechon, M. J. (1997). Adenovirus-mediated gene transfer into human hepatocytes: analysis of the biochemical functionality of transduced cells. Gene Ther. 4 (5), p455–464). Thus in vivo gene therapy by systemic delivery of Ad2 or Ad5 based vectors is seriously hampered by the efficient uptake of the viruses in the liver leading to unwanted toxicity and less virus being available for transduction of the target cells. Therefore, alteration of the adenovirus serotype 5 host cell range to be able to target other organs in vivo is a major interest of the invention.

To obtain re-directed infection of recombinant adenovirus serotype 5, several approaches have been or still are under investigation. Wickham et al have altered the RGD (Arg, Gly, Asp) motif in the penton base which is believed to be responsible for the $\alpha_v\beta_3$ and $\alpha_v\beta_5$ integrin binding to the penton base. They have replaced this RGD motif by another peptide motif which is specific for the $\alpha_4\beta_3$ receptor. In this way targeting the adenovirus to a specific target cell could be accomplished (Wickham et al, 1995). Krasnykh et al (1998) have made use of the HI loop available in the knob. This loop is, based on X-ray crystallography, located on the outside of the knob trimeric structure and therefore is thought not to contribute to the intramolecular interactions in the knob. Insertion of a FLAG coding sequence into the HI loop resulted in fiber proteins that were able to trimerise and it was further shown that viruses containing the FLAG sequence in the knob region could be made. Although interactions of the FLAG-containing knob with CAR are not changed, insertion of ligands in the HI loop may lead to retargeting of infection. Although successful introduction of changes in the adenovirus serotype 5 fiber and penton-base have been reported, the complex structure of knob and the limited knowledge of the precise amino acids interacting with CAR render such targeting approaches laborious and difficult. The use of antibodies binding to CAR and to a specific cellular receptor has also been described (Wickham et al, 1996; Rogers et al, 1997). This approach is however limited by the availability of specific antibody and by the complexity of the gene therapy product.

To overcome the limitations described above we used pre-existing adenovirus fibers, penton base proteins, hexon proteins or other capsid proteins derived from other adenovirus serotypes. By generating chimaeric adenovirus serotype 5 libraries containing structural proteins of alternative adenovirus serotypes, we have developed a technology, which enables rapid screening for a recombinant adenoviral vector with preferred characteristics.

It is an object of the present invention to provide methods for the generation of chimaeric capsids which can be targeted to specific cell types in vitro as well as in vivo, and thus have an altered tropism for certain cell types. It is a further object of the present invention to provide methods and means by which an adenovirus or an adenovirus capsid can be used as a protein or nucleic acid delivery vehicle to a specific cell type or tissue.

The generation of chimaeric adenoviruses based on adenovirus serotype 5 with modified late genes is described. For this purpose, three plasmids, which together contain the complete adenovirus serotype 5 genome, were constructed. From one of these plasmids part of the DNA encoding the adenovirus serotype 5 fiber protein was removed and replaced by linker DNA sequences that facilitate easy cloning. This plasmid subsequently served as template for the insertion of DNA encoding fiber protein derived from different adenovirus serotypes. The DNA sequences derived from the different serotypes were obtained using the polymerase chain reaction technique in combination with (degenerate) oligonucleotides. At the former E1 location in the genome of adenovirus serotype 5, any gene of interest can be cloned. A single transfection procedure of the three plasmids together results in the formation of a recombinant chimaeric adenovirus. Alternatively, cloning of the sequences obtained from the library of genes can be such that the chimaeric adenoviral vector is built up from one or two fragments. For example one construct contains at least the left ITR and sequences necessary for packaging of the virus, an expression cassette for the gene of interest and sequences overlapping with the second construct comprising all sequences necessary for replication and virus formation not present in the packaging cell as well as the non-native sequences providing the preferred characteristics. This new technology of libraries consisting of chimaeric adenoviruses thus allows for a rapid screening improved recombinant adenoviral vectors for in vitro and in vivo gene therapy purposes.

The use of adenovirus type 5 for in vivo gene therapy is limited by the apparent inability to infect certain cell types e.g. human endothelial cells and smooth muscle cells and the preference of infection of certain organs e.g. liver and spleen. Specifically, this has consequences for treatment of cardiovascular diseases like restenosis and pulmonary hypertension. Adenovirus-mediated delivery of human ceNOS (constitutive endothelial nitric oxide synthase) has been proposed as treatment for restenosis after percutaneous transluminal coronary angioplasty (PTCA). Restenosis is characterized by progressive arterial remodeling, extracellular matrix formation and intimal hyperplasia at the site of angioplasty (Schwartz et al, 1993; Carter et al, 1994; Shi et al, 1996). NO is one of the vasoactive factors shown to be lost after PTCA-induced injury to the endothelial barrier (Lloyd Jones and Bloch, 1996). Thus restoration of NO levels after balloon-induced injury by means of adenoviral delivery of ceNOS may prevent restenosis (Varenne et al, 1998). Other applications for gene therapy whereby the viruses or chimaeric viruses according to the invention are superior to Ad2 or Ad5 based viruses, given as non-limiting examples, are production of proteins by endothelial cells that are secreted into the blood, treatment of hypertension, preventive treatment of stenosis during vein grafting, angiogenesis, heart failure, renal hypertension and others.

In one embodiment this invention describes adenoviral vectors that are, amongst others, especially suited for gene delivery to endothelial cells and smooth muscle cells important for treatment of cardiovascular disorders. The adenoviral vectors preferably are derived from subgroup B adenoviruses or contain at least a functional part of the fiber protein from an adenovirus from subgroup B comprising at least the cell-binding moiety of the fiber protein. In a further preferred embodiment the adenoviral vectors are chimaeric vectors based on adenovirus type 5 and contain at least a functional part of the fiber protein from adenovirus type 16.

In another embodiment this invention provides adenoviral vectors or chimaeric adenoviral vectors that escape the liver following systemic administration. Preferably these adenoviral vectors are derived from subgroup A, B, D, or F in particular serotypes 12, 16, 28 and 40 or contain at least the cell-binding moiety of the fiber protein derived from said adenoviruses.

It is to be understood that in all embodiments the adenoviral vectors may be derived from the serotype having the desired properties or that the adenoviral vector is based on an adenovirus from one serotype and contains the sequences comprising the desired functions of another serotype, these sequences replacing the native sequences in the said serotype.

In another aspect this invention describes chimaeric adenoviruses and methods to generate these viruses that have an altered tropism different from that of adenovirus serotype 5. For example, viruses based on adenovirus serotype 5 but displaying any adenovirus fiber existing in nature. This chimaeric adenovirus serotype 5 is able to infect certain cell types more efficiently, or less efficiently in vitro and in vivo than the adenovirus serotype 5. Such cells include but are not limited to endothelial cells, smooth muscle cells, dendritic cells, neuronal cells, glial cells, synovical cells, lung epithelial cells, hemopoietic stem cells, monocytic/macrophage cells, tumor cells, skeletal muscle cells, mesothelial cells, synoviocytes, etc.

In another aspect the invention describes the construction and use of libraries consisting of distinct parts of adenovirus serotype 5 in which one or more genes or sequences have been replaced with DNA derived from alternative human or animal serotypes. This set of constructs, in total encompassing the complete adenovirus genome, allows for the construction of unique chimaeric adenoviruses customized for a certain disease, group of patients or even a single individual.

In all aspects of the invention the chimaeric adenoviruses may, or may not, contain deletions in the E1 region and insertions of heterologous genes linked either or not to a promoter. Furthermore, chimaeric adenoviruses may, or may not, contain deletions in the E3 region and insertions of heterologous genes linked to a promoter. Furthermore, chimaeric adenoviruses may, or may not, contain deletion in the E2 and/or E4 region and insertions of heterologous genes linked to a promoter. In the latter case E2 and/or E4 complementing cell lines are required to generate recombinant adenoviruses. In fact any gene in the genome of the viral vector can be taken out and supplied in trans. Thus, in the extreme situation, chimaeric viruses do not contain any adenoviral genes in their genome and are by definition minimal adenoviral vectors. In this case all adenoviral functions are supplied in trans using stable cell lines and/or transient expression of these genes. A method for producing minimal adenoviral vectors is described in WO97/00326 and is taken as reference herein. In another case Ad/AAV chimaeric molecules are packaged into the adenovirus capsids of the invention. A method for producing Ad/AAV chimaeric vectors is described in EP 1 042 494 and is taken as reference herein. In principle any nucleic acid may be provided with the adenovirus capsids of the invention.

In one embodiment the invention provides a gene delivery vehicle having been provided with at least a tissue tropism for smooth muscle cells and/or endothelial cells. In another embodiment the invention provides a gene delivery vehicle deprived of a tissue tropism for at least liver cells. Preferably, said gene delivery vehicle is provided with a tissue tropism for at least smooth muscle cells and/or endothelial cells and deprived of a tissue tropism for at least liver cells. In a preferred embodiment of the invention said gene delivery vehicle is provided with a tissue tropism for at least smooth muscle cells and/or endothelial cells and/or deprived of a tissue tropism for at least liver cells using a fiber protein derived from a subgroup B adenovirus, preferably of adenovirus 16. In a preferred aspect of the invention and gene delivery vehicle comprises a virus capsid.

Preferably said virus capsid comprises a virus capsid derived in whole or in part from an adenovirus of subgroup B, preferably from adenovirus 16, or it comprises proteins, or parts thereof, from an adenovirus of subgroup B, preferably of adenovirus 16. In preferred embodiment of the invention said virus capsid comprises proteins, or fragments thereof, from at least two different viruses, preferably adenoviruses. In a preferred embodiment of this aspect of the invention at least one of said virus is an adenovirus of subgroup B, preferably adenovirus 16.

In a preferred embodiment of the invention said gene delivery vehicle comprises an adenovirus fiber protein or fragments thereof. Said fiber protein is preferably derived from an adenovirus of subgroup B, preferably adenovirus 16. Said gene delivery vehicle may further comprise other fiber proteins, or fragments thereof, from other adenoviruses. Said gene delivery vehicle may or may not comprise other adenovirus proteins. Nucleic acid may be linked directly to fiber proteins, or fragments thereof, but may also be linked indirectly. Examples of indirect linkages include but are not limited to, packaging of nucleic acid into adenovirus capsids or packaging of nucleic acid into liposomes, wherein a fiber protein, or a fragment thereof, is incorporated into an adenovirus capsid or linked to a liposome. Direct linkage of nucleic acid to a fiber protein, or fragment thereof, may be performed when said fiber protein, or a fragment thereof, is not part of a complex or when said fiber protein or a fragment thereof, is part of a complex, such as an adenovirus capsid.

In one embodiment of the invention is provided a gene delivery vehicle comprising an adenovirus fiber protein wherein said fiber protein comprises a tissue determining fragment of an adenovirus of subgroup B adenovirus preferably of adenovirus 16. Adenovirus fiber protein comprises three functional domains. One domain, the base, is responsible for anchoring the fiber to a penton base of the adenovirus capsid. Another domain, the knob, is responsible for receptor recognition whereas the shaft domain functions as a spacer separating the base from the knob. The different domains may also have other function. For instance, the shaft is presumably also involved in target cell specificity. Each of the domains mentioned above may be used to define a fragment of a fiber. However, fragments may also be identified in another way. For instance the knob domain comprises of a receptor binding fragment and a shaft binding fragment. The base domain comprises of a penton base binding fragment and a shaft binding fragment. Moreover, the shaft comprises of repeated stretches of amino acids. Each of these repeated stretches may be a fragment.

A tissue tropism determining fragment of a fiber protein may be a single fragment of a fiber protein or a combination of fragments of at least one fiber protein, wherein said tissue tropism determining fragment, either alone or in combination with a virus capsid, determines the efficiency with which a gene delivery vehicle can transduce a given cell or cell type, preferably but not necessarily in a positive way. With a tissue tropism for liver cells is meant a tissue tropism for cells residing in the liver, preferably liver parenchyma cells.

A tissue tropism for a certain tissue may be provided by increasing the efficiency with which cells of said tissue are transduced, alternatively, a tissue tropism for a certain tissue may be provided by decreasing the efficiency with which other cells than the cells of said tissue are transduced.

Fiber proteins possess tissue tropism determining properties. The most well described fragment of the fiber protein involved in tissue tropism is the knob domain. However, the shaft domain of the fiber protein also possesses tissue tropism determining properties. However, not all of the tissue tropism determining properties of an adenovirus capsid are incorporated into a fiber protein.

In a preferred embodiment of the invention, a fiber protein derived from a subgroup B adenovirus, preferably adenovirus 16, is combined with the non-fiber capsid proteins from an adenovirus of subgroup C, preferably of adenovirus 5.

In one aspect of the invention is provided a gene delivery vehicle comprising a nucleic acid derived from an adenovirus. In a preferred embodiment of the invention said adenovirus nucleic acid comprises at least one nucleic acid sequence encoding a fiber protein comprising at least a tissue tropism determining fragment of a subgroup B adenovirus fiber protein, preferably of adenovirus 16. In a preferred aspect said adenovirus comprises nucleic acid from at least two different adenoviruses. In a preferred aspect said adenovirus comprises nucleic acid from at least two different adenoviruses wherein at least one nucleic acid sequence encoding a fiber protein comprising at least a tissue tropism determining fragment of a subgroup B adenovirus fiber protein, preferably of adenovirus 16.

In a preferred embodiment of the invention said adenovirus nucleic acid is modified such that the capacity of said adenovirus nucleic acid to replicate in a target cell has been reduced or disabled. This may be achieved through inactivating or deleting genes encoding early region 1 proteins.

In another preferred embodiment said adenovirus nucleic acid is modified such that the capacity of a host immune system to mount an immune response against adenovirus proteins encoded by the adenovirus nucleic acid has been reduced or disabled. This may be achieved through deletion of genes encoding proteins or early region 2, and/or early region 4. Alternatively, genes encoding early region 3 proteins, may be deleted, or on the contrary, considering the anti-immune system function of some of the proteins encoded by the genes in early region 3, the expression of early region 3 proteins may be enhanced for some purposes. Also, the adenovirus nucleic acid may be altered by a combination of two or more of the specific alterations of the adenovirus nucleic acid mentioned above. It is clear that when essential genes are deleted from the adenovirus nucleic acid, the genes must be complemented in the cell that is going to produce the adenovirus nucleic acid, the adenovirus vector, the vehicle or the chimaeric capsid. The adenovirus nucleic acid may also be modified such that the capacity of a host immune system to mount an immune response against adenovirus proteins encoded by said adenovirus nucleic acid has been reduced or disabled, in other ways then mentioned above, for instance through exchanging capsid proteins, or fragments thereof, by capsid proteins, or fragments thereof, from other serotypes for which humans do not have, or have low levels of, neutralizing antibodies. Another example of this is the exchange of genes encoding capsid proteins with the genes encoding for capsid proteins from other serotypes. Also capsid proteins, or fragments thereof, may be exchanged for other capsid proteins, or fragments thereof, for which individuals are not capable of, or have a low capacity of, raising an immune response against.

An adenovirus nucleic acid may be altered further or instead of one or more of the alterations mentioned above, by inactivating or deleting genes encoding adenovirus late proteins such as but not-limited to, hexon, penton, fiber and/or protein IX.

In a preferred embodiment of the invention all genes encoding adenovirus proteins are deleted from said adenovirus nucleic acid, turning said nucleic acid into a minimal adenovirus vector.

In another preferred embodiment of the invention and adenovirus nucleic acid is an Ad/AAV chimaeric vector, wherein at least the integration means of an adenoassociated virus (AAV) are incorporated into said adenovirus nucleic acid.

In a preferred embodiment of the invention, a vector or a nucleic acid, which may be one and the same or not, according to the invention further comprises at least one non-adenovirus gene. Preferably, at least one of said non-adenovirus gene is selected from the group of genes encoding: an apolipoprotein, a ceNOS, a herpes simplex virus thymidine kinase, an interleukin-3, an interleukin-1α, an (anti) angiogenesis protein such as angiostatin, an anti-proliferation protein, a vascular endothelial growth factor (VGAF), a basic fibroblast growth factor (bFGF), a hypoxia inducible factor 1α (HIF-1α), a PAI-1 and a smooth muscle cell anti-migration protein.

In another aspect, the invention provides a cell for the production of a gene delivery vehicle provided with at least a tissue tropism for smooth muscle cells and/or endothelial cells. In another aspect, the invention provides a cell for the production of a gene delivery vehicle deprived of at least a tissue tropism for liver cells. In another aspect, the invention provides a cell for the production of a gene delivery vehicle provided with at least a tissue tropism for smooth muscle cells and/or endothelial cells and deprived of at least a tissue tropism for liver cells. In a preferred embodiment of the invention said cell is an adenovirus packaging cell, wherein an adenovirus nucleic acid is packaged into an adenovirus capsid. In one aspect of an adenovirus packaging cell of the invention all proteins required for the replication and packaging of an adenovirus nucleic acid, except for the proteins encoded by early region 1, are provided by genes incorporated in said adenovirus nucleic acid. The early region 1 encoded proteins in this aspect of the invention may be encoded by genes incorporated into the cells genomic DNA. In a preferred embodiment of the invention said cell is PER.C6 (ECACG deposit number 96022940). In general, when gene products required for the replication and packaging of adenovirus nucleic acid into adenovirus capsid are not provided by an adenovirus nucleic acid, they are provided by the packaging cell, either by transient transfection, or through stable transformation of said packaging cell. However, a gene product provided by the packaging cell may also be provided by a gene present on said adenovirus nucleic acid. For instance fiber protein may be provided by the packaging cell, for instance through transient transfection, and may be encoded by the adenovirus nucleic acid. This feature can among others be used to generate adenovirus capsids comprising of fiber proteins from two different viruses.

The gene delivery vehicles of the invention are useful for the treatment cardiovascular disease or disease treatable by nucleic acid delivery to endothelial cells or smooth muscle cells. A non-limiting example of the latter is for instance cancer, where the nucleic acid transferred comprises a gene encoding an anti-angiogenesis protein.

The gene delivery vehicles of the invention may be used as a pharmaceutical for the treatment of said diseases. Alternatively, gene delivery vehicles of the invention may be used for the preparation of a medicament for the treatment of said diseases.

In one aspect of the invention provides an adenovirus capsid with or provided with a tissue tropism for smooth muscle cells and/or endothelial cells wherein said capsid preferably comprises proteins from at least two different adenoviruses and wherein at least a tissue tropism determining fragment of a fiber protein is derived from a subgroup B adenovirus, preferably of adenovirus 16. In another aspect the invention provides an adenovirus capsid deprived of a tissue tropism for liver cells wherein said capsid preferably comprises proteins from at least two different adenoviruses and wherein at least a tissue tropism determining fragment of a fiber protein is derived from a subgroup B adenovirus, preferably of adenovirus 16.

In one embodiment the invention comprises the use of an adenovirus capsid, for the delivery of nucleic acid to smooth muscle cells and/or endothelial cells. In another embodiment the invention comprises the use of an adenovirus capsid, for preventing the delivery of nucleic acid to liver cells. The adenovirus capsids of the invention may be used for the treatment cardiovascular disease or disease treatable by nucleic acid delivery to endothelial cells or smooth muscle cells. Example of the latter is for instance cancer where the nucleic acid transferred comprises a gene encoding an anti-angiogenesis protein.

The adenovirus capsids of the invention may be used as a pharmaceutical for the treatment of said diseases. Alternatively, adenovirus capsids of the invention may be used for the preparation of a medicament for the treatment of said diseases.

In another aspect of the invention is provided construct pBr/Ad.BamRΔfib (ECACC deposit number 01121708, deposited on Dec. 12, 2001 with the Centre for Applied Microbiology and Research Authority (European Collection of Animal Cell Cultures), Porton Down, Salisbury, Wiltshire SP4, OJG, United Kingdom, an International Depository Authority, in accordance with the Budapest Treaty comprising adenovirus 5 sequences 21562–31094 and 32794–35938.

In another aspect of the invention is provided construct pBr/AdBamRfib16 (ECACC deposit number 01121710, deposited on Dec. 12, 2001 with the Centre for Applied Microbiology and Research Authority (European Collection of Animal Cell Cultures), Porton Down, Salisbury, Wiltshire SP4, OJG, United Kingdom, an International Depository Authority, in accordance with the Budapest Treaty, comprising adenovirus 5 sequences 21562–31094 and 32794–35938, further comprising an adenovirus 16 gene encoding fiber protein.

In yet another aspect of the invention is provided construct pBr/AdBamR.pac/fib16 (ECACC deposit number 01121709, deposited on Dec. 12, 2001 with the Centre for Applied Microbiology and Research Authority (European Collection of Animal Cell Cultures), Porton Down, Salisbury, Wiltshire SP4, OJG, United Kingdom, an International Depository Authority, in accordance with the Budapest Treaty, comprising adenovirus 5 sequences 21562–31094 and 32794–35938, further comprising an adenovirus 16 gene encoding fiber protein, and further comprising a unique PacI-site in the proximity of the adenovirus 5 right terminal repeat, in the non-adenovirus sequence backbone of the construct.

In another aspect of the invention is provided construct pWE/Ad.AflIIrITRfib16 (ECACC deposit number 01121711, deposited on Dec. 12, 2001 with the Centre for Applied Microbiology and Research Authority (European Collection of Animal Cell Cultures), Porton Down, Salisbury, Wiltshire SP4, OJG, United Kingdom, an International Depository Authority in accordance with the Budapest Treaty comprising Ad5 sequence 3534–31094 and 32794–35938, further comprising an adenovirus 16 gene encoding fiber protein.

In another aspect of the invention is provided construct pWE/Ad.AflIIrITRDE2Afib16 (ECACC deposit number 01121712, deposited on Dec. 12, 2001 with the Centre for Applied Microbiology and Research Authority (European Collection of Animal Cell Cultures), Porton Down, Salisbury, Wiltshire SP4, OJG, United Kingdom, an International Depository Authority, in accordance with the Budapest Treaty comprising Ad5 sequences 3534–22443 and 24033–31094 and 32794–35938, further comprising an adenovirus 16 gene encoding fiber protein.

In the numbering of the sequences mentioned above, the number is depicted until and not until plus.

In a preferred embodiment of the invention said constructs are used for the generation of a gene delivery vehicle or an adenovirus capsid with a tissue tropism for smooth muscle cells and/or endothelial cells.

In another aspect the invention provides a library of adenovirus vectors, or gene delivery vehicles which may be one and the same or not, comprising a large selection of non-adenovirus nucleic acids. In another aspect of the invention, adenovirus genes encoding capsid proteins are used to generate a library of adenovirus capsids comprising of proteins derived from at least two different adenoviruses, said adenoviruses preferably being derived from two different serotypes, wherein preferably one serotype is an adenovirus of subgroup B. In a particularly preferred embodiment of the invention a library of adenovirus capsids is generated comprising proteins from at least two different adenoviruses and wherein at least a tissue tropism determining fragment of fiber protein is derived from an adenovirus of subgroup B, preferably of adenovirus 16.

A fiber protein of adenovirus 16 preferably comprises of the sequence given in FIG. 9. However within the scope of the present invention analogous sequences may be obtained through using codon degeneracy. Alternatively, amino-acid substitutions or insertions or deletions may be performed as long as the tissue tropism determining property is not significantly altered. Such amino-acid substitutions may be within the same polarity group or without.

In the following the invention is illustrated by a number of non-limiting examples.

EXAMPLES

Example 1

Generation of Adenovirus Serotype 5 Based Viruses with Chimaeric Fiber Proteins

Generation of Adenovirus Template Clones Lacking DNA Encoding for Fiber

The fiber coding sequence of adenovirus serotype 5 is located between nucleotides 31042 and 32787. To remove the adenovirus serotype 5 DNA encoding fiber we started with construct pBr/Ad.Bam-rITR (FIG. 1; ECACC deposit P97082122). From this construct first a NdeI site was removed. For this purpose, pBr322 plasmid DNA was digested with NdeI after which protruding ends were filled using Klenow enzyme. This pBr322 plasmid was then re-ligated, digested with NdeI and transformed into E. coli DH5α. The obtained pBr/ΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.BamrITRΔNdeI which hence contained a unique NdeI site. Next a PCR was performed with oligonucleotides "NY-up" and "NY-down" (FIG. 2). During amplification, both a NdeI and NsiI restriction site were introduced to facilitate cloning of the amplified fiber DNAs. Amplification consisted of 25 cycles of each for 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM MgCl$_2$, and 1 unit of Elongase heat stable polymerase (Gibco, The Netherlands). One-tenth of the PCR product was run on an agarose gel which demonstrated that the expected DNA fragment of ±2200 bp was amplified. This PCR fragment was subsequently purified using Geneclean kit system (Bio101 Inc.). Then, both the construct pBr/Ad.Bam-rITRΔNdeI as well as the PCR product were digested with restriction enzymes NdeI and SbfI. The PCR fragment was subsequently cloned using T4 ligase enzyme into the NdeI and SbfI sites thus generating pBr/Ad.BamRΔFib (FIG. 3).

Amplification of Fiber Sequences from Adenovirus Serotypes

To enable amplification of the DNAs encoding fiber protein derived from alternative serotypes degenerate oligonucleotides were synthesized. For this purpose, first known DNA sequences encoding for fiber protein of alternative serotypes were aligned to identify conserved regions in both the tail region as well as the knob region of the fiber protein. From the alignment, which contained the nucleotide sequence of 19 different serotypes representing all 6 subgroups, (degenerate) oligonucleotides were synthesized (see Table I, SEQ ID NOS: 1–13). Also shown in table 3 is the combination of oligonucleotides used to amplify the DNA encoding fiber protein of a specific serotype. The amplification reaction (50 μl) contained 2 mM dNTPs, 25 pmol of each oligonucleotide, standard 1×PCR buffer, 1.5 mM MgCl$_2$, and 1 Unit Pwo heat stable polymerase (Boehringer Mannheim) per reaction. The cycler program contained 20 cycles, each consisting of 30 sec. at 94° C., 60 sec. at 60–64° C., and 120 sec. at 72° C. One-tenth of the PCR product was run on an agarose gel to demonstrate that a DNA fragment was amplified. Of each different template, two independent PCR reactions were performed.

Generation of Chimaeric Adenoviral DNA Constructs

All amplified fiber DNAs as well as the vector (pBr/Ad.BamRΔFib) (ECACC deposit number 01121708) were digested with NdeI and NsiI. The digested DNAs were subsequently run on a agarose gel after which the fragments were isolated from the gel and purified using the Geneclean kit (Bio101 Inc). The PCR fragments were then cloned into the NdeI and NsiI sites of pBr/AdBamRΔFib (ECACC deposit number 01121708), thus generating pBr/AdBamRFibXX (where XX stands for the serotype number of which the fiber DNA was isolated). The inserts generated by PCR were sequenced to confirm correct amplification. The obtained sequences of the different fiber genes are shown in FIG. 4.

Generation of Recombinant Adenovirus Chimaeric for Fiber Protein

To enable efficient generation of chimaeric viruses an AvrII fragment from the pBr/AdBamRFib16 (ECACC deposit number 01121710), pBr/AdBamRFib28, pBr/AdBamRFib40-L constructs was subcloned into the vector pBr/Ad.Bam-rITR.pac#8 (ECACC deposit #P97082121) replacing the corresponding sequences in this vector. pBr/Ad.Bam-rITR.pac#8 has the same adenoviral insert as pBr/Ad.Bam-rITR but has a PacI site near the rITR that enables the ITR to be separated from the vector sequences. The construct pWE/Ad.AflII-Eco was generated as follows. PWE.pac was digested with ClaI and the 5 prime protruding ends were filled in with Klenow enzyme. The DNA was then digested with PacI and isolate from agarose gel. PWE/AflIIrITR was digested with EcoRI and after treatment with Klenow enzyme digested with PacI. The large 24 kb fragment containing the adenoviral sequences was isolated from agarose gel and ligated to the ClaI digested and blunted pWE.Pac vector. Use was made of the ligation express kit from Clontech. After transformation of XL10-gold cells from Stratagene, clones were identified that contained the expected construct. PWE/Ad.AlfII-Eco contains Ad5 sequences from basepairs 3534–27336. Three constructs, pClipsal-Luc (FIG. 5) digested with SalI, pWE/Ad.AflII-Eco digested with PacI and EcoRI and pBr/AdBamR.pac/fibXX digested with BamHI and PacI were transfected into adenovirus producer cells (PER.C6, Fallaux et al, 1998). FIG. 6 schematically depicts the method and fragments used to generate the chimaeric viruses. Only pBr/Ad.BamRfib12 was used without subcloning in the PacI containing vector and therefor was not liberated from vector sequences using PacI but was digested with ClaI which leaves approximately 160 bp of vector sequences attached to the right ITR. Furthermore, the pBr/Ad.BamRfib12 and pBr/Ad.BamRfib28 contain an internal BamHI site in the fiber sequences and were therefor digested with SalI which cuts in the vector sequences flanking the BamHI site. For transfection, 2 µg of pCLIPsal-Luc, and 4 µg of both pWE/Ad.AflII-Eco and pBr/AdBamR.pac/fibXX were diluted in serum free DMEM to 100 µl total volume. To this DNA suspension 100 µl 2.5× diluted lipofectamine (Gibco) in serum-free medium were added. After 30 minutes at room temperature, the DNA-lipofectamine complex solution was added to 2.5 ml of serum-free DMEM which was subsequently added to a T25 cm$^2$ tissue culture flask. This flask contained PER.C6 cells that were seeded 24-hours prior to transfection at a density of 1×10$^6$ cells/flask. Two hours later, the DNA-lipofectamine complex containing medium was diluted once by the addition of 2.5 ml DMEM supplemented with 20% fetal calf serum. Agains 24 hours later the medium was replaced by fresh DMEM supplemented with 10% fetal calf serum. Cells were cultured for 6–8 days, subsequently harvested, and freeze/thawed 3 times. Cellular debris was removed by centrifugation for 5 minutes at 3000 rpm room temperature. Of the supernatant (12.5 ml) 3–5 ml was used to infect again PER.C6 cells (T80 cm$^2$ tissue culture flasks). This re-infection results in full cytopathogenic effect (CPE) after 5–6 days after which the adenovirus is harvested as described above.

Production of Fiber Chimaeric Adenovirus 10 ml of the above described crude lysate was used to inoculate a 1 liter fermentor which contained 1$^7$–1.5×10$^6$ PER.C6 cells/ml growing in suspension. Three days after inoculation, the cells were harvested and pelleted by centrifuging for 10 min at 1750 rpm at room temperature. The chimaeric adenovirus present in the pelleted cells was subsequently extracted and purified using the following downstream processing protocol. The pellet was dissolved in 50 ml 10 mM NaPO$_4$ and frozen at −20° C. After thawing at 37° C., 5.6 ml deoxycholate (5% w/v) was added after which the solution was homogenized. The solution was subsequently incubated for 15 minutes at 37° C. to completely crack the cells. After homogenizing the solution, 1875 µl (1M) MgCl$_2$ was added and 5 ml 100% glycerol. After the addition of 375 µl DNase (10 mg/ml) the solution was incubated for 30 minutes at 37° C. Cell debris was removed by centrifugation at 1880×g for 30 minutes at room temperature without the brake on. The supernatant was subsequently purified from proteins by loading on 10 ml of freon. Upon centrifugation for 15 minutes at 2000 rpm without brake at room temperature three bands are visible of which the upper band represents the adenovirus. This band was isolated by pipetting after which it was loaded on a Tris/HCl (1M) buffered caesiumchloride blockgradient (range: 1.2 to 1.4 gr./ml). Upon centrifugation at 21000 rpm for 2.5 hours at 10° C. the virus was purified from remaining protein and cell debris since the virus, in contrast to the other components, does not migrate into the 1.4 gr./ml caesiumchloride solution. The virus band is isolated after which a second purification using a Tris/HCl (1M) buffered continues gradient of 1.33 gr./ml of caesiumchloride is performed. After virus loading on top of this gradient the virus is centrifuged for 17 hours at 55000 rpm at 10° C. Subsequently the virus bend is isolated and after the addition of 30 µl of sucrose (50 w/v) excess caesiumchloride is removed by three rounds of dialysis, each round comprising of 1 hour. For dialysis the virus is transferred to dialysis slides (Slide-a-lizer, cut off 10000 kDa, Pierce, USA). The buffers used for dialysis are PBS which are supplemented with an increasing concentration of sucrose (round 1 to 3: 30 ml, 60 ml, and 150 ml sucrose (50% w/v)/1.5 liter PBS, all supplemented with 7.5 ml 2% (w/v) CaMgCl$_2$). After dialysis, the virus is removed from the slide-a-lizer after which it is aliquoted in portions of 25 and 100 µl upon which the virus is stored at −85° C. To determine the number of virusparticles per ml, 50 µl of the virus batch is run on an high pressure liquid chromatograph (HPLC) as described by Shamram et al (1997). The virus titers were found to be in the same range as the Ad5.Luc virus batch (Ad5.Luc: 2.2×10$^{11}$ vp/ml; Ad5.LucFib12: 1.3×10$^{11}$ vp/ml; Ad5.LucFib16: 3.1×10$^{12}$ vp/ml; Ad5.LucFib28: 5.4×10$^{10}$ vp/ml; Ad5.LucFib40-L: 1.6×10$^{12}$ vp/ml).

Example 2

Biodistribution of Chimeric Viruses after Intravenous Tail Vein Injection of Rats To investigate the biodistribution of the chimeric adenoviruses carrying fiber 12, 16, 28, or 40-2, 1×10$^{10}$ particles of each of the generated virusbatches was diluted in 1 ml PBS after which the virus was injected in the tail vein of adult male Wag/Rij rats (3 rats/virus). As a control, Ad5 carrying the luciferase transgene was used. Forty-eight hours after the administration of the virus, the rats were sacrificed after which the liver, spleen, lung, kidney, heart, and brain were dissected. These organs were subsequently mixed with 1 ml of lysis buffer (1% Triton X-100/PBS) and minced for 30 seconds to obtain a protein lysate. The protein lysate was subsequently tested for the presence of transgene expression (luciferase activity) and the protein concentration was determined to express the luciferase activity per µg of protein. The results, Shown in Table II, demonstrate that in contrast to the Adenovirus serotype 5 control, none of the fiber chimeras are targeted specifically to the liver or to the spleen. This experiment shows that it is possible to circumvent the uptake of adenoviruses by the liver by making use of fibers of other serotypes. It also shows that the uptake by the liver is not correlated with the length of the fiber shaft, or determined solely by the ability of fiber knob to bind to CAR. The fibers used have different shaft lengths and, except for fiber 16, are derived from subgroups known to have a fiber that can bind CAR (Roelvink et al 1998).

Example 3

Figure 7A:
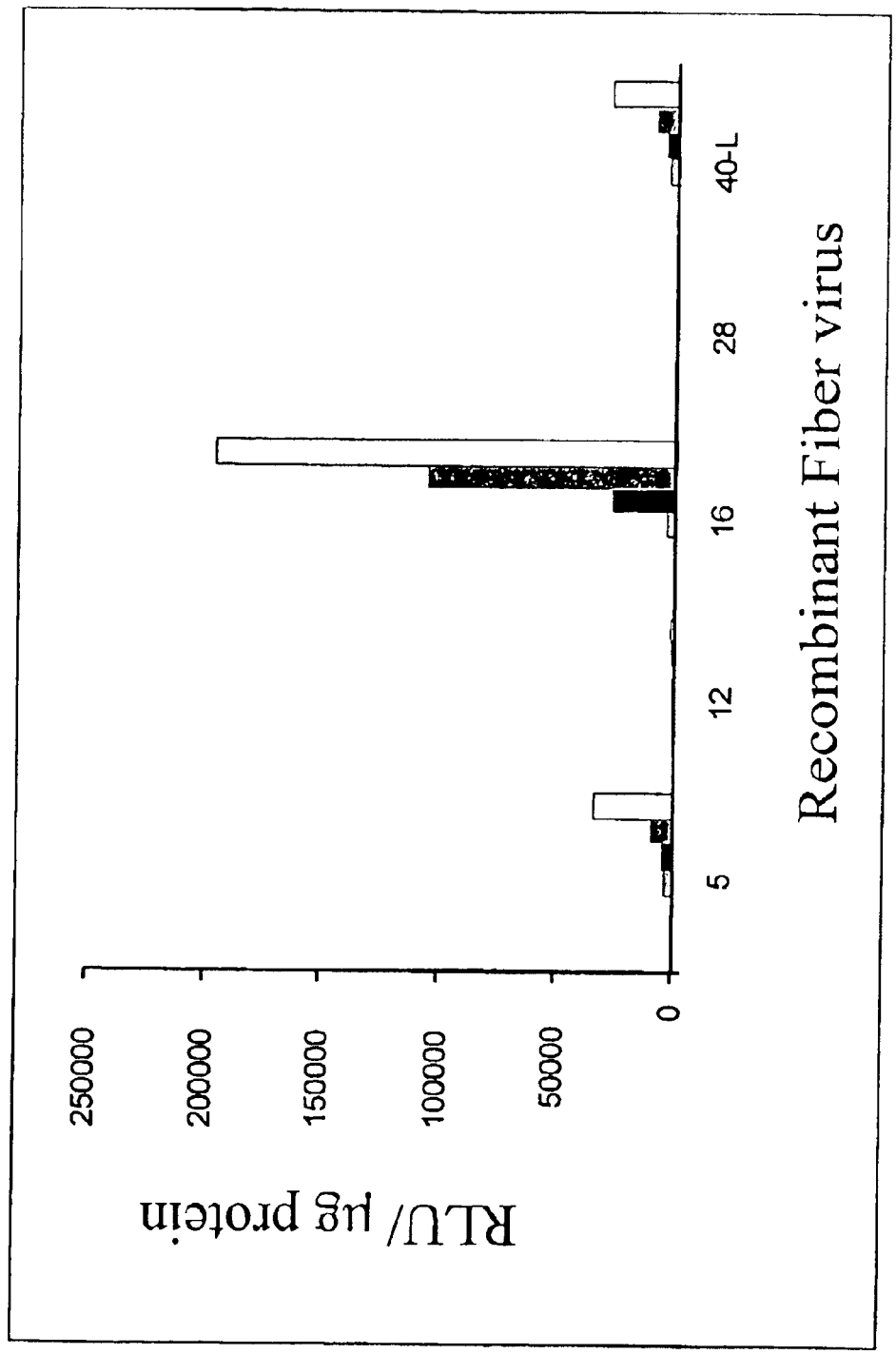
Figure 7B:
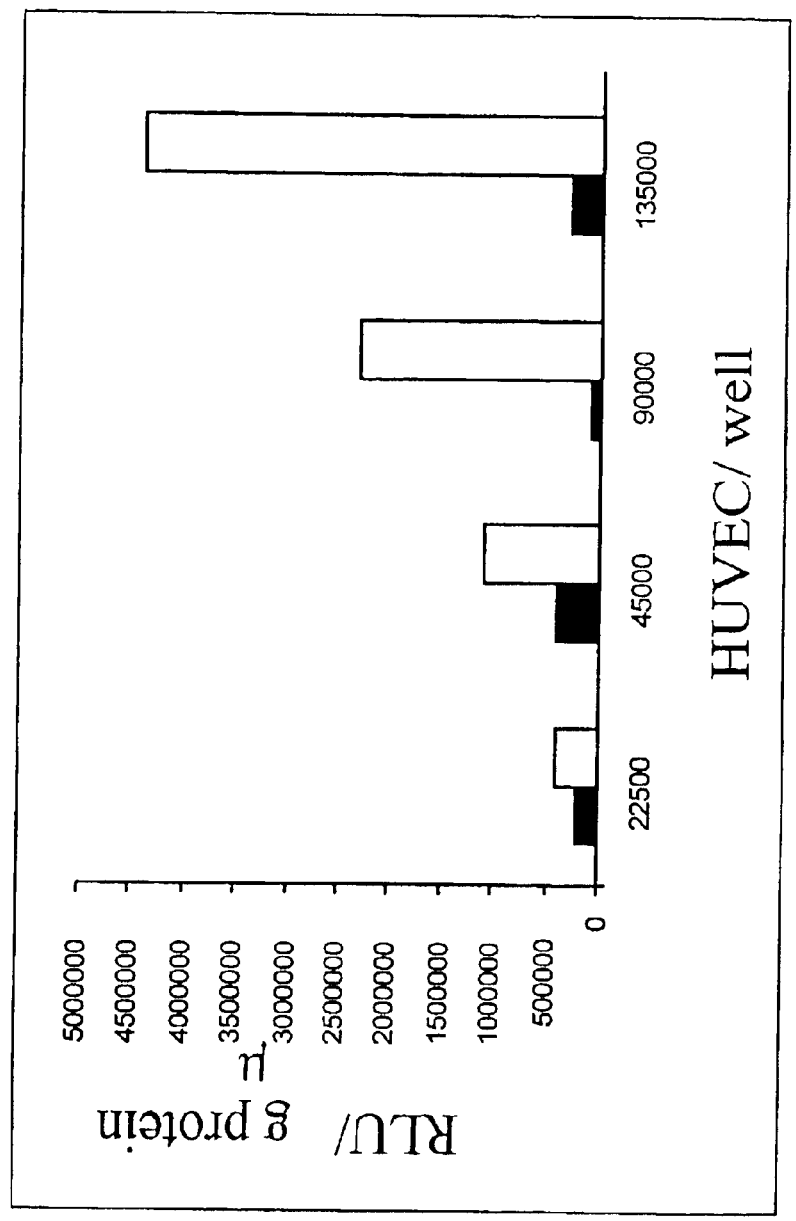
Figure 7C:
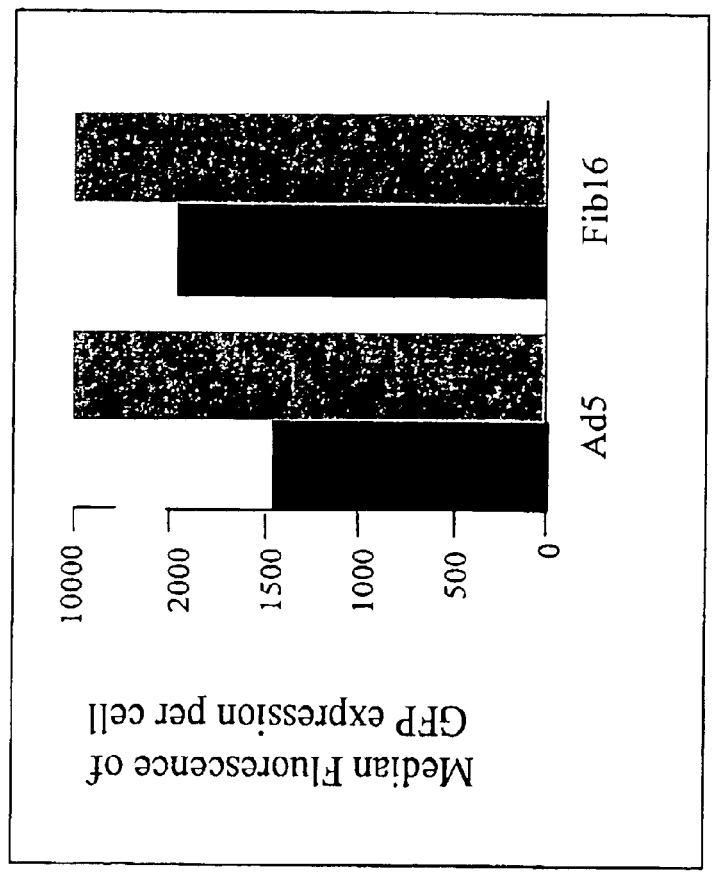

Chimaeric Viruses Display Differences in Endothelial and Smooth Muscle Cell Transduction A) Infection of Human Endothelial Cells Human endothelial cells (HUVEC) were isolated, cultured and characterized as described previously (Jaffe et al 1973; Wijnberg et al 1997). Briefly, cells were cultured on gelatin-coated dishes in M199 supplemented with 20 mM HEPES, pH 7.3 (Flow Labs., Irvine, Scotland), 10% (v/v) human serum (local blood bank), 10% (v/v) heat-inactivated newborn calf serum (NBCS) (GIBCO BRL, Gaithersburg, Md.), 150 µg/ml crude endothelial cell growth factor, 5 U/ml heparin (Leo Pharmaceutics Products, Woesp, The Netherlands), penicillin (100 UJ/ml) /streptomycin (100 µg/ml) (Boehringer Mannheim, Mannheim, FRO) at 37° C. under 5% (v/v) $CO_2$/95% (v/v) air atmosphere. Cells used for experiments were between passage 1–3. In a first set of experiments 40000 HUVEC cells (a pool from 4 different individuals) were seeded in each well of 24-well plates in a total volume of 200 µl. Twenty-four hours after seeding, the cells were washed with PBS after which 200 µl of DMEM supplemented with 2% FCS was added to the cells. This medium contained various amounts of virus (MOI=50, 250, 1000, 2500, 5000, and 10000). The viruses used were besides the control Ad5, the fiber chimeras 12, 16, 28, and 40-L (each infection in triplicate). Two hours after addition of the virus the medium was replaced by normal medium. Again forty-eight hours later cells were washed and lysed by the addition of 100 µl lysisbuffer. In FIG. 7a, results are shown on the transgene expression per microgram total protein after infection of HUVEC cells. These results show that fiber chimeras 12 and 28 are unable to infect HUVEC cells, that 40-L infects HUVECs with similar efficiency as the control Ad5 virus, and that fiber chimera 16 infects HUVECs significantly better. In a next set of experiments (n=8) the fiber 16 chimera was compared with the Ad5.Luc vector on HUVEC for luciferase activity after transduction with 2500 virus particles per cell of each virus. These experiments demonstrated that fiber 16 yields, on average, 8.1 fold increased luciferase activity (SD±4.5) as compared with Ad5. In a next experiment, an equal number of virus particles was added to wells of 24-well plates that contained different HUVEC cell concentrations. This experiment was performed since it is known that HUVECs are less efficiently infected with adenovirus serotype 5 when these cells reach confluency. For this purposes, HUVECs were seeded at 22500, 45000, 90000, and 135000 cells per well of 24-well plates (in triplicate). Twenty-four hours later, these cells were infected as described above with medium containing $4.5 \times 10^9$ virusparticles. The viruses used were, besides the control adenovirus serotype 5, the chimera fiber 16. The result of the transgene expression (RLU) per microgram protein determined 48 hours after infection (see FIG. 7b) shows that the fiber 16 chimaeric adenovirus is also better suited to infect HUVEC cells even when these cells are 100% confluent which better mimics an in vivo situation. Since the Luciferase markergene does not provide information concerning the number of cells infected another experiment was performed with adenovirus serotype 5 and the fiber 16 chimera, both carrying a green fluorescent protein (GFP) as a marker gene. This protein expression can be detected using a flow cytometer which renders information about the percentage of cells transduced as well as fluorescence per cell. In this experiment cells were seeded at a concentration of 40000 cells per well and were exposed to virus for 2 hours. The virus used was Ad5.GFP ($8.4 \times 10^{11}$ vp/ml) and Ad5.Fib16 GFP ($5.1 \times 10^{11}$ vp/ml). Cells were exposed to a virus concentration of 500 virus particles per cell. Flow cytometric analysis, 48 hours after virus exposure demonstrated that the fiber 16 virus gives higher transgene expression levels per cell since the median fluorescence, a parameter identifying the amount of GFP expression per cell, is higher with fiber 16 as compared to Ad5 (FIG. 7c). These results are thus consistent and demonstrate that the fiber 16 chimeric virus is better suited to infect human primary endothelial cells as compared to Ad5.

B) Infection of Human Smooth Muscle Cells

Figure 8A:
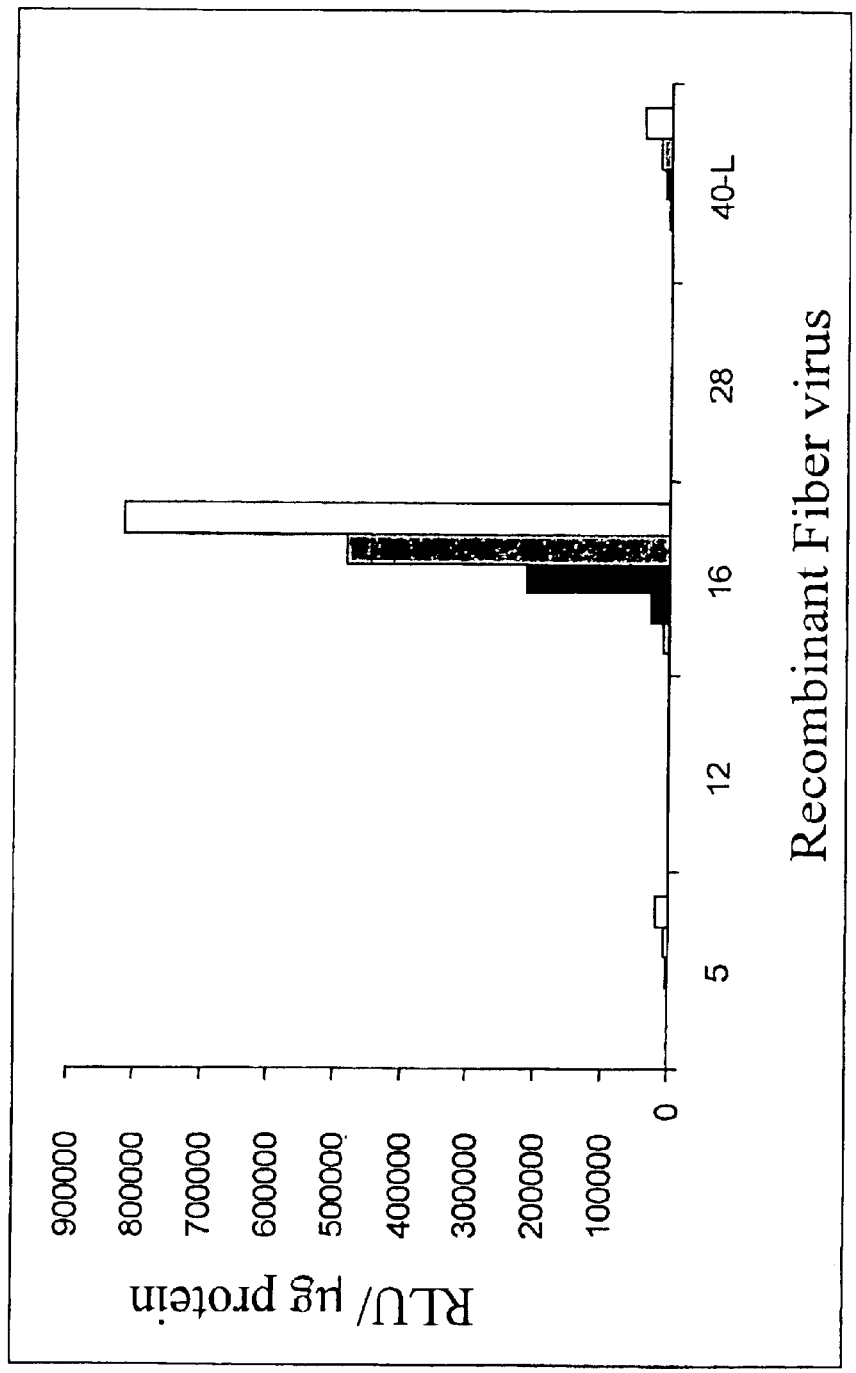
Figure 8B:
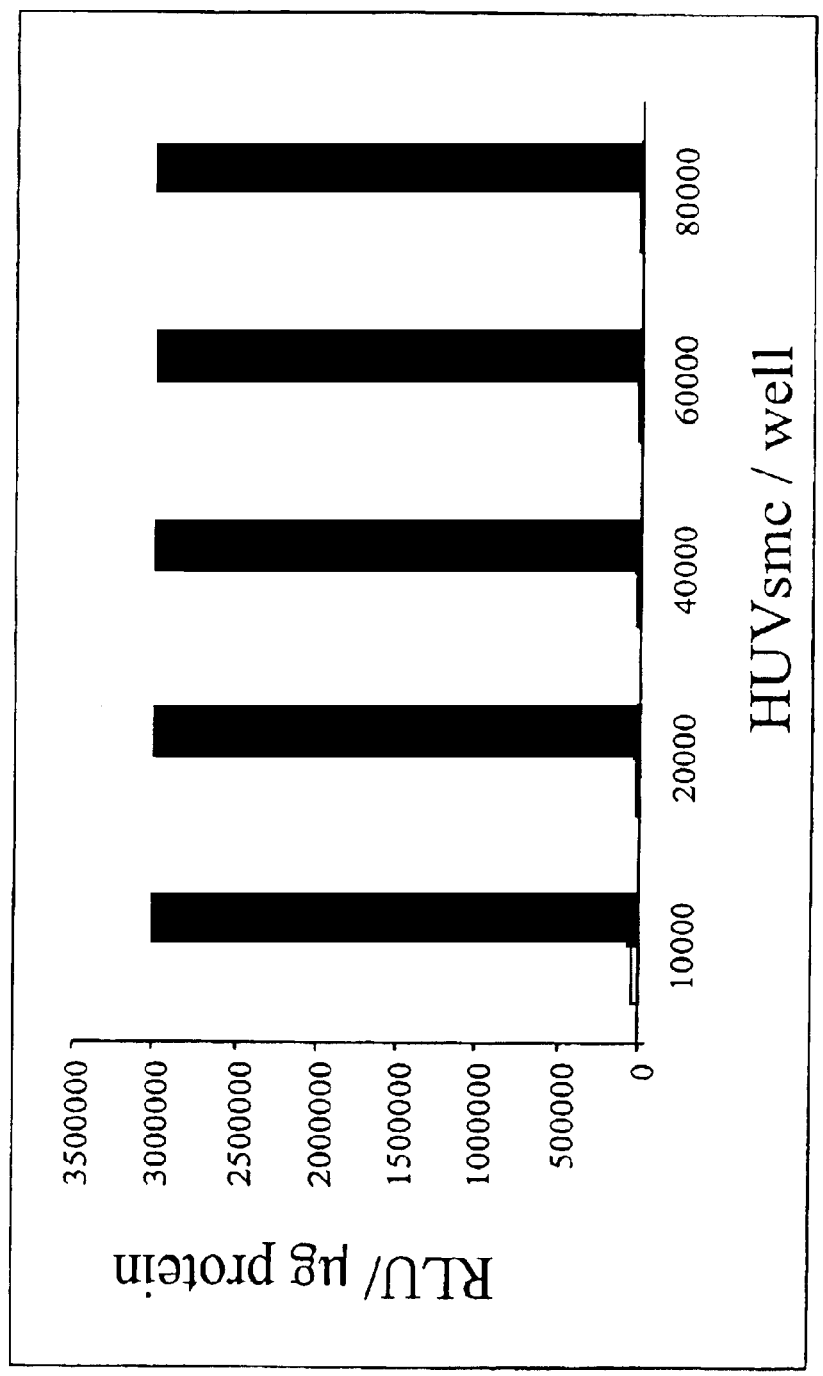

Smooth muscle cells were isolated after isolation of EC (Weinberg et al 1997). The veins were incubated with medium (DMEM) supplemented with penicillin/ streptomycin) containing 0.075% (w/v) collagenase (Worthington Biochemical Corp., Freehold, N.J., USA). After 45 minutes the incubation medium containing detached cells was flushed from the veins. Cells were washed and cultured on gelatin coated dishes in culture medium supplemented with 10% fetal calf serum and 10% human serum at 37° C. under 5% (w/v) $CO_2$/95% (v/v) air atmosphere. Cells used for experiments were between passage 3–6. We first tested the panel of chimeric fiber viruses versus the control adenovirus serotype 5 for the infection of human smooth muscle cells. For this purpose, 40000 human umbilical vein smooth muscle cells (HUVsmc) were seeded in wells of 24-well plates in a total volume of 200 µl. Twenty-four hours after seeding, the cells were washed with PBS after which 200 µl of DMEM supplemented with 2% FCS was added to the cells. This medium contained various amounts of virus (MOI=50, 250, 1250, 2500, and 5000). The viruses used were besides the control Ad5 the fiber chimeras 12, 16, 28, and 40-L (each infection in triplicate). Two hours after addition of the virus the medium was replaced by normal medium. Again forty-eight hours later cells were washed and lysed by the addition of 100 µl lysisbuffer. In FIG. 8a, results are shown of the transgene expression per microgram total protein after infection of HUVsmc cells. These results show that fiber chimeras 12 and 28 are unable to infect HUVsmc cells, that 40-L infects HUVsmc with similar efficiency as the control Ad5 virus, and that fiber chimera 16 infects HUVsmc significantly better. In a next set of experiments, smooth muscle cells derived from saphenous vene, arteria Iliacs, left interior mammory artery (LIMA) and aorta were tested for infection with the fiber 16 chimera and Ad5 (both carrying luciferase as a marker gene). These experiments (n=11) demonstrated that, on average, the fiber 16 chimera yielded 61.4 fold increased levels in luciferase activity (SD±54.8) as compared to Ad5. The high standard deviation (SD) is obtained due to the finding that the adenoviruses used vary in their efficiency of infection of SMC derived from different human vessels. In a next experiment, an equal number of virus particles was added to wells of 24-well plates that contained different HUVsmc cell concentrations confluency. For this purpose, HUVsmc were seeded at 10000, 20000, 40000, 60000, and 80000 cells per well of 24-well plates (in triplicate). Twenty-four hours later these cells were infected as described above with medium containing $2 \times 10^8$ virusparticles. The viruses used were, besides the control adenovirus serotype 5, the chimera fiber 16. The result of the transgene expression (RLU) per microgram protein determined 48 hours after infection (see FIG. 8b) shows that the fiber 16 chimeric adenovirus is better suited to infect smooth muscle cells even when these cells are 100% confluent which better mimics an in vivo situation.

To identify the number of SMCs transduced with the fiber 16 chimera and Ad5, we performed transduction experiments with Ad5.GFP and Ad5Fib16.GFP (identical batches as used for EC infections). Human umbilical vein SMC were seeded at a concentration of 60000 cells per well in 24-well plates and exposed for 2 hours to 500 or 5000 virus particles per cell of Ad5:GFP or Ad5Fib16.GFP. Forty-eight hours after exposure cells were harvested and analyzed using a flow cytometer. The results obtained show that the fiber 16 mutant yields approximately 10 fold higher transduction of SMC since the GFP expression measured after transduction with 5000 virus particles of Ad5.GFP is equal to GFP expression after transduction with 500 virus particles per cell of the fiber 16 chimera (FIG. 8c).

C) Subgroup B Fiber Mutants Other than Fiber 16

The shaft and knob of fiber 16 are derived from adenovirus serotype 16 which, as described earlier, belongs to subgroup B. Based on hemagglutination assays, DNA restriction patterns, and neutralization assays the subgroup B viruses have been further subdivided into subgroup B1 and B2 (Wadeil et al 1984). Subgroup B1 members include serotypes 3, 7, 16, 21, and 51. Subgroup B2 members include 11, 14, 34, and 35. To test whether the increased infection of smooth muscle cells is a trade of all fibers derived from subgroup B or specific for one or more subgroup B fiber molecules, we compared fiber 16 and fiber 51 (both subgroup B1) with fiber 11 and fiber 35 (both subgroup B2). For this purpose HUVsmc were infected with increasing amounts of virus particles per cell (156, 312, 625, 1250, 2500, 5000). The fiber mutant all carry the Luciferase marker gene (Ad5Fib11.Luc: $1.1 \times 10^{12}$ vp/ml; Ad5Fib35Luc: $1.4 \times 10^{12}$ vp/ml; Ad5Fib51Luc: $1.0 \times 10^{12}$ vp/ml). Based on the Luciferase activity measured and shown in FIG. 8d, efficient infection of SMC is not a general trade of all subgroup B fiber molecules. Clearly, fiber 16 an fiber 11 are better suited for infection of SMC than fiber 35 and fiber 51. Nevertheless, all subgroup B fiber mutants tested infect SMC better as compared to Ad5.

D) Organ Culture Experiments

We next identified whether the observed difference in transduction of EC and SMC using the fiber 16 chimera or the Ad5 can also be demonstrated in organ culture experiments. Hereto, We focused on the following tissues:

1) Human Saphenous vein: the vein used in approximately 80% of all clinical vein grafting procedures
2) Human pericard/epicard: for delivery of recombinant adenoviruses to the pericardial fluid which after infection of the pericardial or epicardial cells produce the protein of interest from the transgene carried by the adenovirus.
3) Human coronary arteries: percutaneous transdermal coronary angioplasty (PTCA) to prevent restenosis. Of the coronary arteries we focused on the Left artery descending (LAD) en right coronary artery (RCA).

Parts of a human saphenous vein left over after vein graft surgery were sliced into pieces of approximately 0.5 cm. These pieces (n=3) were subsequently cultured for 2 hours in 200 ml of $5 \times 10^{10}$ virus particles per ml. After two hours virus exposure the pieces were washed with PBS and cultured for another 48 hours at 37° C. in a 10% $CO_2$ incubator. The pieces were then washed fixated and stained for LacZ transgene expression. The viruses were Ad5.LacZ ($2.2 \times 10^{12}$ vp/ml), the fiber 16 chimera Ad5Fib16.LacZ ($5.2 \times 10^{11}$ vp/ml), and A fiber 51 chimera: Ad5Fib51.LacZ ($2.1 \times 10^{12}$ vp/ml). The pieces of saphenous vein were macroscopically photographed using digital camera. Based on LacZ transgene expression obtained after 2 hours of virus exposure on saphenous vein slices, both the fiber 16 and the fiber 51 chimeric viruses give higher infection since much more blue staining is observed using these viruses as compared to Ad5.LacZ (FIG. 8e). Identical experiments as described on saphenous vein were performed with human pericard and the human coronary arteries: RCA and LAD. Results of these experiments (FIGS. 8f–8g–8h respectively) together with the experiments performed on primary cells confirmed the superiority of the fiber 16 and 51 mutants as compared to Ad5 in infecting human cardiovascular tissues.

E) CAR and Integrin Expression on Human EC and SMC

From the above described results it is clear that the chimeric adenovirus with the shaft and knob from fiber 16 is well suited to infect endothelial cells and smooth muscle cells. Thus, by changing the fiber protein on Ad5 viruses we are able to increase infection of cells that are poorly infected by Ad5. The difference between Ad5 and Ad5Fib16, although significant on both cell types, is less striking on endothelial cells as compared to smooth muscle cells. This may reflect differences in receptor expression. For example, HUVsmc significantly more $\alpha_v\beta5$ integrins than HUVEC (see below). Alternatively, this difference may be due to differences in expression of the receptor of fiber 16. Ad5.LucFib16 infects umbilical vein smooth muscle cells approximately 8 fold better than umbilical vein endothelial cells whereas in case of Ad5.Luc viruses endothelial cells are better infected than smooth muscle cells. To test whether Ad5 infection correlated with receptor expression of these cells the presence of CAR and $\alpha_v$-integrins was assayed on a flow cytometer. For this purpose $1 \times 10^5$ HUVEC cells or HUVsmc were washed once with PBS/0.5% BSA after which the cells were pelleted by centrifugation for 5 minutes at 1750 rpm at room temperature. Subsequently, 10 µl of a 100 times diluted $\alpha_v\beta3$ antibody (Mab 1961, Brunswick chemie, Amsterdam, The Netherlands), a 100 times diluted antibody $\alpha_v$B5 (antibody (Mab 1976, Brunswick chemie, Amsterdam, The Netherlands), or 2000 times diluted CAR antibody was a kind gift of Dr. Bergelson, Harvard Medical School, Boston, USA (Hsu et al) was added to the cell pellet after which the cells were incubated for 30 minutes at 4° C. in a dark environment. After this incubation, cells were washed twice with PBS/0.5% BSA and again pelleted by centrifugation for 5 minutes at 1750 rpm room temperature. To label the cells, 10 ml of rat anti mouse IgG1 labeled with phycoerythrine (PE) was added to the cell pellet upon which the cells were again incubated for 30 minutes at 4° C. in a dark environment. Finally, the cells were washed twice with PBS/0.5% BSA and analyzed on a flow cytometer. The results of these experiments are shown in table III. From the results it can be concluded that HUVsmc do not express detectable levels of CAR confirming that these cells are difficult to transduce with an adenovirus which enters the cells via the CAR receptor.

F) Infection of Human A549 Cells

As a control for the experiments performed on endothelial cells and smooth muscle cells, A549 cells were infected to establish whether an equal amount of virus particles of the different chimeric adenoviruses show significant differences in transgene expression on cell lines that are easily infected by adenovirus. This is to investigate whether the observed differences in infection efficiency on endothelial and smooth muscle cells are cell type specific. For this purpose, $10^5$ A549 cells were seeded in 24-well plates in a volume of 200 µl. Two hours after seeding the medium was replaced by medium containing different amounts of particles of either fiber chimera 5, 12, 16, or 40-L (MOI=0, 5, 10, 25, 100, 500). Twenty-four hours after the addition of virus, the cells were washed once with PBS after which the cells were lysed by the addition of 100 μl lysisbuffer to each well (1% Triton X-100 in PBS) after which transgene expression (Luciferase activity) and the protein concentration was determined. Subsequently, the luciferase activity per μg protein was calculated. The data, shown in table IV, demonstrate that Ad5.Luc viruses infect A549 cells most efficient while the infection efficiency of Ad5LucFib16 or Ad5.LucFib40-L is a few times lower. This means that the efficient infection of endothelial cells and especially smooth muscle cells is due to differences in binding of the virus to these cells and not to the amount of virus or the quality of the viruses used.

TABLE I

| Serotype | Tail oligonucleotide | Knob oligonucleodite |
|---|---|---|
| 4 | A | 1 |
| 8 | B | 2 |
| 9 | B | 2 |
| 12 | E | 3 |
| 16 | C | 4 |
| 19p | B | 2 |
| 28 | B | 2 |
| 32 | B | 2 |
| 36 | B | 2 |
| 37 | B | 2 |
| 40-1 | D | 5 |
| 40-2 | D | 6 |
| 41-s | D | 5 |
| 41-1 | D | 7 |
| 49 | B | 2 |
| 50 | B | 2 |
| 51 | C | 8 |

A: 5'-CCC GTG TAT CCA TAT GAT GCA GAC AAC GAC CGA CC-3'
B: 5'-CCC GTC TAC CCA TAT GGC TAC GCG CGG-3'
C: 5'-CCK GTS TAC CCA TAT GAA GAT GAA AGC-3'
D: 5'-CCC GTC TAC CCA TAT GAC ACC TYC TCA ACT C-3'
E: 5'-CCC GTT TAC CCA TAT GAC CCA TTT GAC ACA TCA GAC-3'
1: 5'-CCG ATG CAT TTA TTG TTG GGC TAT ATA GGA-3'
2: 5'-CCG ATG CAT TYA TTC TTG GGC RAT ATA GGA-3'
3: 5'-CCG ATG CAT TTA TTC TTG GGR AAT GTA WGA AAA GGA-3'
4: 5'-CCG ATG CAT TCA GTC ATC TTC TCT GAT ATA-3'
5: 5'-CCG ATG CAT TTA TTG TTC AGT TAT GTA GCA-3'
6: 5'-GCC ATG CAT TTA TTG TTC TGT TAC ATA AGA-3'
7: 5'-CCG TTA ATT AAG CCC TTA TTG TTC TGT TAC ATA AGA A-3'
8: 5'-CCG ATG CAT TCA GTC ATC YTC TWT AAT ATA-3'

TABLE II

| Organ | Control Ad5 | Fib 12 | Fib 16 | Fib 28 | Fib 40-L |
|---|---|---|---|---|---|
| Liver | 740045 | 458 | 8844 | 419 | 2033 |
| Spleen | 105432 | 931 | 3442 | 592 | 16107 |
| Lung | 428 | 315 | 334 | 316 | 424 |
| Kidney | 254 | 142 | 190 | 209 | 224 |
| Heart | 474 | 473 | 276 | 304 | 302 |
| Brain | 291 | 318 | 294 | 323 | 257 |

TABLE III

| Cell line | $\alpha_v\beta_3$ | $\alpha_v\beta_5$ | CAR |
|---|---|---|---|
| HUVEC 70% | 98.3% | 18.9% | 18.1% |
| HUVEC 100% | 97.2% | 10.5% | 7.2% |
| HUVamc 70% | 95.5% | 76.6% | 0.3% |
| HUVamc 100% | 92.2% | 66.5% | 0.3% |
| PER.C6 | 7.8% | 16.8% | 99.6% |

TABLE IV

| MOI (VP/Cell) | Control Ad5 | Fiber 12 | Fiber 16 | Fiber 40-L |
|---|---|---|---|---|
| 0 | 0 | 0 | 0 | 0 |
| 5 | 1025 | 46 | 661 | 443 |
| 10 | 1982 | 183 | 1704 | 843 |
| 25 | 4840 | 200 | 3274 | 2614 |
| 100 | 21875 | 1216 | 13432 | 11907 |
| 500 | 203834 | 3296 | 93163 | 71433 |

REFERENCES

Arnberg, N., Mei Y. and Wadell G., 1997. Fiber genes of adenoviruses with tropism for the eye and the genital tract. Virology 227: 239–244.

Bergelson, J. M., Cunningham, J. A., Droguett, G. Kurt-Jones, E. A., Krithivas, A., Hong, J. S., Horwitz, M. S., Crowell, R. L. and Finberg, R. W. (1977). Isolation of a common receptor for coxsackie B virus and adenoviruses 2 and 5. Science 275: 1320–1323.

Bout, A. (1997) Gene therapy, p. 167–182. In: D. J. A. Crommelin and R. D. Sindelar (ed.), Pharmaceutical Biotechnology, Harwood Academic Publishers.

Bout, A. (1996) Prospects for human gene therapy. Eur. J. Drug Met. and Pharma., 2, 175–179.

Blaese, M., Blankenstein, T., Brenner, M., Cohen-Hagenauer, O., Gansbacher, B., Russel, S., Sorrentino, B. and Velu, T. (1995) Cancer Gene Ther. 2: 291–297

Brody, S. L. and Crystal, R. G. (1994) Adenovirus mediated in vivo gene transfer. Ann. N.Y. Acad Sci. 716:90–101.

Carter, A. J., Laird, J. R., Farb, A., Kufs, W., Wortham, D. C. and Virmani, R. (1994) Morphologic characteristics of lesion formation and time course of smooth muscle cell proliferation in a porcine proliferative restenosis model. J. Am. Coll. Cardiol. 24: 1398–1405.

Chroboczek J., Ruigrok R. W. H., and Cusack S., 1995. Adenovirus fiber, p. 163–200. In: W. Doerfler and P. Bohm (ed.). The molecular repertoire of adenoviruses, L. Springer-Verlag, Berlin.

Defer C., Belin M., Caillet-Boudin M. and Boulanger P., 1990. Human adenovirus-host cell interactions, comparative study with members of subgroup B and C. Journal of Virology 64 (8): 3661–3673.

Fallaux, F. J., Bout, A., van der Velde, I et al. New helper cells and matched E1-deleted adenovirus vectors prevent generation of replication competent adenovirus. Human Gene Therapy, 9, (1998) p1909–1917.

Francki, R. I. B., Fauquet, C. M., Knudson, D. L., and Brown, F. (1991) Classification and nomenclature of viruses. Fifth report of the international Committee on taxonomy of viruses. Arch, Virol. Suppl. 2: 140–144.

Gall J., Kass-Eisler A., Leinwand L., and Falck-Pedersen, E. (1996) Adenovirus type 5 and 7 capsid chimera: fiber replacement alters receptor tropism without affecting primary immune neutralization epitopes. Journal of Virology 70 (4): 2116–2123.

Gerber, U. F., Willets, M., Webster, P., and Helenius, A. (1993). Stepwise dismantling of adenovirus 2 during entry into cells. Cell 75: 477–486.

Hynes, R. O. (1992) Integrins: versatility, modulation and signaling in cell adhesion. Cell 69: 11–25.

Herz, J. and Gerard, R. D. (1993) Adenovirus-mediated transfer of low density lipoprotein receptor gene acutely accelerates cholesterol clearance in normal mice. Proc. Natl. Acad. Sci. U.S.A. 96: 2812–2816.

Hierholzer, J. C. (1992) Adenovirus in the immunocompromised host. Clin. Microbiol Rev. 5, 262–274.

Hierholzer, J. C., Wigand, R., Anderson, L. J., Adrian, T., and Gold, J. W. M. (1988) Adenovirus from patients with AIDS: a plethora of serotypes and a description of five new serotypes of subgenus D (types 43–47). J. Infect. Dis. 158, 804–813.

Hong, S. S., Karayan, L., Tournier, J., Curiel, D. T. and Boulanger, P. A. (1997) Adenovirus type 5 fiber knob binds to MHC class I $\alpha 2$ domain at the surface of human epithelial and B lymphoblastoid cells. EMBO J. 16: 2294–2306.

Hsu, K. H., Lonberg-Holm, K., Alstein, B. and Crowell, R. L. (1988) A monoclonal antibody specific for the cellular receptor for the group B coxsackieviruses, J. Virol 62(5): 1647–1652.

Huard, J., Lochmuller, H., Acsadi, G., Jani, A., Massie, B. and Karpati, G. (1995) The route of administration is a major determinant of the transduction efficiency of rat tissues by adenoviral recombinants. Gene Ther. 2: 107–115.

Ishibashi, M. and Yasue, H. (1984) The adenoviruses, H. S. Ginsberg, ed., Plenum Press, London, New York. Chapter 12, 497–561.

Jaffe, E. A., Nachman, R. L., Becker, C. G., Minick, C. R. (1973) Culture of endothelial cells derived from umbilical veins. Identification by morphologic and immunologic criteria. *J. Clin. Invest.* 52, 2745–2756.

Kass-Eisler, A., Falck-Pederson, E., Elfenbein, D. H., Alvira, M., Buttrick, P. M., and Leinwand, L. A. (1994) The impact of developmental stage, route of administration and the immune system on adenovirus-mediated gene transfer. Gene Ther. 1: 395–402.

Khoo, S. H., Bailley, A. S., De Jong, J. C., and Mandal, B. K. (1995) Adenovirus infections in human immunodeficiency virus-positive patients: Clinical features and molecular epidemiology. J. Infect. Dis 172, 629–637.

Kidd, A. H., Chroboczek, J., Cusack, S., and Ruigrok, R. W. (1993) Adenovirus type 40 virions contain two distinct fibers. Virology 192, 73–84.

Krasnykh, V. N., Mikheeva G. V., Douglas, J. T. and Curiel, D. T. (1996) Generation of recombinant adenovirus vectors with modified fibers for altering viral tropism. J. Virol. 70(10): 6839–6846.

Krasnykh, V. N., Dmitriev, I., Mikheeva, G., Miller, C. R., Belousova, N. and Curiel, D. T. (1998) Characterization of an adenovirus vector containing a heterologous peptide epitope in the HI loop of the fiber knob. J. Virol. 72(3): 1844–1852.

Law, L., Chillon, M. Bosch, A., Armentano, D., Welsh, M. J. and Davidson, B. L. (1998) Infection of primary CNS cells by different adenoviral serotypes: Searching for a more efficient vector. Abstract 1st Annual Meeting American Society of Gene Therapy, Seattle, Wash.

Leppard, K. N. (1997) E4 gene function in adenovirus, adenovirus vector and adeno-associated virus infections. J. Gen. Virol. 78: 2131–2138.

Lloyd Jones, D. M. and Bloch, K. D. (1996) The vascular biology of nitric oxide and its role in atherogenesis. Annu. Rev. Med. 47: 365–375.

Morgan, C., Rozenkrantz, H. S., and Mednis, B. (1969) Structure and development of viruses as observed in the electron microscope Entry and uncoating of adenovirus. J. Virol 4, 777–796.

Roelvink, P. W., Kovesdi, I. and Wickham T. J. (1996) Comparative analysis of adenovirus fiber-cell interaction: Adenovirus type 2 (Ad2) and Ad9 utilize the same cellular fiber receptor but use different binding strategies for attachment. J. Virol. 70: 7614–7621.

Roelvink, P. W., Lizonova, A., Lee, J. G. N., Li, Y., Bergelson, J. M., Finberg, R. W., Brough, D. E., Kovesdi, I. and Wickham, T. J. (1998) The coxsackie-adenovirus receptor protein can function as a cellular attachment protein for adenovirus serotypes from subgroups A, C, D, E, and F. J. Virol. 72: 7909–7915.

Rogers, B. E., Douglas, J. T., Ahlem, C., Buchsbaum, D. J., Frincke, J. and Curiel, D. T. (1997) Use of a novel cross-linking method to modify adenovirus tropism. Gene Ther. 4: 1387–1392.

Schulick, A. H., Vassalli, G., Dunn, P. F., Dong, G., Rade, J. J., Zamarron, C. and Dichek, D. A. (1997). Established immunity precludes adenovirus-mediated gene transfer in rat carotid arteries.

Schnurr, D. and Dondero, M. E. (1993) Two new candidate adenovirus serotypes. Intevirol. 36, 79–83.

Schwartz, R. S., Edwards, W. D., Huber, K. C., Antonindes, L. C., Bailey, K. R., Canrud, A. R., Jorgenson, M. A. and Holmes, D. R. Jr. (1993) Coronary restenosis: Prospects for solution and new perspectives from a porcine model. Mayo Clin. Proc. 68: 54–62.

Shi, Y., Pieniek, M., Fard, A., O'Brien, J., Mannion, J. D. and Zalewski, A. (1996) Adventitial remodeling after coronary arterial injury. Circulation 93: 340–348.

Shabram. P. W., Giroux, D. D., Goudreau, A. M., Gregory, R. J., Horn, M. T., Huyghe, B. G., Liu, X., Nunnally, M. H., Sugarman, B. J. and Sutjipto, S. (1997) Analytical anion-exchange HPLC of recombinant type-5 adenoviral particles. Hum. Gene Ther. 8(4): 453–465.

Signes, G., Akusjarvi, G., and Petterson, U. (1985). Adenovirus 3 fiberpolypeptide gene: Complications for the structure of the fiber protein. J. Virol. 53, 672–678.

Stevenson, S. C., Rollence, M., White B., Weaver L. and McClelland, A. (1995) Human adenovirus serotypes 3 and 5 bind to two different cellular receptors via the fiber head domain. J. Virol 69 (5): 2850–2857.

Stevenson, S. C., Rollence, M., Marshall-Neff, J. and McClelland, A. (1997) Selective targeting of human cells by a chimaeric adenovirus vector containing a modified fiber protein. J. Virology 71 (6): 4782–4790.

Stouten, P. W. F., Sander, C., Ruigrok, R. W. H., and Cusack, S. (1992) New triple helical model for the shaft of the adenovirus fiber. J. Mol. Biol. 226, 1073–1084.

Svensson, V. and Persson, R. (1984). Entry of adenovirus 2 into Hela cells. J. Virol. 51, 687–694.

Van der Vliet, P. C. (1995) Adenovirus DNA replication In: W. Doerfler and P. Bohm (eds.) The molecular repertoire of adenoviruses II. Springer-Verlag, Berlin.

Varga, M. J., Weibull, C., and Everitt, E. (1991). Infectious entry pathway of adenovirus type 2. J. Virol 65, 6061–6070.

Varenne, O., Pislaru, S., Gillijns, H., Van Pelt, N., Gerard, R. D., Zoldhelyi, P., Van de Werf, F., Collen, D. and Janssens, S. P. (1998) Local adenovirus-mediated transfer of human endothelial nitric oxide synthetase reduces huminal narrowing after coronary angioplasty in pigs. Circulation 98: 919–926.

Wadell, G. (1984) Molecular Epidermiology of human adenoviruses *Curr. Top. Microbiol. Immunol.* 110, 191–220.

Wickham, T. J., Carrion, M. E. and Kovesdi, L., 1995. Targeting of adenovirus penton base to new receptors through replacement of its RGD motif with other receptor-specific peptide motifs. Gene Therapy 2: 750–756.

Wickham, T. J., Segal, D. M., Roelvink, P. M., Carrion, M. E., Lizonova, A., Lee, G-M., and Kovesdi, I. (1996) Targeted adenovirus gene transfer to endothelial and smooth muscle cells by using bispecific antibodies. J. Virol. 70(10), 6831–6838.

Wickham, T. J., Mathias, P., Cherish, D. A., and Nemerow, G. R. (1993) Integrins avb3 and avb5 promote adenovirus internalization but not virus attachment. Cell 73, 309–319.

Wijnberg, M. J., Quax, P. H. Z., Nieuwenbroek, N. M. E., Verheijen, J. H. (1997) The migration of human smooth muscle cells in vitro is mediated by plasminogen activation and can be inhibited by alpha(2) macro globulin receptor associated protein. *Thromb. and Haemostas.* 78, 880–886.

Wold, W. S., Tollefson, A. E. and Hermiston, T. W. (1995) E3 transcription unit of adenovirus. In: W. Doerfler and P. Böhm (eds.). The molecular repertoire of adenoviruses I. Springer-Verlag, Berlin.

Zabner, J., Armentano, D., Chillon, M., Wadsworth, S. C., and Welsh, M. J. (1998) Type 17 fiber enhances gene transfer Abstract 1st Annual Meeting American Society of Gene Therapy, Seattle, Wash.

What is claimed is:

1. A method for reducing a tissue tropism of an adenovirus capsid of a subgroup C origin for liver cells as compared to the corresponding wild type adenovirus capsid, said method comprising:
   i) exchanging a first nucleic acid encoding a knob domain of a fiber protein of the adenovirus of subgroup C origin for a second nucleic acid encoding a knob domain of a fiber protein of an adenovirus selected from the group consisting of adenovirus 12, adenovirus 16, adenovirus 28, and adenovirus 40-L;
   ii) introducing the resulting nucleic acid from step i) into a cell capable of producing said adenovirus capsid; and
   iii) allowing said cell to produce said adenovirus capsid, thus reducing the tissue tropism of the adenovirus capsid for liver cells as compared to the corresponding wild type adenovirus capsid.

2. A construct deposited with the ECACC under deposit number 01121708.

3. A construct deposited with the ECACC under deposit number 01121710.

4. A construct deposited with the ECACC under deposit number 01121709.

5. A construct deposited with the ECACC under deposit number 01121711.

6. A construct deposited with the ECACC under deposit number 0112712.

* * * * *

UNITED STATES PATENT AND TRADEMARK OFFICE
CERTIFICATE OF CORRECTION

PATENT NO.       : 6,929,946 B1
APPLICATION NO.  : 09/444284
DATED            : August 16, 2005
INVENTOR(S)      : Ronald Vogels, Menzo J. E. Havenga and Abraham Bout It is certified that error appears in the above-identified patent and that said Letters Patent is hereby corrected as shown below:

On the title page:

In ITEM (56)     change "JP   207631   3/1990" to
                 --JP   2078631   3/1990--

In ITEM (56)     insert --Skolnick et al., 2000, TIBTECH,
                 vol. 18, pp. 34-39.*--
                 change "2001, Journl of Vascular Research, vol. 38,
                 471-478.*" to --2001, Journal of Vascular Research,
                 vol. 38, 471-478.*--
                 change "#Ball-Goodrich et al., "Paroviral Target Cell
                 Specificity: Acquisition of Fibrotropism by a Mutant of
                 the Lymphotropic Strain of Minute Virus of Mice
                 Involves Multiple Amino Acid Substitutes within the
                 Capsid," Virology, 184, 175-186." to
                 --#Ball-Goodrich et al., "Parvoviral Target Cell
                 Specificity: Acquisition of Fibrotropism by a Mutant of
                 the Lymphotropic Strain of Minute Virus of Mice
                 Involves Multiple Amino Acid Substitutes within the
                 Capsid," Virology, 184, 175-186 (1991).--
                 change "#Boursnell et al., In vivo" to
                 --#Boursnell et al., In vitro--

In ITEM (56)     change "#Dupuit et al., "Regenerating Cells in Human
                 Airwey" to
                 -#Dupuit et al., "Regenerating Cells in Human
                 Airway-- change "#Falgout et al., Characterizations of
                 Adenovirus Particles Made by Deletion Mutuants"
                 to --#Falgout et al., Characterizations of Adenovirus
                 Particles Made by Deletion Mutants--
                 change "#Horvath et al., "Nonpermissively of Human
                 Blood" to --#Horvath et al., "Nonpermissivity of
                 Human Peripheral Blood--
                 change "#Matrangeli el al., "In Vivo Gene"
                 to --#Mastrangeli et al., "In Vivo Gene--
                 change "#Mautner et al., Recombination in
                 Adeniovirus: Analysis" to --#Mautner et al.,
                 Recombination in Adenovirus: Analysis--
                 change "#NEDA et al.," to --#Neda et al.,--
                 change "file://F1N1Hrec.htm" to
                 --file:///F1NIin Hrec.htm--

Page 1 of 3

CERTIFICATE OF CORRECTION (continued)  
U.S. Pat. No. 6,929,946 B1  
Page 2 of 3

In ITEM (56)      change "#Pring-Akerblom et al., Sequence Charaterization" to --#Pring-Åkerblom et al., Sequence Characterization--

In ITEM (57) Abstract      change "fragments can comprises" to --fragments can comprise--  
change "Particular construct" to --Particular constructs--

| | | |
|---|---|---|
| | COLUMN 6, LINE 66, | change "from" to --form-- |
| | COLUMN 12, LINE 35, | change "contain deletion in" to --contain deletions in-- |
| | COLUMN 16, LINE 1, | change "aspect of the" to --aspect the-- |
| | COLUMN 20, LINE 18, | change "virus bend" to --virus band-- |
| | COLUMN 23, LINE 19, | change "(Wadeil et al 1984)." to --(Wadell et al. 1984).-- |
| | COLUMN 25, LINE 35, | change "A: 5'-CCC GTG TAT CCA TAT GAT GCA GAC AAC GAC CGA CC-3'" to --A: 5'-CCC GTG TAT CCA TAT GAT GCA GAC AAC GAC CGA CC-3'-- |
| | COLUMN 25, LINE 36, | change "B: 5'-CCC GTC TAC CCA TAT GGC TAC GCG CGG-3'" to --B: 5'-CCC GTC TAC CCA TAT GGC TAC GCG CGG-3'-- |
| TABLE 1 | | |
| | COLUMN 25, LINE 37, | change "C: 5'-CCK GTS TAC CCA TAT GAA GAT GAA AGC-3'" to --C: 5'-CCK GTS TAC CCA TAT GAA GAT GAA AGC-3'-- |
| | COLUMN 25, LINE 38, | change "D: 5'-CCC GTC TAC CCA TAT GAC ACC TYC TCA ACT C-3'" to --D: 5'-CCC GTC TAC CCA TAT GAC ACC TYC TCA ACT C-3'-- |
| | COLUMN 25, LINE 39, | change "E: 5'-CCC GTT TAC CCA TAT GAC CCA TTT GAC ACA TCA GAC-3'" to --E: 5'-CCC GTT TAC CCA TAT GAC CCA TTT GAC ACA TCA GAC-3'-- |
| | COLUMN 25, LINE 40, | change "1: 5'-CCG ATG CAT TTA TTG TTG GGC TAT ATA GGA-3'" to --1: 5'-CCG ATG CAT TTA TTG TTG GGC TAT ATA GGA-3'-- |
| | COLUMN 25, LINE 41, | change "2: 5'-CCG ATG CAT TYA TTC TTG GGC RAT ATA GGA-3'" to --2: 5'-CCG ATG CAT TYA TTC TTG GGC RAT ATA GGA-3'-- |
| | COLUMN 25, LINE 42, | change "3: 5'-CCG ATG CAT TTA TTC TTG GGR AAT GTA WGA AAA GGA-3'" to --3: 5'-CCG ATG CAT TTA TTC TTG GGR AAT GTA WGA AAA GGA-3'-- |
| | COLUMN 25, LINE 43, | change "4: 5'-CCG ATG CAT TCA GTC ATC TTC TCT GAT ATA-3'" to --4: 5'-CCG ATG CAT TCA GTC ATC TTC TCT GAT ATA-3'-- |
| | COLUMN 25, LINE 44, | change "5: 5'-CCG ATG CAT TTA TTG TTC AGT TAT GTA GCA-3'" to --5: 5'-CCG ATG CAT TTA TTG TTC AGT TAT GTA GCA-3'-- |
| | COLUMN 25, LINE 45, | change "6: 5'-GCC ATG CAT TTA TTG TTC TGT TAC ATA AGA-3'" to --6: 5'-GCC ATG CAT TTA TTG TTC TGT TAC ATA AGA-3'-- |

CERTIFICATE OF CORRECTION (continued)
U.S. Pat. No. 6,929,946 B1

TABLE 1

| | | |
|---|---|---|
| COLUMN 25, | LINE 46, | change "7: 5'-CCG TTA ATT AAG CCC TTA TTG TTC TGT TAC ATA AGA A-3'" to --7: 5'-CCG TTA ATT AAG CCC TTA TTG TTC TGT TAC ATA AGA A-3'-- |
| COLUMN 25, | LINE 47, | change " 8: 5'-CCG ATG CAT TCA GTC ATC YTC TWT AAT ATA-3'" to --8: 5'-CCG ATG CAT TCA GTC ATC YTC TWT AAT ATA-3'-- |
| COLUMN 25, | LINE 63, | change "HUVamc 70%" to --HUVsmc 70%-- |
| COLUMN 25, | LINE 64, | change "HUVamc 100%" to --HUVsmc 100%-- |
| COLUMN 26, | LINE 18, | change "(1977)." to --(1997).-- |
| COLUMN 26, | LINE 39, | change "L." to --I.-- |
| COLUMN 27, | LINE 32, | change "Bailley," to --Bailey,-- |
| COLUMN 28, | LINE 18, | change "Antonindes," to --Antoniudes,-- |
| COLUMN 28, | LINE 19, | change "Canrud," to --Camrud,-- |
| COLUMN 28, | LINE 31, | change "Signes," to --Signäs,-- |
| COLUMN 28, | LINE 58, | change "huminal" to --luminal-- |
| COLUMN 29, | LINE 10, | change "Quax, P.H.Z.," to --Quax, P.H.A.,-- |

Signed and Sealed this

Sixteenth Day of March, 2010

David J. Kappos
*Director of the United States Patent and Trademark Office*

SEQUENCE LISTING

<160> NUMBER OF SEQ ID NOS: 24

<210> SEQ ID NO 1
<211> LENGTH: 35
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Tail nucleotide A"

<400> SEQUENCE: 1
cccgtgtatc catatgatgc agacaacgac cgacc                              35

<210> SEQ ID NO 2
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Tail nucleotide B"

<400> SEQUENCE: 2
cccgtctacc catatggcta cgcgcgg                                       27

<210> SEQ ID NO 3
<211> LENGTH: 27
<212> TYPE: DNA
<213> ORGANISM: Artificial Sequence
<220> FEATURE:
<221> NAME/KEY: misc_feature
<223> OTHER INFORMATION: /note="Tail nucleotide C"
<221> NAME/KEY: misc_feature
<223> OTHER INFORMATION: Description of Artificial Sequence: primer

<400> SEQUENCE: 3
cckgtstacc catatgaaga tgaaagc                                       27

<210> SEQ ID NO 4
<211> LENGTH: 31
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Tail nucleotide D"

<400> SEQUENCE: 4
cccgtctacc catatgacac ctyctcaact c                                  31

<210> SEQ ID NO 5
<211> LENGTH: 36
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Tail nucleotide E"

<400> SEQUENCE: 5
cccgtttacc catatgaccc atttgacaca tcagac                              36

<210> SEQ ID NO 6
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 1"

<400> SEQUENCE: 6
ccgatgcatt tattgttggg ctatatagga                                     30

<210> SEQ ID NO 7
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 2"

<400> SEQUENCE: 7
ccgatgcatt yattcttggg cratatagga                                     30

<210> SEQ ID NO 8
<211> LENGTH: 36
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 3"

<400> SEQUENCE: 8
ccgatgcatt tattcttggg raatgtawga aaagga                              36

<210> SEQ ID NO 9
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 4"

<400> SEQUENCE: 9
ccgatgcatt cagtcatctt ctctgatata                                     30

<210> SEQ ID NO 10
<211> LENGTH: 30

```
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 5"

<400> SEQUENCE: 10
ccgatgcatt tattgttcag ttatgtagca                            30

<210> SEQ ID NO 11
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 6"

<400> SEQUENCE: 11
gccatgcatt tattgttctg ttacataaga                            30

<210> SEQ ID NO 12
<211> LENGTH: 37
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 7"

<400> SEQUENCE: 12
ccgttaatta agcccttatt gttctgttac ataagaa                    37

<210> SEQ ID NO 13
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: primer
<221> NAME/KEY: misc_feature
<223> OTHER INFORMATION: /note="Knob nucleotide 8"

<400> SEQUENCE: 13
ccgatgcatt cagtcatcyt ctwtaatata                            30

<210> SEQ ID NO 14
<211> LENGTH: 42
<212> TYPE: DNA
<213> ORGANISM: Artificial Sequence
<220> FEATURE:
<221> NAME/KEY: misc_feature
<223> OTHER INFORMATION: Description of Artificial Sequence: primer
      NY-UP

<400> SEQUENCE: 14
cgacatatgt agatgcatta gtttgtgtta tgtttcaacg tg              42

<210> SEQ ID NO 15
<211> LENGTH: 19
<212> TYPE: DNA
<213> ORGANISM: Artificial Sequence
<220> FEATURE:
<221> NAME/KEY: misc_feature
<223> OTHER INFORMATION: Description of Artificial Sequence: primer
```

NY-DOWN

<400> SEQUENCE: 15
ggagaccact gccatgttg                                                    19

<210> SEQ ID NO 16
<211> LENGTH: 1746
<212> TYPE: DNA
<213> ORGANISM: Adenoviridae
<220> FEATURE:
<221> NAME/KEY: misc_feature
<223> OTHER INFORMATION: /note="Ad5 chimeric fiber"

<400> SEQUENCE: 16

```
atgaagcgcg caagaccgtc tgaagatacc ttcaaccccg tgtatccata tgacacggaa      60
accggtcctc caactgtgcc ttttcttact cctcccttttg tatcccccaa tgggtttcaa    120
gagagtcccc ctggggtact ctctttgcgc tatccgaac ctctagttac ctccaatggc     180
atgcttgcgc tcaaaatggg caacggcctc tctctggacg aggccggcaa ccttacctcc    240
caaaatgtaa ccactgtgag cccacctctc aaaaaaacca agtcaaacat aaacctggaa    300
atatctgcac ccctcacagt tacctcagaa gccctaactg tggctgccgc cgcacctcta    360
atggtcgcgg caacacact caccatgcaa tcacaggccc cgctaaccgt gcacgactcc    420
aaacttagca ttgccaccca aggaccctc acagtgtcag aaggaaagct agccctgcaa     480
acatcaggcc cctcaccac caccgatagc agtaccctta ctatcactgc ctcaccccct    540
ctaactactg ccactggtag cttgggcatt gacttgaaag agcccattta tacacaaaat    600
ggaaaactag gactaaagta cgggctcct ttgcatgtaa cagacgacct aaacactttg     660
accgtagcaa ctggtccagg tgtgactatt aataatactt ccttgcaaac taagttact    720
ggagccttgg gttttgattc acaaggcaat atgcaactta atgtagcagg aggactaagg    780
attgattctc aaaacagacg ccttatactt gatgttagtt atccgtttga tgctcaaaac    840
caactaaatc taagactagg acagggcccc ttttttataa actcagccca aacttggat   900
attaactaca caaaggcct ttacttgttt acagcttcaa acaattccaa aaagcttgag    960
gttaacctaa gcactgccaa ggggttgatg tttgacgcta cagccatagc cattaatgca  1020
ggagatgggc ttgaatttgg ttcacctaat gcaccaaaca caatcccct caaaacaaaa  1080
attggccatg cctagaatt tgattcaaac aaggctatgg ttcctaaact aggaactggc  1140
cttagttttg acagcacagg tgccattaca gtaggaaaca aaataatga taagctaact  1200
ttgtggacca caccagctcc atctcctaac tgtagactaa atgcagagaa agatgctaaa  1260
ctcactttgg tcttaacaaa atgtggcagt caaatacttg ctacagtttc agttttggct  1320
gttaaaggca gttttggctcc aatatctgga acagttcaaa gtgctcatct tattataaga  1380
tttgacgaaa atggagtgct actaaacaat tccttcctgg acccagaata ttggaacttt  1440
agaaatggag atcttactga aggcacagcc tatacaaacg ctgttggatt tatgcctaac  1500
ctatcagctt atccaaaatc tcacggtaaa actgccaaaa gtaacattgt cagtcaagtt  1560
tacttaaacg gagacaaaac taaacctgta acactaacca ttacactaaa cggtacacag  1620
gaaacaggag acacaactcc aagtgcatac tctatgtcat ttcatgggga ctggtctggc  1680
cacaactaca ttaatgaaat atttgccaca tcctcttaca ctttttcata cattgcccaa  1740
gaataa                                                             1746
```

<210> SEQ ID NO 17

```
<211> LENGTH: 1752
<212> TYPE: DNA
<213> ORGANISM: Adenoviridae
<220> FEATURE:
<221> NAME/KEY: misc_feature
<223> OTHER INFORMATION: /note="Ad5/fib12 chimeric fiber"
<221> NAME/KEY: misc_feature
<222> LOCATION: (1722)..(1722)
<223> OTHER INFORMATION: n can be any nucleotide

<400> SEQUENCE: 17
atgaagcgcg caagaccgtc tgaagatacc ttcaaccccg tgtatccata tgacccattt        60
gacacatcag acgtacccct tgttacaccc ccttttactt cttccaatgg tcttcaagaa       120
aaaccaccag gtgtattagc acttaattac aaagacccca ttgtaactga aaatggaacc       180
cttacactca agctagggga cggaataaaa cttaatgccc aaggtcaact tacagctagt       240
aataatatca atgttttgga gccccttacc aacacctcac aaggtcttaa actttcttgg       300
agcgcccccc tagcagtaaa ggctagtgcc ctcacactta acacaagagc gcccttaacc       360
acaacggatg aaagcttagc cttaataacc gcccctccca ttacagtaga gtcttcgcgt       420
ttgggcttgg ccaccatagc ccctctaagc ttagatggag gtggaaacct aggtttaaat       480
cttttctgct ccctggacgt tagtaacaac aatttgcatc tcaccactga aactccctta       540
gttgtaaatt ctagcggtgc cctatctgtt gctactgcag accccataag tgttcgcaac       600
aacgctctta ccctacctac ggcagatccg ttaatggtga gctccgatgg gttgggaata       660
agtgtcacta gtcccattac agtaataaac ggttccttag ccttgtctac aactgctccc       720
ctcaacagca caggatccac tttaagtctg tctgttgcca atcctctgac tatttcacaa       780
gacacattga ctgttccac tggtaacggt cttcaagtgt cggggtctca attagtaaca       840
agaataggg atggtttaac attcgataat ggggtcatga agtaaacgt tgccggggga       900
atgagaactt ctggcggtag aataatttta gatgttaatt atccctttga tgcgagcaat       960
aacctgtcct taagacgggg attgggacta atttataacc aatctacaaa ctggaactta      1020
acaactgata ttagtaccga aaaggtttta atgtttagtg gcaatcaaat agctcttaat      1080
gcaggtcagg ggcttacatt taataatggc caacttaggg ttaagttggg agctggactt      1140
atttttgatt caaacaataa cattgcctta ggcagcagca gcaacactcc atacgaccct      1200
ctgacactgt ggacaactcc tgacccacca ccaaactgca gcctcataca agagctagat      1260
gcaaaactca ccctgtgctt aacaaaaaac ggatctattg ttaatggcat tgtaagttta      1320
gtgggtgtta agggtaatct cctaaatatc caaagtacta ctaccactgt aggagtgcat      1380
ttagtgtttg atgaacaggg aagattaatc acatcaaccc tactgccct ggttccccaa      1440
gcttcgtggg gatatagaca aggccaatca gtgtctacca atactgttac caatggtcta      1500
ggttttatgc ctaatgtgag tgcttaccct agaccaaatg ccagtgaggc taaaagccaa      1560
atggtaagtc tcacgtactt acagggagat acatctaaac ctataacaat gaaagttgca      1620
tttaatggca ttacgtcgct aaatggatac tctttaacat tcatgtggtc aggtctatca      1680
aactatataa atcagccttt ctctacacca tcctgctcct ntcttacat tgcccaagaa      1740
taaatgcatt ag                                                          1752

<210> SEQ ID NO 18
<211> LENGTH: 1071
<212> TYPE: DNA
<213> ORGANISM: Adenoviridae
<220> FEATURE:
<221> NAME/KEY: misc_feature
```

<223> OTHER INFORMATION: /note="Ad5/fib16 chimeric fiber"

<400> SEQUENCE: 18

| | | | | | |
|---|---|---|---|---|---|
| atgaagcgcg | caagaccgtc | tgaagatacc | ttcaacccccg | tgtatccata | tgaagatgaa | 60 |
| agcagctcac | aacacccctt | tataaaccct | ggtttcattt | cctcaaatgg | ttttgcacaa | 120 |
| agcccagatg | gagttctaac | tcttaaatgt | gttaatccac | tcactaccgc | cagcggaccc | 180 |
| ctccaactta | aagttggaag | cagtcttaca | gtagatacta | tcgatgggtc | tttggaggaa | 240 |
| aatataactg | ccgaagcgcc | actcactaaa | actaaccact | ccataggttt | attaatagga | 300 |
| tctggcttgc | aaacaaagga | tgataaactt | tgtttatcgc | tggagatgg | gttggtaaca | 360 |
| aaggatgata | aactatgttt | atcgctggga | gatgggttaa | taacaaaaaa | tgatgtacta | 420 |
| tgtgccaaac | taggacatgg | ccttgtgttt | gactcttcca | atgctatcac | catagaaaac | 480 |
| aacaccttgt | ggacaggcgc | aaaaccaagc | gccaactgtg | taattaaaga | gggagaagat | 540 |
| tccccagact | gtaagctcac | tttagttcta | gtgaagaatg | gaggactgat | aaatggatac | 600 |
| ataacattaa | tgggagcctc | agaatatact | aacaccttgt | ttaaaaacaa | tcaagttaca | 660 |
| atcgatgtaa | acctcgcatt | tgataatact | ggccaaatta | ttacttacct | atcatcccctt | 720 |
| aaaagtaacc | tgaacttta | agacaaccaa | acatggcta | ctggaaccat | aaccagtgcc | 780 |
| aaaggcttca | tgcccagcac | caccgcctat | ccatttataa | catacgccac | tgagacccta | 840 |
| aatgaagatt | acatttatgg | agagtgttac | tacaaatcta | ccaatggaac | tctcttttca | 900 |
| ctaaaagtta | ctgtcacact | aaacagacgt | atgttagctt | ctggaatggc | ctatgctatg | 960 |
| aattttcat | ggtctctaaa | tgcagaggaa | gccccggaaa | ctaccgaagt | cactctcatt | 1020 |
| acctcccccct | tcttttttc | ttatatcaga | gaagatgact | gaatgcatta | g | 1071 |

<210> SEQ ID NO 19
<211> LENGTH: 1101
<212> TYPE: DNA
<213> ORGANISM: Adenoviridae
<220> FEATURE:
<221> NAME/KEY: misc_feature
<223> OTHER INFORMATION: /note="Ad5/fib28 chimeric fiber"

<400> SEQUENCE: 19

| | | | | | |
|---|---|---|---|---|---|
| atgttgttgc | agatgaagcg | cgcaagaccg | tctgaagata | ccttcaaccc | cgtgtatcca | 60 |
| tatggctacg | cgcggaatca | gaatatcccc | ttcctcactc | ccccctttgt | ttcttccgat | 120 |
| ggattccaaa | acttcccacc | tgggggtcctg | tcactcaaac | tggctgaccc | aatcaccatc | 180 |
| gctaatgggg | atgtctcact | caagttggga | ggcggactga | cggtggaaaa | agagtctgga | 240 |
| aacttaactg | tgaaccctaa | ggctcccttg | caagttgcaa | gtggacaatt | ggaattagca | 300 |
| tatgattctc | catttgatgt | taaaaacaat | atgcttactc | ttaaagcagg | tcacggctta | 360 |
| gcagttgtaa | cgaaagacaa | tactgattta | caaccactaa | tgggcacact | tgttgttta | 420 |
| actggcaaag | gcattggcac | tggcacaagt | gctcacggtg | gaaccataga | tgtgagaata | 480 |
| ggaaaaaacg | gaagtctggc | atttgacaaa | aatggagatt | tggtggcctg | ggataaagaa | 540 |
| aatgacaggc | gcactctatg | gacaactcca | gacacatctc | caaattgcaa | aatgagtgaa | 600 |
| gtcaaagact | caaagcttac | tcttattctt | acaaaatgcg | gaagtcaaat | tctaggaagt | 660 |
| gtatctttgc | ttgctgtaaa | aggagaatat | caaaatatga | ctgccagtac | taataagaat | 720 |
| gtaaaaataa | cactgctatt | tgatgctaat | ggagtcttgt | tagaaggatc | cagtcttgat | 780 |
| aaagagtact | ggaactttag | aaacaatgat | tctactgtgt | ctggaaaata | tgaaaatgct | 840 |

-continued

```
gttccgttca tgcctaacat aacagcttat aaacccgtca attctaaaag ctatgccaga      900
agtcacatat ttggaaatgt atatattgct gctaagccat ataatccagt ggttattaaa      960
attagcttca atcaagagac acaaaacaat tgtgtctatt ctatatcatt tgactacact     1020
tgctctaaag agtatacagg tatgcaattc gatgttacat ctttcacctt ctcctatatc     1080
gcccaagaat gaatgcatta g                                                1101
```

<210> SEQ ID NO 20
<211> LENGTH: 1668
<212> TYPE: DNA
<213> ORGANISM: Adenoviridae
<220> FEATURE:
<221> NAME/KEY: misc_feature
<223> OTHER INFORMATION: /note="Ad5/fib40-L chimeric fiber"
<221> NAME/KEY: misc_feature
<222> LOCATION: (1588)..(1588)
<223> OTHER INFORMATION: n can be any nucleotide

<400> SEQUENCE: 20

```
atgttgttgc agatgaagcg cgcaagaccg tctgaagata ccttcaaccc cgtgtatcca       60
tatgaacact acaatcccct tgacattcca tttattacac ccccgtttgc ttcctccaac      120
ggcttgcaag aaaaacctcc gggagtcctc agcctgaaat acactgatcc acttacaacc      180
aaaaacgggg ctttaacctt aaaattgggc acgggactaa acattgataa aaatggagat      240
ctttcttcag atgctagcgt ggaagttagc gcccctatca ctaaaaccaa caaaatcgta      300
ggtttaaatt acactaagcc ctctcgctctg caaaataacg cgcttactct ttcttacaac      360 gcgccctttta acgtagtaaa taataattta gctctaaata tgtcacagcc tgttactatt      420
aatgcaaaca acgaactttc tctcttaata gacgccccac ttaatgctga cacgggcact      480
cttcgccttc gaagtgatgc acctcttgga ctagtagaca aaacactaaa ggttttgttt      540
tctagccccc tctatctaga taataacttt cttacactag ccattgaacg cccgctagct      600
ctatccagta acagagcagt ggcccttaag tattcaccac ctttaaaaat agaaaacgaa      660
aacttaaccc taagcacagg cggaccttt actgtaagcg ggggaaattt aaacctggca      720
acatcggcac ccctctccgt gcaaaacaat tctctctcct taggggttaa cccgcctttt      780
ctcatcactg actctggatt agctatggac ttaggagacg tcttgcatt aggtggctct      840 aagttaataa tcaatcttgg tccaggttta caaatgtcta atggagctat tactttagca      900
ctagatgcag cgctgccttt gcaatataaa acaaccaac ttcaactcag aattggctcc      960
gcgtctgctt taattatgag cggagtaaca caaacattaa acgtcaatgc caataccagc     1020
aaaggtcttg ctattgaaaa taactcacta gttgttaagc taggaaacgg tcttcgcttt     1080
gatagctggg gaagcatagc tgtctcacct actaccacta ccctaccac cctatggacc     1140 accgcggacc cgtctcctaa cgccacttttt tatgaatcac tagacgccaa agtgtggcta     1200
gttttagtaa aatgcaacgg catggttaac gggaccatat ccattaaagc tcaaaaaggc     1260
actttactta aacccacagc tagctttatt cctttgtca tgtatttta cagcgacgga     1320 acgtggagga aaaactatcc cgtgtttgac aacgaaggga actagcaaa cagtgccaca     1380 tggggttatc gacaaggaca gtctgccaac actaacgttt ccaatgctgt agaatttatg     1440
cctagctcta aaaggtatcc caatgaaaaa ggttctgaag ttcagaacat ggctcttacc     1500
tacacttttt tgcaaggtga ccctaacatg gccatatctt ttcagagcat ttataatcat     1560 gcaatagaaag gctactcatt aaaattcncc tggcgcgttc gaaataatga acgttttgac     1620
atcccctgtt gctcattttc ttatgtaaca gaacaataaa tgcattag                  1668
```

<210> SEQ ID NO 21
<211> LENGTH: 1062
<212> TYPE: DNA
<213> ORGANISM: Adenoviridae
<220> FEATURE:
<221> NAME/KEY: misc_feature
<223> OTHER INFORMATION: /note="Adenovirus16 fiber sequence"

<400> SEQUENCE: 21

| | | |
|---|---|---|
| atggccaaac gagctcggct aagcagctcc ttcaatccgg tctacccta tgaagatgaa | 60 |
| agcagctcac aacacccctt tataaaccct ggtttcattt cctcaaatgg ttttgcacaa | 120 |
| agcccagatg gagttctaac tcttaaatgt gttaatccac tcactaccgc cagcggaccc | 180 |
| ctccaactta aagttggaag cagtcttaca gtagatacta tcgatgggtc tttggaggaa | 240 |
| aatataactg ccgcagcgcc actcactaaa actaaccact ccataggttt attaatagga | 300 |
| tctggcttgc aaacaaagga tgataaactt tgtttatcgc tgggagatgg gttggtaaca | 360 |
| aaggatgata actatgtttt atcgctggga gatgggttaa taacaaaaaa tgatgtacta | 420 |
| tgtgccaaac taggacatgg ccttgtgttt gactcttcca atgctatcac catagaaaac | 480 |
| aacaccttgt ggacaggcgc aaaaccaagc gccaactgtg taattaaaga gggagaagat | 540 |
| tccccagact gtaagctcac tttagttcta gtgaagaatg gaggactgat aaatggatac | 600 |
| ataacattaa tgggagcctc agaatatact aacaccttgt ttaaaaacaa tcaagttaca | 660 |
| atcgatgtaa acctcgcatt tgataatact ggccaaatta ttacttacct atcatcccTt | 720 |
| aaaagtaacc tgaactttaa agacaaccaa acatggcta ctggaaccat aaccagtgcc | 780 |
| aaaggcttca tgcccagcac caccgcctat ccatttataa catacgccac tgagaccta | 840 |
| aatgaagatt acatttatgg agagtgttac tacaaatcta ccaatggaac tctcttccca | 900 |
| ctaaaagtta ctgtcacact aaacagacgt atgttagctt ctggaatggc ctatgctatg | 960 |
| aatttttcat ggtctctaaa tgcagaggaa gccccggaaa ctaccgaagt cactctcatt | 1020 |
| acctcccct tctttttttc ttatatcaga gaagatgact ga | 1062 |

<210> SEQ ID NO 22
<211> LENGTH: 1074
<212> TYPE: DNA
<213> ORGANISM: Adenoviridae
<220> FEATURE:
<221> NAME/KEY: misc_feature
<223> OTHER INFORMATION: /note="Adenovirus5/chimeric fiber16 sequence"

<400> SEQUENCE: 22

| | | |
|---|---|---|
| atgttgttgc agatgaagcg cgcaagaccg tctgaagata ccttcaaccc cgtgtatcca | 60 |
| tatgaagatg aaagcagctc acaacacccc tttataaacc ctggtttcat ttcctcaaat | 120 |
| ggttttgcac aaagcccaga tggagttcta actcttaaat gtgttaatcc actcactacc | 180 |
| gccagcggac ccctccaact taaagttgga agcagtctta cagtagatac tatcgatggg | 240 |
| tctttggagg aaaatataac tgccgaagcg ccactcacta aaactaacca ctccataggt | 300 |
| ttattaatag gatctggctt gcaaacaaag gatgataaac tttgtttatc gctgggagat | 360 |
| gggttggtaa caaaggatga taaactatgt ttatcgctgg gagatgggtt aataacaaaa | 420 |
| aatgatgtac tatgtgccaa actaggacat ggccttgtgt ttgactcttc caatgctatc | 480 |
| accatagaaa acaacacctt gtggacaggc gcaaaaccaa gcgccaactg tgtaattaaa | 540 |
| gagggagaag attccccaga ctgtaagctc actttagttc tagtgaagaa tggaggactg | 600 |

```
ataaatggat acataacatt aatgggagcc tcagaatata ctaacacctt gtttaaaaac    660
aatcaagtta caatcgatgt aaacctcgca tttgataata ctggccaaat tattacttac    720
ctatcatccc ttaaaagtaa cctgaacttt aaagacaacc aaaacatggc tactggaacc    780
ataaccagtg ccaaaggctt catgcccagc accaccgcct atccatttat aacatacgcc    840
actgagaccc taaatgaaga ttacatttat ggagagtgtt actacaaatc taccaatgga    900
actctctttc cactaaaagt tactgtcaca ctaaacagag gtatgttagc ttctggaatg    960
gcctatgcta tgaattttc atggtctcta aatgcagagg aagccccgga aactaccgaa   1020
gtcactctca ttcctccccc cttcttttt tcttatatca gagaagatga ctga         1074
```

<210> SEQ ID NO 23
<211> LENGTH: 353
<212> TYPE: PRT
<213> ORGANISM: Adenoviridae
<220> FEATURE:
<221> NAME/KEY: misc_feature
<223> OTHER INFORMATION: /note="Adenovirus16 fiber protein sequence"

<400> SEQUENCE: 23

```
Met Ala Lys Arg Ala Arg Leu Ser Ser Ser Phe Asn Pro Val Tyr Pro
1               5                   10                  15

Tyr Glu Asp Glu Ser Ser Gln His Pro Phe Ile Asn Pro Gly Phe
            20                  25                  30

Ile Ser Ser Asn Gly Phe Ala Gln Ser Pro Asp Gly Val Leu Thr Leu
        35                  40                  45

Lys Cys Val Asn Pro Leu Thr Thr Ala Ser Gly Pro Leu Gln Leu Lys
    50                  55                  60

Val Gly Ser Ser Leu Thr Val Asp Thr Ile Asp Gly Ser Leu Glu Glu
65                  70                  75                  80

Asn Ile Thr Ala Ala Ala Pro Leu Thr Lys Thr Asn His Ser Ile Gly
                85                  90                  95

Leu Leu Ile Gly Ser Gly Leu Gln Thr Lys Asp Asp Lys Leu Cys Leu
            100                 105                 110

Ser Leu Gly Asp Gly Leu Val Thr Lys Asp Asp Lys Leu Cys Leu Ser
        115                 120                 125

Leu Gly Asp Gly Leu Ile Thr Lys Asn Asp Val Leu Cys Ala Lys Leu
    130                 135                 140

Gly His Gly Leu Val Phe Asp Ser Ser Asn Ala Ile Thr Ile Glu Asn
145                 150                 155                 160

Asn Thr Leu Trp Thr Gly Ala Lys Pro Ser Ala Asn Cys Val Ile Lys
                165                 170                 175

Glu Gly Glu Asp Ser Pro Asp Cys Lys Leu Thr Leu Val Leu Val Lys
            180                 185                 190

Asn Gly Gly Leu Ile Asn Gly Tyr Ile Thr Leu Met Gly Ala Ser Glu
        195                 200                 205

Tyr Thr Asn Thr Leu Phe Lys Asn Asn Gln Val Thr Ile Asp Val Asn
    210                 215                 220

Leu Ala Phe Asp Asn Thr Gly Gln Ile Ile Thr Tyr Leu Ser Ser Leu
225                 230                 235                 240

Lys Ser Asn Leu Asn Phe Lys Asp Asn Gln Asn Met Ala Thr Gly Thr
                245                 250                 255

Ile Thr Ser Ala Lys Gly Phe Met Pro Ser Thr Thr Ala Tyr Pro Phe
            260                 265                 270

Ile Thr Tyr Ala Thr Glu Thr Leu Asn Glu Asp Tyr Ile Tyr Gly Glu
```

```
              275                 280                 285
Cys Tyr Tyr Lys Ser Thr Asn Gly Thr Leu Phe Pro Leu Lys Val Thr
        290                 295                 300

Val Thr Leu Asn Arg Arg Met Leu Ala Ser Gly Met Ala Tyr Ala Met
305                 310                 315                 320

Asn Phe Ser Trp Ser Leu Asn Ala Glu Glu Ala Pro Glu Thr Thr Glu
                325                 330                 335

Val Thr Leu Ile Thr Ser Pro Phe Phe Ser Tyr Ile Arg Glu Asp
        340                 345                 350

Asp

<210> SEQ ID NO 24
<211> LENGTH: 353
<212> TYPE: PRT
<213> ORGANISM: Adenoviridae
<220> FEATURE:
<221> NAME/KEY: misc_feature
<223> OTHER INFORMATION: /note="Adenovirus16A fiber protein sequence"

<400> SEQUENCE: 24

Met Lys Arg Ala Arg Pro Ser Glu Asp Thr Phe Asn Pro Val Tyr Pro
1               5                   10                  15

Tyr Glu Asp Glu Ser Ser Ser Gln His Pro Phe Ile Asn Pro Gly Phe
            20                  25                  30

Ile Ser Ser Asn Gly Phe Ala Gln Ser Pro Asp Gly Val Leu Thr Leu
        35                  40                  45

Lys Cys Val Asn Pro Leu Thr Thr Ala Ser Gly Pro Leu Gln Leu Lys
    50                  55                  60

Val Gly Ser Ser Leu Thr Val Asp Thr Ile Asp Gly Ser Leu Glu Glu
65                  70                  75                  80

Asn Ile Thr Ala Glu Ala Pro Leu Thr Lys Thr Asn His Ser Ile Gly
                85                  90                  95

Leu Leu Ile Gly Ser Gly Leu Gln Thr Lys Asp Asp Lys Leu Cys Leu
            100                 105                 110

Ser Leu Gly Asp Gly Leu Val Thr Lys Asp Asp Lys Leu Cys Leu Ser
        115                 120                 125

Leu Gly Asp Gly Leu Ile Thr Lys Asn Asp Val Leu Cys Ala Lys Leu
    130                 135                 140

Gly His Gly Leu Val Phe Asp Ser Ser Asn Ala Ile Thr Ile Glu Asn
145                 150                 155                 160

Asn Thr Leu Trp Thr Gly Ala Lys Pro Ser Ala Asn Cys Val Ile Lys
                165                 170                 175

Glu Gly Glu Asp Ser Pro Asp Cys Lys Leu Thr Leu Val Leu Val Lys
            180                 185                 190

Asn Gly Gly Leu Ile Asn Gly Tyr Ile Thr Leu Met Gly Ala Ser Glu
        195                 200                 205

Tyr Thr Asn Thr Leu Phe Lys Asn Asn Gln Val Thr Ile Asp Val Asn
    210                 215                 220

Leu Ala Phe Asp Asn Thr Gly Gln Ile Ile Thr Tyr Leu Ser Ser Leu
225                 230                 235                 240

Lys Ser Asn Leu Asn Phe Lys Asp Asn Gln Asn Met Ala Thr Gly Thr
                245                 250                 255

Ile Thr Ser Ala Lys Gly Phe Met Pro Ser Thr Thr Ala Tyr Pro Phe
            260                 265                 270

Ile Thr Tyr Ala Thr Glu Thr Leu Asn Glu Asp Tyr Ile Tyr Gly Glu
```

-continued

```
              275                 280                      285
Cys Tyr Tyr Lys Ser Thr Asn Gly Thr Leu Phe Pro Leu Lys Val Thr
    290                     295                 300

Val Thr Leu Asn Arg Arg Met Leu Ala Ser Gly Met Ala Tyr Ala Met
305                 310                 315                 320

Asn Phe Ser Trp Ser Leu Asn Ala Glu Glu Ala Pro Glu Thr Thr Glu
                325                 330                 335

Val Thr Leu Ile Thr Ser Pro Phe Phe Phe Ser Tyr Ile Arg Glu Asp
                340                 345                 350

Asp
```